US012590149B2

(12) United States Patent
Liu

(10) Patent No.: US 12,590,149 B2
(45) Date of Patent: Mar. 31, 2026

(54) ANTIBODY AND BISPECIFIC ANTIBODY TARGETING LAG-3 AND USE THEREOF

(71) Applicant: L&L Bio Co., Ltd., Ningbo, China, Zhejiang (CN)

(72) Inventor: Jiajian Liu, Shanghai (CN)

(73) Assignee: L&L Bio Co., Ltd., Ningbo, China, Shanghai (CN)

( * ) Notice: Subject to any disclaimer, the term of this patent is extended or adjusted under 35 U.S.C. 154(b) by 1084 days.

(21) Appl. No.: 17/615,832

(22) PCT Filed: Jun. 11, 2020

(86) PCT No.: PCT/CN2020/095577
§ 371 (c)(1),
(2) Date: Dec. 2, 2021

(87) PCT Pub. No.: WO2020/249041
PCT Pub. Date: Dec. 17, 2020

(65) Prior Publication Data

US 2022/0340657 A1    Oct. 27, 2022

(30) Foreign Application Priority Data

Jun. 13, 2019    (CN) .......................... 201910510292.6

(51) Int. Cl.
| | |
|---|---|
| *C07K 16/28* | (2006.01) |
| *A61K 39/00* | (2006.01) |
| *A61P 35/00* | (2006.01) |
| *C07K 16/46* | (2006.01) |

(52) U.S. Cl.
CPC .......... *C07K 16/2803* (2013.01); *A61P 35/00* (2018.01); *C07K 16/46* (2013.01); *A61K 2039/505* (2013.01); *C07K 2317/24* (2013.01); *C07K 2317/31* (2013.01); *C07K 2317/565* (2013.01); *C07K 2317/622* (2013.01); *C07K 2317/92* (2013.01)

(58) Field of Classification Search
None
See application file for complete search history.

(56) References Cited

U.S. PATENT DOCUMENTS

| | | |
|---|---|---|
| 10,160,806 B2 | 12/2018 | Bonvini et al. |
| 2016/0222116 A1 | 8/2016 | Korman et al. |
| 2019/0010231 A1 | 1/2019 | Rothe et al. |

FOREIGN PATENT DOCUMENTS

| | | | | |
|---|---|---|---|---|
| CN | 105793287 A | 7/2016 | | |
| CN | 106715470 A | 4/2018 | | |
| CN | 107922470 A | 4/2018 | | |
| WO | WO-2017025498 A1 * | 2/2017 | .............. | A61P 35/00 |
| WO | 2018134279 A1 | 7/2018 | | |

OTHER PUBLICATIONS

Cappello, et. al, Cancer Research, 2003, 63, 2518-2525 (Year: 2003).*
Triebel, Trends in Immuno, 2003, 24, 619-622 (Year: 2003).*
NIH-NCI, "Cancer Prevention Overview," 2023, accessed Mar. 17, 2025 (Year: 2023).*
Chavanton, et. al, Cancer Science, 2024, 115, 2494-2505 (Year: 2024).*
Mayo Clinic, "Cancer Treatment," 2024, accessed Mar. 17, 2025 (Year: 2024).*
NCFR, "Cancer Intervention vs Prevention: What does it Mean?," 2024, accessed Mar. 17, 2025 (Year: 2024).*
Yu, et al., Immunol Rev, 2024, 1, 98-112 (Year: 2024).*
Andrews, et al., Immunol Rev, 2017, 276, 80-96 (Year: 2017).*
Sep. 9, 2020 International Search Report issued in International Patent Application No. PCT/CN2020/095577.
Sep. 9, 2020 Written Opinion of the International Searching Authority issued in International Patent Application No. PCT/CN2020/095577.

* cited by examiner

*Primary Examiner* — Misook Yu
*Assistant Examiner* — Samantha Lake Hopkins
(74) *Attorney, Agent, or Firm* — Houston Beshining Law Office PLLC; Liangang Ye

(57) ABSTRACT

Disclosed is a LAG-3 binding protein, comprising a light chain variable region and/or a heavy chain variable region. The light chain variable region comprises a CDR1 having an amino acid sequence as shown in SEQ ID NO: 5, a CDR2 having an amino acid sequence as shown in SEQ ID NO: 6, and/or a CDR3 having an amino acid sequence as shown in SEQ ID NO: 7. The heavy chain variable region comprises a CDRI having an amino acid sequence as shown in SEQ ID NO: 8, a CDR2 having an amino acid sequence as shown in SEQ ID NO: 9, and/or a CDR3 having an amino acid sequence as shown in SEQ ID NO: 10. Also disclosed are a bispecific antibody targeting LAG-3 and use thereof. The LAG-3 binding protein and bispecific antibody above can effectively block the binding of LAG-3 to MHC II and activate T cells.

20 Claims, 5 Drawing Sheets
Specification includes a Sequence Listing.

ANTIBODY AND BISPECIFIC ANTIBODY TARGETING LAG-3 AND USE THEREOF

REFERENCE TO SEQUENCE LISTING

The Sequence Listing is submitted concurrently with the specification as an ASCII formatted text file via EFS-Web, with a file name of "P21415379US-2-SEQ-v2", a creation date of Jun. 6, 2025, and a size of 79,621 bytes. The Sequence Listing filed via EFS-Web is part of the specification and is incorporated in its entirety by reference herein.

The present application is a National Stage of International Application No. PCT/CN2020/095577, filed on Jun. 11, 2020, which claims priority of the Chinese Patent Application No. CN201910510292.6, filed on Jun. 13, 2019, the contents of which are incorporated herein by reference in their entireties.

TECHNICAL FIELD

The present invention belongs to the field of biomedicine, and specifically relates to an antibody and a bispecific antibody targeting LAG-3 and the use thereof.

BACKGROUND ARTS

Lymphocyte-activation gene 3 (LAG-3) belongs to the superfamily of immunoglobulins, which consists of 3 parts: an extracellular region, a transmembrane region, and a cytoplasmic region. The gene encoding LAG-3 is located on chromosome 12 (12P13), which is similar to the chromosomal localization and structure of CD4 molecule. LAG-3 is expressed on activated T cells, depleted T cells, tumor-infiltrating T cells, and regulatory T cells (Treg). After binding to the major histocompatibility complex 2 (MHC class II), the LAG-3/MHC class II interaction results in negative regulation of T cell proliferation, activation, and homeostasis in vivo. Inhibition of LAG-3 can relieve the inhibition of NMCII-polypeptide-T cell receptor antigen presentation caused by LAG-3 and allow T cells to regain cytotoxicity, thereby enhancing its killing effect on tumors. At the same time, inhibition of LAG-3 can also reduce the function of regulatory T cells in suppressing immune response. Therefore, LAG-3 is considered to be a more attractive target than other immune checkpoint proteins.

Among the current second-generation targets of immune checkpoints, LAG-3 is a target with more clinical data and relatively determined druggability, which means antibody drugs targeting this target may become important antitumor drugs in the future. However, there is currently no drug targeting LAG-3 on the market worldwide. By the end of 2018, a total of 30 drugs were under clinical research. LAG-3 antibodies in the clinical research stage include GSK2831781 of GSK, LAG525 of Novartis, REGN3767 of Regeneron, and TSR-033 of Tesaro. Much effort has been devoted to the development of the combination therapy of LAG-3 antibody drugs with PD-1. Wherein those having the most advanced progress in R&D are Relatlimab developed by BMS and Ono in Phase II/III clinical trials, IMP321 in Phase II clinical trials, and LAG525 in Phase I/II clinical trials. There are 8 drugs in Phase I clinical trials and 9 drugs in preclinical trials. The main therapeutic fields of drugs targeting LAG-3 include cancer and autoimmune diseases. Relatlimab of Bristol-Myers Squibb (R&D code BMS-986016, originally developed by Medarex). MGD013 of MacroGenics, a PD-1/LAG-3 bispecific antibody with a long half-life in serum, have the potential to treat a variety of different cancers by blocking immunosuppression of both immune checkpoint molecules simultaneously.

However, clinically, there is still a lack of antibodies targeting LAG-3 with better thermal stability, better T cell activity, effective blocking of the binding of LAG-3 and MHC II, better in vivo efficacy and better PK, as well as bispecific antibodies targeting LAG-3 with simple structure, stable molecule and simple production process.

Content of the Present Invention

In order to overcome the defect that it lacks antibody targeting LAG-3 with more stability and better activity as well as bispecific antibody targeting LAG-3 with simple structure, molecular stability and simple production process, the present invention provides an antibody and a bispecific antibody targeting LAG-3 and a use thereof. The bispecific antibody of the present invention is a sequence-based IgG like bispecific antibody (SBody), and this design will be referred to as SBody in the present patent.

The present invention provides an antibody targeting LAG-3 through optimal design and screening, and the antibody has novel CDR1, CDR2 and CDR3 of light chain variable region as well as CDR1, CDR2 and CDR3 of heavy chain variable regions, which has good thermal stability and better activation to T cell, can more effectively block the binding of LAG-3 to MHC II, and has better in vivo efficacy and PK properties. A bispecific antibody targeting LAG-3 is also provided which simultaneously targets LAG-3 and another target; this novel design can achieve the effect of one molecule targeting two specific targets at the same time, so that one molecule can replace the combination of two molecules and even have the synergistic effect on treating tumors. The production process, production cost and clinical trial of one molecule are more convenient and have lower cost than the combination of two separate molecules.

In order to solve the technical problems described above, the first technical solution of the present invention is to provide: a LAG-3 binding protein comprising a light chain variable region and/or a heavy chain variable region; wherein the light chain variable region comprises a CDR1 having an amino acid sequence of SEQ ID NO: 5, a CDR2 having an amino acid sequence of SEQ ID NO: 6, and/or, a CDR3 having an amino acid sequence of SEQ ID NO: 7; the heavy chain variable region comprises a CDR1 having an amino acid sequence of SEQ ID NO: 8, a CDR2 having an amino acid sequence of SEQ ID NO: 9, and/or, a CDR3 having an amino acid sequence of SEQ ID NO: 10.

The LAG-3 binding protein as described above, wherein J gene region of the light chain variable region is selected from the group consisting of: hJK1, hJK2.1, hJK2.2, hJK2.3, hJK2.4, hJK3, hJK4.1, hJK4.2 and hJK5, preferably hJK4.1;

and/or, the J gene region of the heavy chain variable region is selected from the following group consisting of: hJh1, hJh2, hJh3.1, hJh3.2, hJh4.1, hJh4.2, hJh4.3, hJh5.2, hJh6.1, hJh6.2 and hJh6.3, preferably hJh4.1.

In some preferred embodiments there is provided the LAG-3 binding protein described above, wherein the light chain variable region comprises an amino acid sequence of SEQ ID NO: 3, SEQ ID NO: 23-29 or a variant thereof, and/or, the heavy chain variable region comprises an amino acid sequence of SEQ ID NO: 4, SEQ ID NO: 30-37 or a variant thereof, the variant has substitution, deletion or addition of one or more amino acid residues in the original amino acid sequence, preferably at least 80%, 85%, 90%, 95%, 96%, 97%, 98% or 99% sequence identity to the original amino acid sequence, and the variant retains or improves binding of antibody to the LAG-3;

preferably, the light chain variable region comprises an amino acid sequence of SEQ ID NO: 3, and the heavy chain variable region comprises an amino acid sequence of SEQ ID NO: 4; the light chain variable region comprises an amino acid sequence of SEQ ID NO: 23, and the heavy chain variable region comprises an amino acid sequence of SEQ ID NO: 30; the light chain variable region comprises an amino acid sequence of SEQ ID NO: 23, and the heavy chain variable region comprises an amino acid sequence of SEQ ID NO: 31; the light chain variable region comprises an amino acid sequence of SEQ ID NO: 24, and the heavy chain variable region comprises an amino acid sequence of SEQ ID NO: 31; the light chain variable region comprises an amino acid sequence of SEQ ID NO: 25, and the heavy chain variable region comprises an amino acid sequence of SEQ ID NO: 31; the light chain variable region comprises an amino acid sequence of SEQ ID NO: 26, and the heavy chain variable region comprises an amino acid sequence of SEQ ID NO: 31; the light chain variable region comprises an amino acid sequence of SEQ ID NO: 27, and the heavy chain variable region comprises an amino acid sequence of SEQ ID NO: 31; the light chain variable region comprises an amino acid sequence of SEQ ID NO: 28, and the heavy chain variable region comprises an amino acid sequence of SEQ ID NO: 31; the light chain variable region comprises an amino acid sequence of SEQ ID NO: 29, and the heavy chain variable region comprises an amino acid sequence of SEQ ID NO: 31; the light chain variable region comprises an amino acid sequence of SEQ ID NO: 25, and the heavy chain variable region comprises an amino acid sequence of SEQ ID NO: 32; the light chain variable region comprises an amino acid sequence of SEQ ID NO: 26, and the heavy chain variable region comprises an amino acid sequence of SEQ ID NO: 32; the light chain variable region comprises an amino acid sequence of SEQ ID NO: 28, and the heavy chain variable region comprises an amino acid sequence of SEQ ID NO: 30; the light chain variable region comprises an amino acid sequence of SEQ ID NO: 28, and the heavy chain variable region comprises an amino acid sequence of SEQ ID NO: 33; the light chain variable region comprises an amino acid sequence of SEQ ID NO: 28, and the heavy chain variable region comprises an amino acid sequence of SEQ ID NO: 34; the light chain variable region comprises an amino acid sequence of SEQ ID NO: 28, and the heavy chain variable region comprises an amino acid sequence of SEQ ID NO: 35; the light chain variable region comprises an amino acid sequence of SEQ ID NO: 28, and the heavy chain variable region comprises an amino acid sequence of SEQ ID NO: 36; the light chain variable region comprises an amino acid sequence of SEQ ID NO: 28, and the heavy chain variable region comprises an amino acid sequence of SEQ ID NO: 37.

In some preferred embodiments, the LAG-3 binding protein described above is an antibody, a Fab, a Fab', a F(ab')₂, a Fv, a scFv, a bispecific antibody, a multispecific antibody, a single domain antibody or a single region antibody, or a monoclonal antibody or a polyclonal antibody derived from the antibody as defined above.

In some preferred embodiments, the LAG-3 binding protein described above is an immunoglobulin comprising a human antibody light chain constant region and a human antibody heavy chain constant region. Preferably, the light chain constant region of the human antibody is a κ chain or a λ chain, or the heavy chain constant region of the human antibody is a hIgG1, a hIgG2, a hIgG4 or a variant thereof, the variant has substitution, deletion or addition of one or more amino acid residues in the original amino acid sequence, preferably the variant has at least 80%, 85%, 90%, 95%, 96%, 97%, 98% or 99% sequence identity to the original amino acid sequence, and the variant retains or improves the binding of the antibody to the LAG-3.

In some preferred embodiments, the LAG-3 binding protein described above has a light chain comprising an amino acid sequence of SEQ ID NO: 38 or SEQ ID NO: 39 or a variant thereof, and/or, a heavy chain comprising an amino acid sequence of SEQ ID NO: 40, SEQ ID NO: 41 or a variant thereof, the variant has substitution, deletion or addition of one or more amino acid residues in the original amino acid sequence, preferably the variant has at least 80%, 85%, 90%, 95%, 96%, 97%, 98% or 99% sequence identity to the original amino acid sequence, and the variant retains or improves binding of antibody to LAG-3.

Preferably, the amino acid sequence of the light chain is SEQ ID NO: 38; the amino acid sequence of the heavy chain is SEQ ID NO: 40; or the amino acid sequence of the light chain is SEQ ID NO: 38; the amino acid sequence of the heavy chain is SEQ ID NO: 41; or the amino acid sequence of the light chain is SEQ ID NO: 39; the amino acid sequence of the heavy chain is SEQ ID NO: 40; or the amino acid sequence of the light chain is SEQ ID NO: 39; the amino acid sequence of the heavy chain is SEQ ID NO: 41.

In order to solve the technical problems described above, the second technical solution of the present invention is to provide: a bispecific antibody targeting LAG-3 comprising a first protein functional region and a second protein functional region, wherein the first protein functional region is the LAG-3 binding protein as described in the first technical solution; the second protein functional region is a non-LAG-3 binding protein; preferably, the first protein functional region and the second protein functional region are selected from the group consisting of immunoglobulin, scFv (single-chain Fv, also known as single-chain variable fragment), Fab, Fab' or F(ab')₂, respectively, and only one of the first protein functional region and the second protein functional region is immunoglobulin.

In order to design a bispecific antibody with simple production process and retained effective activity, the bispecific antibody of the present invention is in the form of a structure similar to normal IgG, specifically, protein functional regions comprising light chain and/or heavy chain variable regions that can target two targets are designed, and two protein functional regions share the same Fc region. Preferably, antibody molecule targeting one target in the form of one or more scFvs is linked to one end of the light or heavy chain of an intact antibody targeting another target. Therefore, the heterogeneity of the expression products caused by the expression of different Fcs and/or different light chains is avoided, for example, in the co-expression of the Fc in a Knob form and the Fc in a Hole form, an heterogeneity Fc-Fc pairing form can be formed in the expression process, which brings a lot of inconvenience to the purification process; it can also avoid the possible influence of cross design of the light and heavy chain partial region on binding activity and Fc mismatching which occurs during the production process. The design of one or more scFvs also allows for the adjust ion of the activity for a specific target.

Thus, in some preferred embodiments there is provided the bispecific antibody targeting LAG-3 described above, wherein the first protein functional region is an immunoglobulin, and the second protein functional region is one or more scFvs; or the first protein functional region is one or more scFvs, the second protein functional region is an immunoglobulin, and the constant region of the immunoglobulin comprises a light chain constant region of human antibody and a heavy chain constant region of human antibody. Preferably, the light chain constant region of human antibody is a κ chain or a λ chain, and the heavy chain constant region of human antibody is a hIgG1, a hIgG2, a hIgG4 or a variant thereof, the variant has substitution, deletion or addition of one or more amino acid residues of the original amino acid sequence, preferably the variant has at least 80%, 85%, 90%, 95%, 96%, 97%, 98% or 99% sequence identity to the original amino acid sequence, and the variant retains or improves the binding of the antibody to the antigens such as LAG-3, PD-1, etc.

In some preferred embodiments there is provided the bispecific antibody targeting LAG-3 described above, wherein the scFv comprises a heavy chain variable region and a light chain variable region which are connected by a linker; the scFv is connected to the immunoglobulin by a linker, preferably the linker is (Gly-Gly-Gly-Gly-Ser)$_w$ [hereinafter abbreviated as (G$_4$S)$_w$]; the w is preferably an integer between 0 and 10, more preferably 1, 2, 3 or 4. When w is 1, the sequence (Gly-Gly-Gly-Gly-Ser)$_w$ is numbered as SEQ ID NO: 51. When w is 2, the sequence (Gly-Gly-Gly-Gly-Ser)$_w$ is numbered as SEQ ID NO: 52. When w is 3, the sequence (Gly-Gly-Gly-Gly-Ser)$_w$ is numbered as SEQ ID NO: 53. When w is 4, the sequence (Gly-Gly-Gly-Gly-Ser)$_w$ is numbered as SEQ ID NO: 54. A summary of the bispecific design (formula 1) is shown in Table 10 of Example 12. Furthermore, the linker may also be selected from peptide fragments conventionally used as linkers in the art.

In some preferred embodiments there is provided the bispecific antibody targeting LAG-3 described above, wherein the scFv has a structure of light chain variable region-linker-heavy chain variable region, in which N-terminus of the light chain variable region or C-terminus of the heavy chain variable region is correspondingly linked to C-terminus or N-terminus of the light chain and/or heavy chain of the immunoglobulin by a linker; or the scFv has a structure of heavy chain variable region-linker-light chain variable region, in which N-terminus of the heavy chain variable region or C-terminus of the light chain variable region is correspondingly linked to C-terminus or N-terminus of the light chain and/or the heavy chain of the immunoglobulin by a linker.

In some preferred embodiments there is provided the bispecific antibody targeting LAG-3 described above, wherein the linker is (G$_4$S)$_3$ (SEQ ID NO: 53), and/or, the number of the scFv is two, and these two scFvs are symmetrically linked to the C-terminus or the N-terminus of the light chains and/or the heavy chains of the immunoglobulin. Preferably, the scFv has a structure of light chain variable region-linker-heavy chain variable region, and the C-terminus of the heavy chain variable regions of these two scFvs are symmetrically linked to the N-terminus of two heavy chain variable regions of the immunoglobulin by (G$_4$S)$_3$, respectively, or the N-terminus of the light chain variable regions of the two scFvs are symmetrically linked to the C-terminus of the two heavy chains of the immunoglobulin by (G$_4$S)$_3$, respectively; or the scFv has a structure of a heavy chain variable region-linker-light chain variable region, and the C-terminus of the light chain variable regions of these two scFvs are symmetrically linked to the N-terminus of two light chain variable regions of the immunoglobulin by (G$_4$S)$_3$, respectively, or the N-terminus of the heavy chain variable regions of these two scFvs are symmetrically linked to the C-terminus of two light chain variable regions of the immunoglobulin by (G$_4$S)$_3$, respectively.

In some preferred embodiments there is provided the bispecific antibody targeting LAG-3 described above, wherein the second protein functional region targets PD-1. Preferably, the second protein functional region is an anti-PD-1 antibody. More preferably, the anti-PD-1 antibody is Nivolumab or Pembrolizumab.

In some preferred embodiments there is provided the bispecific antibody targeting LAG-3 described above is selected from the group consisting of:

(1) the first protein functional region is an immunoglobulin comprising the following light chain and heavy chain or variants thereof: the amino acid sequence of the light chain is SEQ ID NO: 38, the amino acid sequence of the heavy chain is SEQ ID NO: 40; or the amino acid sequence of the light chain is SEQ ID NO: 38, the amino acid sequence of the heavy chain is SEQ ID NO: 41; or the amino acid sequence of the light chain is SEQ ID NO: 39, the amino acid sequence of the heavy chain is SEQ ID NO: 40; or the amino acid sequence of the light chain is SEQ ID NO: 39, the amino acid sequence of the heavy chain is SEQ ID NO: 41; and/or, the second protein functional region is a scFv or a variant thereof, wherein the amino acid sequence of the light chain variable region of the scFv is located at positions 1-107 of SEQ ID NO: 42, and the amino acid sequence of the heavy chain variable region of the scFv is located at positions 1-113 of SEQ ID NO: 43; or the amino acid sequence of the light chain variable region of the scFv is located at positions 1-111 of SEQ ID NO: 44, and the amino acid sequence of the heavy chain variable region of the scFv is located at positions 1-120 of SEQ ID NO: 45;

the said variant has substitution, deletion or addition of one or more amino acid residues of the original amino acid sequence, preferably, the variant has at least 80%, 85%, 90%, 95%, 96%, 97%, 98%, 99% sequence identity to the original amino acid sequence, and the variant retains or improves the binding of the antibody to the antigens such as LAG-3, PD-1, etc.

Preferably, when the scFv is linked to the C-terminus of the two heavy chains of the immunoglobulin, the C-terminus of the heavy chain is mutated from K to A;

(2) the functional region of the first protein is a scFv or a variant thereof, wherein the amino acid sequence of the light chain variable region of the scFv is SEQ ID NO: 23-29; and/or, the amino acid sequence of the heavy chain variable region of the scFv is SEQ ID NO: 30-37; and/or, the amino acid sequence of the light chain of the immunoglobulin is SEQ ID NO: 42, the amino acid sequence of the heavy chain of the immunoglobulin is SEQ ID NO: 43; or the amino acid sequence of the light chain of the immunoglobulin is SEQ ID NO: 44, the amino acid sequence of the heavy chain of the immunoglobulin is SEQ ID NO: 45;

the variant has substitution, deletion or addition of one or more amino acid residues of the original amino acid sequence, preferably, the variant has at least 80%, 85%, 90%, 95%, 96%, 97%, 98%, 99% sequence identity to the original amino acid sequences, and the variant retains or improves binding of antibody to antigens, such as LAG-3, PD-1, etc.;

preferably, when the scFv is linked to the C-terminus of the two heavy chains of the immunoglobulin, the C-terminus of the heavy chains is mutated from K to A;

in some preferred embodiments there is provided the bispecific antibody targeting LAG-3 described above, wherein, (i) the first protein functional region is scFv, wherein the amino acid sequence of the light chain variable region of the scFv is SEQ ID NO: 28, the amino acid sequence of the heavy chain variable region of the scFv is SEQ ID NO: 31, and the linker is $(G_4S)_3$; the second protein functional region is an immunoglobulin, wherein the amino acid sequence of the light chain of the immunoglobulin is SEQ ID NO: 42, and the amino acid sequence of the heavy chain of the immunoglobulin is SEQ ID NO: 43;

wherein, the number of the scFv is two; the scFv has a structure of light chain variable region-linker-heavy chain variable region, and the C-terminus of the heavy chain variable regions of these two scFvs are symmetrically linked to the N-terminus of two heavy chains of the immunoglobulin by $(G_4S)_3$, respectively; or the scFv has a structure of heavy chain variable region-linker-light chain variable region, and the N-terminus of the heavy chain variable regions of these two scFvs are symmetrically linked to the C-terminus of two heavy chains of the immunoglobulin by $(G_4S)_3$, respectively, and the C-terminus is mutated from K to A; or the scFv has a structure of light chain variable region-linker-heavy chain variable region, the C-terminus of the heavy chain variable regions of these two scFvs are symmetrically linked to the N-terminus of two light chains of the immunoglobulin by $(G_4S)_3$, respectively; or the scFv has a structure of heavy chain variable region-linker-light chain variable region, the N-terminus of the heavy chain variable regions of these two scFvs are symmetrically linked to the C-terminus of two light chains of the immunoglobulin by $(G_4S)_3$, respectively; or (ii) the first protein functional region is scFv, wherein the amino acid sequence of the light chain variable region of the scFv is SEQ ID NO: 28, the amino acid sequence of the heavy chain variable region of the scFv is SEQ ID NO: 31, and the linker is $(G_4S)_3$; the second protein functional region is an immunoglobulin, wherein the amino acid sequence of the light chain of the immunoglobulin is SEQ ID NO: 44, and the amino acid sequence of the heavy chain of the immunoglobulin is SEQ ID NO: 45;

wherein, the number of the scFv is two; the scFv has a structure of light chain variable region-linker-heavy chain variable region, and the C-terminus of the heavy chain variable regions of these two scFvs are symmetrically linked to the N-terminus of two heavy chains of the immunoglobulin by $(G_4S)_3$, respectively; or the scFv has a structure of heavy chain variable region-linker-light chain variable region, and the N-terminus of the heavy chain variable regions of these two scFvs are symmetrically linked to the C-terminus of two heavy chains of the immunoglobulin through $(G_4S)_3$, respectively, and the C-terminus is mutated from K to A; or the scFv has a structure of light chain variable region-linker-heavy chain variable region, the C-terminus of the heavy chain variable regions of these two scFvs are symmetrically linked to the N-terminus of two light chains of the immunoglobulin by $(G_4S)_3$, respectively; or the scFv has a structure of heavy chain variable region-linker-light chain variable region, the N-terminus of the heavy chain variable regions of the two scFvs are symmetrically linked to the C-terminus of the two light chains of the immunoglobulin by $(G_4S)_3$, respectively; or (iii) the functional region of the first protein is scFv, the number of the scFv is two, wherein the amino acid sequence of the light chain variable region of the scFv is SEQ ID NO: 28, the amino acid sequence of the heavy chain variable region of the scFv is SEQ ID NO: 36, and the linker is $(G_4S)_3$; the functional region of the second protein is an immunoglobulin, the amino acid sequence of the light chain of the immunoglobulin is SEQ ID NO: 44, and the amino acid sequence of the heavy chain of the immunoglobulin is SEQ ID NO: 45;

wherein, the number of the scFv is two; the scFv has a structure of light chain variable region-linker-heavy chain variable region, the C-terminus of the heavy chain variable regions of the two scFvs are symmetrically linked to the N-terminus of the two heavy chains of the immunoglobulin by $(G_4S)_3$, respectively; or the scFv has a structure of a heavy chain variable region-linker-light chain variable region, the N-terminus of the heavy chain variable regions of the two scFvs are symmetrically linked to the C-terminus of the two heavy chains of the immunoglobulin by $(G_4S)_3$, respectively, and the C-terminus is mutated from K to A.

In some preferred embodiments there is provided the bispecific antibody targeting LAG-3 comprises the following amino acid sequences:

an amino acid sequence of SEQ ID NO: 44 as a light chain sequence, and an amino acid sequence of SEQ ID NO: 46 as a heavy chain containing sequence; or an amino acid sequence of SEQ ID NO: 42 as a light chain sequence, and an amino acid sequence of SEQ ID NO: 47 as a heavy chain containing sequence; or an amino acid sequence of SEQ ID NO: 42 as a light chain sequence, and an amino acid sequence of SEQ ID NO: 48 as a heavy chain containing sequence; or an amino acid sequence of SEQ ID NO: 49 as a light chain containing sequence, and an amino acid sequence of SEQ ID NO: 43 as a heavy chain sequence; or an amino acid sequence of SEQ ID NO: 50 as a light chain containing sequence, and an amino acid sequence of SEQ ID NO: 43 as a heavy chain sequence.

Or, the bispecific antibody described in the present invention is a Dual-variable domain Ig (DVD-Ig) bispecific antibody, and the structure thereof is that the N-terminus of light chains and heavy chains of a normal antibody are respectively linked to VL and VH of another antibody, and the dual functions are realized by targeting two targets using the variable regions of two antibodies. The design summary of the bispecific antibody (formula 2) is shown in Table 12 of Example 12.

In a preferred specific embodiment there is provided the bispecific antibody consists of a sequence comprising a light chain and a sequence comprising a heavy chain. The bispecific antibody is selected from the following combinations: the sequence comprising a light chain is Ab2317VL-$(G_4S)_3$-NivoVL-Lc (κ chain), and the sequence comprising a heavy chain is Ab2317VH-$(G_4S)_3$-NivoVH-Hc (hIgG4); or, the sequence comprising the light chain is PemVL-$(G_4S)_3$-Ab2317VL-Lc (κ chain), and the sequence comprising the heavy chain is PemVH-$(G_4S)_3$-Ab2317VH-Hc (hIgG4); or the sequence comprising the light chain is NivoVL-$(G_4S)_3$-

Ab2325VL-Lc (κ chain), and the sequence comprising the heavy chain is NivoVH-(G₄S)₃-Ab2325VH-Hc (hIgG1).

Or the bispecific antibody comprises a first protein functional region and a second protein functional region, wherein one protein functional region is an immunoglobulin, and another protein functional region is a Fab' or a F(ab')₂.

In a preferred embodiment there is provided the first protein functional region is an immunoglobulin and the second protein functional region is a Fab' or a F(ab')₂; or the first protein functional region is a Fab' or a F(ab')₂, and the second protein functional region is an immunoglobulin; the Fab' or F(ab')₂ is linked to the immunoglobulin by a disulfide bond or a linker, the linker is preferably a peptide fragment or (Gly-Gly-Gly-Gly-Ser)ᵥᵥ which can be used as a linker conventional in the art, and the w is preferably an integer between 0 and 10, more preferably 1, 2, 3 or 4; the constant region of the immunoglobulin is preferably a human antibody constant region, and the human antibody constant region preferably comprises a human antibody light chain constant region and a human antibody heavy chain constant region, the human antibody light chain constant region is preferably a κ chain or a λ chain; the heavy chain constant region of the human antibody is preferably a hIgG1, a hIgG2 or a hIgG4. When the light chain and the heavy chain of the Fab' or F(ab')₂ are connected by a linker, the Fab' or F(ab')₂ is no longer Fab' or F(ab')₂ in the strict sense, because of the linker that exist between the light and heavy chains.

In order to solve the technical problems described above, the third technical solution of the present invention is an isolated nucleic acid encoding the LAG-3 binding protein described above, or the bispecific antibody targeting LAG-3 described above.

In order to solve the technical problems described above, the fourth technical solution of the present invention is an expression vector comprising the isolated nucleic acid described above.

In order to solve the technical problems described above, the fifth technical solution of the present invention is a host cell comprising the expression vector described above. Preferably, the host cell is a prokaryotic cell or a eukaryotic cell.

In order to solve the technical problems described above, the sixth technical solution of the present invention is a method for preparing a LAG-3 binding protein or a bispecific antibody targeting LAG-3, which comprises: culturing the host cell described above and obtaining the LAG-3 binding protein or the bispecific antibody targeting LAG-3 from the culture.

In order to solve the technical problems described above, the seventh technical solution of the present invention is an antibody-drug conjugate, which comprises a cytotoxic agent, and the LAG-3 binding protein described in the first technical solution or the bispecific antibody targeting LAG-3 described in the second technical solution.

In order to solve the technical problems described above, the eighth technical solution of the present invention is a pharmaceutical composition comprising the LAG-3 binding protein described above, or the bispecific antibody targeting LAG-3 described above, or the antibody-drug conjugate described above.

In order to solve the technical problems described above, the ninth technical solution of the present invention is a kit combination comprising a kit A and a kit B; the kit A comprises the LAG-3 binding protein described above, or the bispecific antibody targeting LAG-3 described above, or the antibody-drug conjugate described above, or the pharmaceutical composition described above; the kit B comprises other drugs for treating cancer.

In order to solve the technical problems described above, the tenth technical solution of the present invention is a use of the LAG-3 binding protein, the bispecific antibody targeting the LAG-3, the antibody-drug conjugate, the pharmaceutical composition and/or the kit combination in the preparation of a medicament for the treatment and/or prevention of cancer.

Preferably, the cancer is selected from the group consisting of leukemia, lymphoma, ovarian cancer, breast cancer, endometrial cancer, colon cancer, rectal cancer, bladder cancer, urothelial cancer, non-small cell lung cancer, lung adenocarcinoma, lung squamous cell cancer, bronchial cancer, osteocarcinoma, prostate cancer, pancreatic cancer, gastric cancer, hepatocellular carcinoma, gallbladder carcinoma, cholangiocarcinoma, esophageal cancer, renal cell cancer, thyroid cancer, head and neck squamous cell cancer, testicular cancer, endocrine adenocarcinoma, adrenal carcinoma, pituitary cancer, skin cancer, soft tissue cancer, vascular cancer, brain cancer, nerve cancer, retinoblastoma, meningeal carcinoma, oropharyngeal cancer, hypopharyngeal cancer, cervical cancer, metrocarcinoma, glioblastoma, medulloblastoma, astrocytoma, glioma, meningioma, gastrinoma, neuroblastoma, melanoma, myelodysplastic syndrome, and sarcoma.

Thus, the present invention also provides a method of treating cancer using the LAG-3 binding protein, the bispecific antibody targeting LAG-3, the antibody-drug conjugate, the pharmaceutical composition, and/or the kit combination described above to treat the patients with cancers described above.

It should be understood that the terms "first" and "second" of the present invention have no practical meaning, and are merely used to distinguish the same terms. When referring to the number of scFvs or cytokines or cytokine receptors or Fab' or F(ab')₂, "a pair" and "two", "two pairs" and "four" have the same meaning. When referring to the number of light chains or heavy chains or light chain variable regions or heavy chain variable regions, "a" and "one chain", "two" and "two chains" have the same meaning.

In the present invention, the scientific and technical terms used herein have the meanings commonly understood by those skilled in the art, unless otherwise specified. Furthermore, the laboratory procedures of cell culture, molecular genetics, nucleic acid chemistry, and immunology used herein are conventional procedures that are widely used in the corresponding fields. Meanwhile, definitions and explanations of the related terms are provided below for a better understanding of the present invention.

As used herein, the term $EC_{50}$ refers to the concentration for 50% of maximal effect, i.e., the concentration that causes 50% of the maximum effect.

As used herein, the term "antibody" generally refers to an immunoglobulin consisting of two pairs of polypeptide chains [each pair has a light (L) chain and a heavy (H) chain]. In a general sense, the heavy chain can be understood as a polypeptide chain with a larger molecular weight in an antibody, while a light chain refers to a polypeptide chain with a smaller molecular weight in an antibody. Light chains can be classified into κ and λ light chains. Heavy chains can generally be classified into μ, δ, γ, α, or ε, and the isotypes of the antibodies are defined as IgM, IgD, IgG, IgA, and IgE, respectively. In the light and heavy chains, the variable and constant regions are linked by a "J" region of about 12 or more amino acids, and the heavy chains further comprise a "D" region of about 3 or more amino acids. Each heavy chain consists of a heavy chain variable region (VH) and a heavy chain constant region (CH). The heavy chain constant region consists of three domains (CH1, CH2, and CH3). Each light chain consists of a light chain variable region (VL) and a light chain constant region (CL). The light chain constant region consists of a domain CL. The constant region of an antibody can mediate the binding of immunoglobulins to host tissues or factors, including various cells of the immune system (e.g., effector cells) and a first component (C1q) of the classical complement system. The VH and VL regions can also be subdivided into regions of hyper variable regions [named complementarity determining regions (CDRs)], interspersed with more conservative regions named framework regions (FR). Each VH and VL is composed of three CDRs and four FRs arranged from the amino terminal to the carboxy terminal in the following order: FR1, CDR1, FR2, CDR2, FR3, CDR3, FR4. The variable regions (VH and VL) corresponding to each heavy/light chain form the antibody binding site, respectively. Amino acids were assigned to each region or domain according to the definition of Kabat EA. et al., Sequences of Proteins of Immunological Interest [National Institutes of Health, Bethesda, MD. (1987 and 1991)], or Chotheia & Lesk 1987)]. Mol. Biol. 196: 901-917; or the definition of Chothia et al., (1989) Nature 342:877-883. In particular, that heavy chain can also contain more than 3 CDRs, for example 6, 9 or 12 CDRs. For instance, in the bispecific antibody of the present invention, the heavy chain can be the N-terminus of the heavy chain of an IgG antibody linking to the ScFv of another antibody, in this case the heavy chain has 9 CDRs.

As use herein, unless the context clearly dictates otherwise, when referring to the term "antibody", it comprises not only the intact antibody, but also antigen-binding fragments of the antibody. The term "antigen-binding fragment" refers to a polypeptide comprising fragments of a full-length antibody that retains the ability to specifically bind to the same antigen to which the full-length antibody binds and/or competes with the full-length antibody for specific binding to an antigen, which is also named "antigen-binding moiety". See generally Fundamental Immunology, Ch.7, Paul, W., ed., 2nd edition, Raven Press, N.Y (1989), which is incorporated herein by reference in its entirety for all purposes. Antigen-binding fragments of an antibody can be produced by recombinant DNA techniques or by enzymatic or chemical cleavage of an intact antibody. In some cases, antigen-binding fragments comprise Fab, Fab', F(ab')$_2$, Fd, Fv, dAb, and complementarity determining region (CDR) fragments, single-chain binding fragments (e.g., scFv), chimeric antibodies, diabodies, and polypeptides comprising at least a portion of an antibody sufficient to confer specific antigen-binding ability to the polypeptide.

The term "Fv" is intended to refer to an antibody fragment consisting of the VL and VH domains of a single arm of an antibody; the term "Fab" means an antibody fragment consisting of VL, VH, CL and CH1 (or CH) domains; the term "F(ab')$_2$" means an antibody fragment comprising two Fab fragments linked by a disulfide bridge on the hinge region.

In some cases, the antigen-binding fragment of an antibody is a single-chain binding fragment (e.g., scFv), wherein the VL and VH domains form a monovalent molecule through a linker which enable the domains to be produced as a single polypeptide chain [see, e.g., Bird et al., Science 242:423-426 (1988) and Huston et al., Proc. Natl. Acad. Sci. USA 85: 5879-5883 (1988)]. Such scFv molecules can have a general structure: NH$_2$-VL-linker-VH—COOH or NH$_2$—

VH-linker-VL-COOH. Suitable linkers in the prior art consist of repeated G$_4$S (SEQ ID NO: 51) amino acid sequences or variants thereof. For example, a linker having an amino acid sequence of (G$_4$S)$_4$ (SEQ ID NO: 54) or (G$_4$S)$_3$ can be use, as well as the variants thereof.

The antigen-binding fragment of an antibody (e.g., the antibody fragment described above) can be obtained from a given antibody using conventional techniques known to those skilled in the art (e.g., recombinant DNA techniques or enzymatic or chemical cleavage methods) and the antigen-binding fragment of an antibody can be specifically screened in the same manner as for an intact antibody.

As used herein, the term "isolated" refers to one obtained from a natural state by artificial means. If a certain "isolated" substance or component is present in nature, it may be that its natural environment has changed, or the substance may be isolated from the natural environment, or both of them. For example, a certain unisolated polynucleotide or polypeptide naturally exists in a living animal, and the same polynucleotide or polypeptide with high purity isolated from such natural state is called "isolated". The term "isolated" exclude neither the mixing of artificial or synthetic substances, nor the presence of other impurities that do not affect the activity of the substance.

As used herein, the term "host cell" refers to the cells, into which can be used to introduce vectors, including, but not limited to, the prokaryotic cells such as E. coli etc., the fungal cells such as yeast cells etc., the insect cells such as Drosophila S2 cells or Sf9 etc., or the animal cells such as fibroblasts, CHO cells, COS cells, NSO cells, HeLa cells, BHK cells, HEK 293 cells, human cells, etc.

As used herein, the term "KD" refers to the dissociation equilibrium constant (KD) of a specific antibody-antigen interaction, which is used to describe the binding affinity of antibody for antigen. The smaller the equilibrium dissociation constant, the tighter the antibody-antigen binds, and the higher the affinity of antibody for antigen. Generally, the antibody binds to the antigen with a dissociation equilibrium constant of less than about 10$^{-5}$M, such as less than about 10$^{-6}$M, 10$^{-7}$M, 10$^{-8}$M, 10$^{-9}$M, or 10$^{-10}$M or less, e.g., as measured by surface plasmon resonance (SPR) using a BIACORE instrument. For example, the binding affinity of antibody for cell is measured by the KINEXA method using a KINEXA 400 instrument.

On the basis of the common sense in the art, the various preferred conditions described above can be combined arbitrarily to obtain various preferred examples of the present invention.

The reagents and raw materials used in the present invention are commercially available.

The positive and progressive effects of the present invention are:

the LAG-3 binding protein blocks the binding of LAG-3 to MHC II more effectively, thereby relieving signal transduction and antigen presentation between the negatively regulated APC/T cells;

the humanized LAG-3 antibody has good cell functional activity, for example, it can well activate the function and activity of human T cells and human DC cells, and has in vivo efficacy, better PK properties, high expression yield, and thermal stability;

the sequence-specific bispecific antibody (SBody) has good activity, stability, high expression level, a similar structure to a normal IgG antibody, and simple purification process.

DETAILED DESCRIPTION OF THE PREFERRED EMBODIMENT

Figure 1:
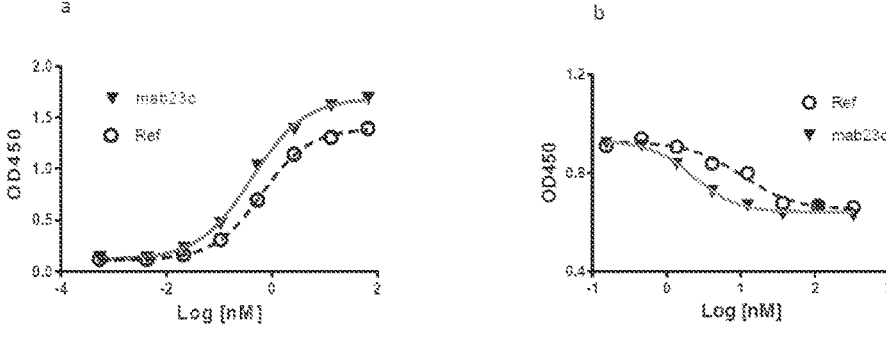
FIG. 1 shows the function and activity of the anti-human LAG-3 antibody mab23c of the present invention: a. the binding activity (ELISA) of mab23c to human LAG-3; b. blocking activity of mab23c against the binding activity of LAG-3 to Daudi cells.

The present invention will be further illustrated by examples described below, which, however, are not intended to limit the scope of the present invention. Experimental methods for which specific conditions are not indicated in the examples of the present invention are usually performed under conventional conditions, such as Using Antibodies: A Laboratory Manual, and Molecular Cloning: A Laboratory Manual, Cold Spring Harbor; or the conditions proposed by the manufacturers of the raw materials or commodities. The reagents without specific sources are commercially available conventional reagents.

Example 1: Cloning, Expression and Purification of Antigens and Antibodies

The antigens used in the present invention were purchased from the following different companies: LAG-3-his (Cat. No.: LA3-H5222) and cyno-LAG-3-mFc (Cat. No.: LA3-C52A0) were purchased from Beijing ACROBiosystems Inc., or LAG-3-his (Cat. No.: 16498-H08H), LAG-3-hFc (Cat. No.: 16498-H05H) and cyno-LAG-3-his (Cat. No.: 90841-C08H) were purchased from Sino Biological Inc., or antigens were expressed and purified by the present invention. The protein sequence of expressed human LAG-3 refers to NCBI Reference Sequence: NP_002277.4, with a full length of 1-525 amino acids, wherein the signal peptide is at positions 1-22; the amino acids of extracellular region (ECD) is at positions 23-422; the first domain and second domain (domain #1 and #2, D12) D12-his and D12-hFc is at positions 23-239 in the extracellular region (ECD). The sequence of murine LAG-3 his tagged (mLAG-3-his) refers to amino acids at positions 23-406 of the extracellular region (ECD) of NCBI gi|148667361|gb|EDK99777.1. The sequence of Macaca LAG-3 his tagged (cynoLAG-3-his) refers to amino acids at positions 23-434 of the extracellular region (ECD) of NCBI No. NP_001271679.1.

The human PD-1 (hFc/his tag) protein sequence refers to NCBI Reference Sequence: NP_005009.2, with a full length of 288 amino acids, wherein the signal peptide is at positions 1-20; ECD is amino acids at positions 21-167.

The human PD-L1 (hFc/his tag) protein sequence refers to NCBI Reference Sequence: NP_054862.1, with a full length of 290 amino acids, wherein the signal peptide is at positions 1-18; the amino acids sequence of ECD is at positions 19-239.

The antibodies used in the present invention, include the positive control antibody Ref (i.e., BMS-986016, sequence from WO2014008218A1, LAG3.5, #12 light chain, #14 heavy chain), PD-1 antibody nivolumab (sequence from WO2013019906), and Pembrolizumab (sequence from www.drugbank.ca, Accession Number: DB09037) were all expressed and purified by the present invention.

The vector used for expression in the present invention is pTT5 (Biovector, Cat. No.: 102762). The expressed recombinant protein and antibody light and heavy chain sequences were cloned into pTT5 vector, and transiently transfected into HEK293E cells (Life Technologies, Cat. No.: 11625019) for expression, and then purified.

Specifically, the 293 cells were expanded in Gibco Free-Style 293 Expression Medium (Gibco, Cat. No.: 12338018). Before starting the transient transfection, the cell concentration was adjusted to 6-8×10⁵ cells/ml and the cells were cultured with the medium containing 1% FBS (Aus Gene X FBS Excellent supplier: AusGeneX, China, Cat. No.: FBSSA500-S) for 24 h in a shaker at 37° C. in 8% $CO_2$. Microscopic examination shows that the survival rate is over 95%, and the cell concentration is 1.2×10⁶ cell/ml.

300 ml cells were prepared, 150 g each of heavy chain plasmid and light chain plasmid were diluted in 15 ml of Opti-MEM (Gibco, Cat. No.: 31985070) (if it is a recombinant protein, the amount of single plasmid is 300 μg), and a 0.22 m filter was used for sterilization. Afterwards, 600 μl of 1 mg/ml PEI (Polysciences Inc., Cat. No.: 23966-2) was diluted in 15 ml Opti-MEM and the mixture was placed for 5 min. Then PEI was slowly added to the plasmid and incubated at room temperature for 10 min. While shaking the culture flask, the mixed solution of plasmid-PEI was slowly added into the culture flask dropwise. The transfected cells were incubated for 5 days in a shaker at 37° C. in 8% $CO_2$, and then the supernatant was collected and purified after centrifuging at 3300 g for 10 min.

Purification of antibodies or -Fc fusion proteins: the samples were centrifuged at high speed to remove impurities, and a gravity column (Sangon Biotech Co., Ltd., Cat. No.: F506606-0001) containing Protein A (Mabselect, GE Healthcare Life Science, Cat. No.: 71-5020-91 AE) was equilibrated with PBS (pH 7.4), and washed with 2-5 column volumes of PBS. The column was loaded with sample and washed with 5-10 column volumes of PBS (Sangon Biotech Co., Ltd., Cat. No.: B548117-0500). The target protein was eluted with 0.1 M acetic acid (pH 3.5), and then adjusted to neutral by Tris-HCl (pH 8.0). The concentration was measured by a microplate reader, and then the target protein was packed and stored for later use.

His Tagged protein purification: The samples were centrifuged at high speed to remove impurities. Equilibration of the nickel column (Ni smart beads 6FF, Changzhou Smart-Lifesciences Co., Ltd., Cat. No.: SA036010): the nickel column was equilibrated with PBS solution (pH 7.4) containing 10 mM imidazole and 0.5 M NaCl, and washed with 2-5 times column volumes of PBS. The sample was loaded onto the column. Rinse for impurity proteins: The column was rinsed with PBS (pH 7.4) containing 10 mM imidazole and 0.5 M NaCl to remove non-specifically bound impurity proteins and the effluent was collected. The target protein was eluted with PBS (pH 7.4) containing 250 mM imidazole and 0.5 M NaCl. Buffer replacement: the eluted target protein was centrifuged in an ultrafiltration tube (Merck Millipore, Cat. No.: UFC500308) at 12000 g for 10 min, and then 1 ml PBS was added. After measuring the concentration, the target protein was packed and stored for later use.

The hFc tag used in the present invention was linked with an IgG1 Fc region at the C-terminus, and the his tag was linked with 6×his at the C-terminus.

Example 2: Construction of Human LAG-3 High-Expressed Cell Strain (hLAG-3+ Cells) and Detection of its Binding Activity (ELISA)

The human LAG-3 high-expressed cell strain used in the present invention is completed by a stable cell strain construction platform of the company. The specific steps are as follows: on the first day of experiment, 293T cells (National Collection of Authenticated Cell Cultures, Cat. No.: GNHu17) were inoculated into two 6 cm petri dishes, and the number of cells in each dish reached $7.5 \times 10^5$. On the second day, 4 µg each of the packaging plasmid (pGag-pol, pVSV-G, etc., BioVector Science Lab) and the plasmid pBabe-hLAG-3 cloned with human LAG-3 gene were added to OPTI-MEM (ThermoFisher Scientific, Cat. No.: 31985070) to make the final volume up to 200 µl. In addition, 200 µl OPTI-MEM was added with 36 µl transfection reagent fectin (Shanghai BasalMedia Technologies Co., Ltd., Cat. No.: F210); The diluted plasmid and diluted transfection reagent fectin were mixed well; next, the mixture was placed at room temperature for 5 min, and then the mixture (200 µl per dish) was dropwise added to the cultured 293T cells. On the third day, culture medium of 293T cell was replaced with 4 ml DMEM high glucose medium (Shanghai BasalMedia Technologies Co., Ltd./BasalMedia Biology, Cat. No.: L130KJ). On the fourth day, CHO-K1 cells (National Collection of Authenticated Cell Cultures, Cat. No.: SCSP-507) were inoculated into a 10 cm petri dish to obtain a cell count of $5 \times 10^5$. On the fifth day, the supernatant (virus) of 293T cells was collected, filtered to the cultured CHO-K1 cells through a 0.45 µm filter membrane, and then 10 µg/ml polybrene (Shanghai Yeasen Biotechnology Co., Ltd., Cat. No.: 40804ES76) was added, after mixing, the cells were placed in an incubator. And 3-4 h later, the culture medium was changed to DMEM/F12 containing 10% FBS (BasalMedia Biology, Cat. No.: L310KJ). The CHO-K1 cells were subcultured on day 7, and the subcultured cells were screened by adding 10 µg/ml puromycin (BasalMedia Biology, Cat. No.: S250J0) on day 8. After 2-3 days, a large number of cells died, the cell culture medium was changed for continuous culture, until no more death cells; the remaining cells were then amplified in a large number; the monoclonal cell strain was screened, expanded, and cryopreserved.

The amino acid sequence NP_002277.4 of human LAG-3 (pBabe-hLAG-3) used in this example has a full length of 1-525 amino acids, wherein the positions 1-22 are signal peptide sequences, i.e., the positions 23-525 are the protein sequences expressed by the CHO-K1 hLAG-3+ cell strain constructed by the present invention.

Detection of HLAG-3+ Cell-Binding Activity (ELISA):

After the human LAG-3 high-expressed monoclonal cell strain obtained from the above example was expanded and cultured, the cells were seeded into 96-well microplate at a density of $1 \times 10^5$ cells/well and the supernatant was removed after incubation overnight at 37° C. in an incubator; thereafter the cells were fixed with 100 µl/well of a fixative solution for immunostaining (Shanghai Beyotime Biotechnology Co., Ltd., Cat. No.: P0098) for half an hour at room temperature. After washing with PBS (BasalMedia Biology, Cat. No.: B320) once, 5% milk was added with 230 µl per well, and the microplate was incubated for 2 hours at 37° C. for blocking, and then was washed three times with PBST. After washing, each well was added with 50 µl sample, the initial concentration of the sample is 10 µg/ml; other samples were 5-fold serially diluted. The microplate was then incubated for 1 hour at 37° C. and washed 5 times with PBST. 50 µl/well of 1:2500 diluted Anti-human HRP (Jackson Immuno Research, Cat. No.: 109-035-003) was added to the microplate and incubated for 1 hour at 37° C. After washing the microplate 5 times with PBST, 50 µl/well TMB (Surmodic, Cat. No.: TTMB-1000-01) was added to the microplate for color development. Finally, 50 µl/well of 1M $H_2SO_4$ was added to stop the reaction. The microplate was then read by a microplate reader (MultiskanGO Thermo, model 511919200), and the data were analyzed using Graphpad prism 5.

Example 3: Binding Assay of Anti-LAG-3 Antibody to LAG-3 Antigen (ELISA)

Recombinant proteins LAG-3-his, LAG-3-D12-his, Cynomolgus LAG-3-His (cyno LAG-3-his), or mLAG-3-his, etc. were diluted to 1 µg/ml, 2 µg/ml (hLAG-3 D12-his), or 5 µg/ml (cyno LAG-3-his) with PBS buffer (pH7.4), and added to a 96-well microplate (Corning, Cat. No.: CLS3590-100EA) at a volume of 50 µl/well, thereafter incubated in an incubator for 2 hours at 37° C. After discarding the liquid, a blocking solution of 5% skimmed milk (Bright skimmed milk powder) diluted with PBS was added at 230 µl per well, followed by incubating at 37° C. for 3 hours or 4° C. overnight (16-18 hours) for blocking. Subsequently, the blocking solution was discarded, and the microplate was washed 5 times with PBST buffer (pH 7.4 PBS containing 0.05% tweeen-20). Then 50 µl/well of the supernatant (containing the antibody to be tested) or a starting concentration of 10 µg/ml of the antibody to be tested, which was diluted 5 times in gradient, was added, followed by incubating the mixture for 1 hour at 37° C. Subsequently, the microplate was washed 5 times with PBST, then 50 µl/well of 1:2500 diluted Anti-mouse or human HRP secondary antibody (Jackson Immuno Research, Cat. No.: 115-035-003 or 109-035-003) was added, and then the mixture was incubated for 1 hour at 37° C. After washing the microplate 5 times with PBST, 50 µl/well TMB chromogenic substrate (KPL, Cat. No.: 52-00-03) was added, and then incubated for 10-15 min at room temperature. Finally, 50 µl/well of 1 M $H_2SO_4$ was added to stop the reaction. The absorbance value at 450 nm was read by MULTISKAN GO microplate reader (ThermoFisher, Cat. No.: 51119200). The clones with high affinity were selected according to the OD value or the $EC_{50}$ value was calculated (for antibodies with known concentrations).

Example 4: Detection of the Blocking Activity of Anti-LAG-3 Antibody Against the Binding of LAG-3 to Daudi Cells The Daudi cell line (ATCC, CCL-213) was expanded and seeded into 96-well microplate at a density of $2 \times 10^5$ cells/well, and then centrifuged at 1600 rpm for 10 min; thereafter the cells were fixed with 100 μl/well of a fixative solution for immunostaining (Shanghai Beyotime Biotechnology Co., Ltd., Cat. No.: P0098) for half an hour at room temperature. After washing with PBS (BasalMedia Biology, Cat. No.: B320) once, 5% milk was added with 230 μl per well, and the microplate was incubated for 2 hours at 37° C. for blocking, then was washed three times with PBST. Next, each well was added with 25 μl of 100 μg/ml 3-fold gradient dilution of the sample to be tested and 25 μl of 2.5 μg/ml bio-LAG3-mFc (Sino Biological Inc., Cat. No.: 16498-H05H). The microplate was then incubated for 1 hour at 37° C. and washed 5 times with PBST. 50 μl/well of 1:1000 diluted streptavidin-tRP secondary antibody (genscript, Cat. No.: M00091) was added to the microplate and incubated for 1 hour at 37° C. After washing the microplate 5 times with PBST, 50 μl/well TMB (Surmodic, Cat. No.: TTMB-1000-01) was added to the microplate for color development, and 50 μl/well 1M $H_2SO_4$ was added to stop the reaction. The microplate was then read by a microplate reader (Multi-skanGO Thermo, model 511919200), and the data were analyzed using Graphpad prism 5.

Example 5: Discovery of Anti-Human LAG-3 Antibody

Human LAG-3 recombinant protein (prepared in example 1) was used as an antigen to immunize mice in the present invention, fusion hybridomas were screened and optimized from millions of hybridoma clones, and a hybridoma cell line with excellent binding activity to hLAG-3 was unexpectedly found. The cell strain was further subcloned and screened to obtain a monoclonal cell strain, and the murine antibody sequence obtained from the monoclonal cell strain was optimized by computer modeling and humanization design screening to obtain a humanized antibody. The humanized antibody also retains good binding activity to hLAG-3, and very unexpectedly, the obtained humanized antibody also shows good functional activity for cells, in vivo efficacy, better PK properties, high expression yield, and thermal stability.

In detail, experimental SJL mice (female, 4 weeks old) were purchased from Beijing Vital River Laboratory Animal Technology Co., Ltd., with animal production license No.: SCXK (Jing) 2016-0011. Upon purchase, these mice were raised in a laboratory environment for 1 week, with daylight/night dark cycle adjustment, at temperature 20-25° C. and humidity 40-60%, and divided into 3 mice/group/cage. The antigen prepared in Example 1 was used for immunization. The adjuvant was Quickantibody-5w (Beijing Biodragon Immunotechnologies Co., Ltd., KX0210041). The ratio of antigen to adjuvant was 1:1. Animals were treated with calf intramuscular injection of 100 μl/10 μg/animal for the first immunization, and 100 μl/10 μg/animal for the second, third, fourth, and fifth immunization, respectively. 3 days before fusion, a dosage of 100 μl/25 μg/animal was injected for booster immunization. Immunization was scheduled on day 0, 14, 28, 46, 58, and 60 (booster immunization). On day 23, 50, and 58, the serum antibody titers of the mice were determined by the ELISA method described in Example 3, and the mice with high antibody titers, which were in the plateau-phase in the serum, were selected for spleen cell fusion. Hybridoma cells obtained by fusing splenic lymphocytes and myeloma cells Sp2/0 cells (ATCC® CRL-8287™) were seeded into a 96-well microplate.

The 96-well microplate seeded with hybridoma cell lines was primarily screened by the ELISA method described in Example 3, and the binding activity of the antibody to human LAG-3 in the secretion supernatant of the hybridoma cell line was detected. Clones which showed good activity were selected, and its supernatant was taken to detect the blocking activity of the secreted antibody against the binding of hLAG-3 to Daudi cells using the method described in Example 4, preferably the clones showing good binding activity and blocking activity were selected. The obtained monoclonal antibody cell line was further subjected to limited dilution, and the partial results are shown in the following table.

TABLE 1

| | | | activity of monoclonal cell screened by hybridoma fusion | | | |
|---|---|---|---|---|---|---|
| No. | Initial clone number | ELISA values | Blocking activity against the binding of hLAG-3 to Daudi cells | Monoclonal cell line number | ELISA values | Blocking activity against the binding of hLAG-3 to Daudi cells |
| 1 | 1F5 | 0.7019 | 1.3325 | terminated[#] | ND[#] | ND |
| 2 | 1D10 | 1.2039 | 1.5526 | terminated | ND | ND |
| 3 | 2E4 | 1.0328 | 1.5597 | terminated | ND | ND |
| 4 | 3D6 | 1.2203 | 1.6268 | terminated | ND | ND |
| 5 | 3D10 | 0.9939 | 1.2308 | terminated | ND | ND |
| 6 | 4G5 | 1.0038 | 1.6605 | terminated | ND | ND |
| 7 | 4H10 | 1.3306 | 1.3658 | terminated | ND | ND |
| 8 | 5B7 | 2.1042 | 1.3369 | terminated | ND | ND |
| 9 | 5E10 | 1.0328 | 1.3015 | terminated | ND | ND |
| 10 | 6F11 | 0.7877 | 1.4273 | terminated | ND | ND |
| 11 | 7E9 | 1.3369 | 1.871 | terminated | ND | ND |
| 12 | 9C3 | 0.9955 | 1.5265 | terminated | ND | ND |
| 13 | 9E5 | 1.3369 | 1.0273 | terminated | ND | ND |
| 14 | 9B7 | 1.0368 | 1.3159 | terminated | ND | ND |
| 15 | 7B9 | 1.6389 | 0.8976 | 7B9G8G3G2F4 | 2.0858 | 0.8292 |

TABLE 1-continued

| | | | Blocking activity against the binding of hLAG-3 to Daudi cells | | | Blocking activity against the binding of hLAG-3 to Daudi cells |
| No. | Initial clone number | ELISA values | | Monoclonal cell line number | ELISA values | |
| --- | --- | --- | --- | --- | --- | --- |
| 16 | 7B9 Subclone | NA## | NA | 7B9G8G3G2C6 | 2.0673 | 0.8422 |
| 17 | 7B9 Subclone | NA | NA | 7B9G8G3G2D6 | 2.0611 | 0.8147 |
| 18 | 7B9 Subclone | NA | NA | 7B9G8G3G2G7 | 2.1817 | 0.8589 |
| 19 | 7B9 Subclone | NA | NA | 7B9G8G3G2G8 | 1.9547 | 0.8903 |
| 20 | 7B9 subclone | NA | NA | 7B9G8G3G2G10 | 2.0684 | 0.8552 |
| 21 | 7B9 Subclone | NA | NA | 7B9G8G3G2C6 | 1.8743 | 0.8416 |
| 22 | 7B9 Subclone | NA | NA | 7B9G8G3G2C7 | 2.0819 | 0.8266 |
| 23 | 7B9 Subclone | NA | NA | 7B9G8G3G2D6 | 1.6973 | 0.8035 |
| 23 | 7B9 Subclone | NA | NA | 7B9G8G3G2C7 | 2.0819 | 0.8266 |
| 24 | 7B9 Subclone | NA | NA | 7B9G8G3G2F8 | 1.6196 | 0.8457 |
| 25 | 7B9 Subclone | NA | NA | 7B9G8G3G2G8 | 1.5982 | 0.8403 |
| 26 | 7B9 Subclone | NA | NA | 7B9G8G3G2C9 | 1.9909 | 0.8554 | terminated, i.e., the clones with poor blocking activity were terminated without subclone screening.
ND: no detection, i.e., no subsequent test was conducted.
NA, not applicable, i.e., the subclone was derived from the parent clone; specifically in this table, the parent clone referred to clone 7B9 of No. 15.

Partial screened data were listed in table 1. These data show that clones with both good binding activity and good blocking activity were initially screened for fusion hybridomas, for example, the clone 7B9 of No. 15 in the table (a higher ELISA value indicates stronger binding activity. A lower value of blocking activity indicates a stronger blocking activity). The Clone 7B9 of No. 15 was subjected to multiple round of limiting dilutions, and after the clones were proliferated 7-10 days after each dilution (subclone), the binding activity and blocking activity of the antibody (supernatant) secreted by each subclone were retested by ELISA. The clones with poor blocking activity in the initial screening were discarded, for example, the samples of No. 1-14 listed in the above table were discarded, and no subsequent subclone and detection were conducted.

After multiple round of limiting dilutions for clone 7B9 with No. 15, it was unexpectedly found that the supernatant secreted by the screened monoclonal cell strain 7B9G8G3G2D6 (No. 23) retained good binding activity and the best blocking activity (the lowest value detected under the same conditions, i.e., 0.8035). The antibody sequence was extracted from the monoclonal cell strain No. 23, the preferred light and heavy chain sequences of the murine anti-human LAG-3 antibody mab23 of the present invention were obtained from the extracted antibody sequences.

Example 6: Extraction, Analysis and Identification of Sequence of the Murine Anti-Human LAG-3 Antibody Mab23

The process of extracting antibody sequences from preferably obtained monoclonal cell lines from hybridomas is a conventional method used by those skilled in the art. Specifically, after the monoclonal cell lines described above were harvested, expanded and cultured, $1\times10^6$ cells were taken to extractRNAusing Trizol (Invitrogen, 15596-018) according to the instructions of the kit. Extracted RNA was reversely transcribed into cDNA using a reverse transcription kit purchased from Sangon Biotech (Shanghai) Co., Ltd., Cat. No.: B532435. PCR amplification was performed using the cDNA obtained by reverse transcription as a template. The amplification products were sequenced to obtain the base/coding sequences of the light and heavy chain variable regions of mab23 antibody, respectively (as shown below). The primers used were described in manual TB326 Rev. C0308 published by Novagen.

The base sequence of the light chain variable region of the murine monoclonal antibody mab23 obtained from the preferred hybridoma cell strain of the present invention (the bolded part is the coding sequence) is as follows:

(SEQ ID NO: 1)
gatgaggacccctgctcagattcttgggatcttgttgctcttgtttccag gtaccagatgtgacattcagatgatccagtctccatcctccttatctgcc tctctgggagaaagagtcagtctcacttgtcgggcaagtcaggacattgg tagtagtttaaactggcttcagcaggaaccagatggaactatcaaacgcc tgatctacgccacatccagtttagattctggtgtccccaaaaggttcagt ggcagtaggtctgggtcagattattctctcaccatcagcagccttgagtc tgaagattttgtagactattactgtctacaatatgttacttctccgctca cgttcggtgctgggaccaagctggagctgaaacgggctgatgctgcacca

-continued actgtatccatcttccaccatccagtgagcagttaacatctggaggtgc ctcagtcgtgtgcttctgaacaactctaccccagagacatcaattccctg The base sequence of the heavy chain variable region of the murine monoclonal antibody mab23 obtained from the preferred hybridoma cell strain of the present invention (the bolded part is the coding sequence) is as follows:

(SEQ ID NO: 2)
gatgaaatggcagctgggtttttctcttcctcctgtcagtaattgcaggt gtccaatcccaggttcaactgcagcagtctgggggctgagctggtgaggcc tggggcttcagtgacgctgtcctgcaaggcttcgggctacacatttactg actatgaaatgcactgggtgaaacagacacctgtgcatggcctggaatgg attggaggtattgatcctgaaactgaaggcattgcctataatcagaagtt caggggcaaggccatactgactgcagacaaatcctccatcacagcctaca tggagctccgcagcctgacatctgaggactctgccgtctattactgtaca aactccaattactacggtggaagggaggcctggtttgcttactggggcca agggactctggtcactgtctctggagccaaaacgacaccccatctgtct atccactggcccctggatctgctgcccaaactaactccatggtgaccctg ggatgcctggtcaagggctatacatagccattactcaaa The amino acid sequences encoded by the base sequences of the light and heavy chain variable regions of the murine monoclonal antibody mab23 obtained from the present invention are SEQ ID NO: 3 and SEQ ID NO: 4 as follows. The amino acid sequence of the light chain variable region of the murine monoclonal antibody mab23 obtained from the preferred hybridoma cell strain of the present invention is as follows:

(SEQ ID NO: 3)
DIQMIQSPSSLSASLGERVSLTCRASQDIGSSLNWLQQEPDGTIKRLIYA

TSSLDSGVPKRFSGSRSGSDYSLTISSLESEDFVDYYCLQYVTSPLTFGA

GTKLELK

The amino acid sequence of the heavy chain variable region of the murine monoclonal antibody mab23 obtained from the preferred hybridoma cell strain of the present invention is as follows:

(SEQ ID NO: 4)
QVQLQQSGAELVRPGASVTLSCKASGYTFTDYEMHWVKQTPVHGLEWIGG

IDPETEGIAYNQKFRGKAILTADKSSITAYMELRSLTSEDSAVYYCTNSN

YYGGREAWFAYWGQGTLVTVSG

The antibody sequences of the light chain variable region and heavy chain variable region described above were recombinantly expressed with the constant regions of different types of IgG, such as human hIgG1, hIgG2, hIgG3, hIgG4, human κ light chain and human λ light chain; and mouse mIgG1, mIgG2, mIgG3, mouse κ light chain and mouse λ light chain, then purified to obtain entire human-mouse chimeric antibody and mouse antibody. Such as constant region of human heavy chain consisting of hIgG4 and human κ light chain, the chimeric antibody mab23c was obtained by the expression and purification method described in example 1; the binding activity of mab23c to hLAG-3 and the blocking activity against the binding of LAG-3 to Daudi cells were detect by the methods described in examples 3 and 4, and compared in parallel with the control antibody (Ref) (see FIG. 1a and FIG. 1b).

The result shows that mab23c of the present invention is different from the control antibody (Ref). $EC_{50}$ and Emax of mab23c detected by ELISA were 0.41 nM and 1.7, respectively, which were better than 0.64 nM and 1.4 of the control antibody (Ref). Particularly unexpectedly, with respect to blocking the binding of LAG3 to Daudi cell, the $IC_{50}$ of mab23c of the present invention was 2.3 nM, which is nearly four-fold better than the $IC_{50}$ (10.5 nM) detected by Ref under the same test conditions (FIG. 1b). The good blocking activity is directly and positively correlated with the pharmacodynamic effect of the molecule as a therapeutic antibody. Therefore, the prominent blocking activity of mab23c enables the antibody of the present invention to have better and higher value as a candidate molecule for drug development.

Example 7: Humanization of Murine Antibody Mab23c of the Present Invention

The antibody mab23c (chimeric antibody) unexpectedly found in the present invention has a strong binding activity to the specific antigen hLAG-3, especially an unexpected blocking activity. It shows that the antibody mab23 can be used for the development of monoclonal antibody drugs for tumor treatment against LAG-3 target, and has better value, such as better efficacy. In order to avoid risks of immunogenicity during drug development, the present invention carried out humanized design and screening as well as sequence optimization of murine antibody mab23c. The specific process is as described below.

There are a variety of different CDR definition methods for antibody in the art, which were summarized in the table below.

TABLE 2

| | | | | | |
|---|---|---|---|---|---|
| summary of different CDR definition methods for antibody in the art * | | | | | |
| Loop | CCG definition | Rabat definition | AbM definition | Chothia definition | Contact definition |
| Light chain CDR1 | L24-L34 | L24-L34 | L24-L34 | L24-L34 | L30-L36 |
| Light chain CDR2 | L50-L56 | L50-L56 | L50-L56 | L50-L56 | L45-L55 |
| Light chain CDR3 | L89-L97 | L89-L97 | L89-L97 | L89-L97 | L89-L96 |
| Heavy chain CDR1 | H26-H35 | H31-H35 | H26-H35 | H26-H32 | H30-H35 |
| Heavy chain CDR2 | H50-H65 | H50-H65 | H50-H58 | H52-H56 | H47-H58 |
| Heavy chain CDR3 | H95-H102 | H95-H102 | H95-H102 | H95-H102 | H93-H101 |

For more information, see website: bioinf.org.uk/abs/#cdrdef.

According to various definition methods listed in the above table, the CDR sequences in variable regions of the murine anti-human hLAG-3 antibody mab23 of the present invention can be labeled/annotated as follows.

TABLE 3

CDR sequences of anti-hLAG-3 antibody mab23 of the
present invention defined by CCG definition

| Antibody | mab23 CDRs |
|---|---|
| Light chain CDR1 | RASQDIGSSLN (SEQ ID NO: 5) |
| Light chain CDR2 | ATSSLDS (SEQ ID NO: 6) |
| Light chain CDR3 | LQYVTSPLT (SEQ ID NO: 7) |
| Heavy chain CDR1 | GYTFTDYEMH (SEQ ID NO: 8) |
| Heavy chain CDR2 | GIDPETEGIAYNQKFRG (SEQ ID NO: 9) |
| Heavy chain CDR3 | SNYYGGREAWFAY (SEQ ID NO: 10) |

TABLE 4

CDR sequence of anti-hLAG-3 antibody mab23 of the
present invention defined by Kabat definition

| Antibody | mab23 CDRs |
|---|---|
| Light chain CDR1 | RASQDIGSSLN (SEQ ID NO: 5) |
| Light chain CDR2 | ATSSLDS (SEQ ID NO: 6) |
| Light chain CDR3 | LQYVTSPLT (SEQ ID NO: 7) |
| Heavy chain CDR1 | DYEMH (SEQ ID NO: 11) |
| Heavy chain CDR2 | GIDPETEGIAYNQKFRG (SEQ ID NO: 9) |
| Heavy chain CDR3 | SNYYGGREAWFAY (SEQ ID NO: 10) |

TABLE 5

CDR sequence of the anti-hLAG-3 antibody mab23 of
the present invention defined by AbM definition

| Antibody | mab23 CDRs |
|---|---|
| Light chain CDR1 | RASQDIGSSLN (SEQ ID NO: 5) |
| Light chain CDR2 | ATSSLDS (SEQ ID NO: 6) |
| Light chain CDR3 | LQYVTSPLT (SEQ ID NO: 7) |
| Heavy chain CDR1 | GYTFTDYEMH (SEQ ID NO: 8) |
| Heavy chain CDR2 | GIDPETEGIA (SEQ ID NO: 12) |
| Heavy chain CDR3 | SNYYGGREAWFAY (SEQ ID NO: 10) |

TABLE 6

CDR sequence of the anti-hLAG-3 antibody mab23 of
the present invention defined by Chothia
definition.

| Antibody | mab23 CDRs |
|---|---|
| Light chain CDR1 | RASQDIGSSLN (SEQ ID NO: 5) |
| Light chain CDR2 | ATSSLDS (SEQ ID NO: 6) |
| Light chain CDR3 | LQYVTSPLT (SEQ ID NO: 7) |
| Heavy chain CDR1 | GYTFTDY (SEQ ID NO: 13) |

TABLE 6-continued

CDR sequence of the anti-hLAG-3 antibody mab23 of
the present invention defined by Chothia
definition.

| Antibody | mab23 CDRs |
|---|---|
| Heavy chain CDR2 | DPETEG (SEQ ID NO: 14) |
| Heavy chain CDR3 | SNYYGGREAWFAY (SEQ ID NO: 10) |

TABLE 7

CDR sequence of the anti-hLAG-3 antibody mab23 of
the present invention defined according to
Contact definition

| Antibody | mab23 CDRs |
|---|---|
| Light chain CDR1 | GSSLNWL (SEQ ID NO: 15) |
| Light chain CDR2 | KRLIYATSSLD (SEQ ID NO: 16) |
| Light chain CDR3 | LQYVTSPL (SEQ ID NO: 17) |
| Heavy chain CDR1 | TDYEMH (SEQ ID NO: 18) |
| Heavy chain CDR2 | WIGGIDPETEGIA (SEQ ID NO: 19) |
| Heavy chain CDR3 | TNSNYYGGREAWFA (SEQ ID NO: 20) |

After the analysis, labeling and definition of CDR sequences of the murine antibody mab23 of the present invention according to the above definitions, the humanization of this antibody was carried out using the methods published in many literatures in the art. The murine antibody sequence was compared with sequences in the human antibody germline database (v-base) to identify the light and heavy chain germlines of human antibodies with high homology. On this basis, computer modeling was performed to simulate the sites in the antibody structure that might affect the binding of antibody to antigen, and back mutations were performed on key sites and combinations thereof to screen out the humanized antibody molecules with optimal activity. Back mutation, also known as reverse mutation, i.e., is a mutation of a specific amino acid residues of the humanized antibody back to the amino acid residues at the corresponding positions of the original antibody.

Specifically, through comparative analysis of sequence homology, it was found that the human antibody germlines having high homology with the light chains of mab23 included IGKV1-16*01, IGKV1-17*01, IGKV1-39*01, IGKV1-NL1*01, IGKV1/OR-2*01, IGKV1/OR-3*01, IGKV1/OR-4*01, IGKV1/OR10-1*01, IGKV1/OR2-1*01, IGKV1/OR2-2*01, etc. With further comparison and analysis, the light chain IGKV1-39*01 of human antibody germline was found to be preferred for humanization of the murine antibody mab23 of the present invention. Sequence alignment revealed that the J gene regions of light chains of mab23 had high homology with J genes of light chains of the human antibody germlines hJK1, hJK2.1, hJK2.2, hJK2.3, hJK2.4, hJK3, hJK4.1, hJK4.2, and hJK5. Further comparison and analysis indicated that hJK4.1 was preferably selected as J region of human antibody germline for humanization of light chains of the murine antibody mab23 for humanization design, screening and sequence optimization.

Through comparative analysis of sequence homology, it was found that the human antibody germlines having high homology with the heavy chains of mab23 included IGHHV1-69*02, IGHHV1-69*04, IGHHV1-69*06, IGHHV1-69*08, IGHHV1-69*09, IGHHV1-69*10, IGHHV1-69*14, IGHHV1-69*17, IGHHV1-18*01, IGHHV1-18*03, etc. With further comparison and analysis, the heavy chain IGHV1-18*01 of human antibody germline was found to be preferred for humanization of the murine antibody mab23 of the present invention. Sequence alignment revealed that the J gene regions of heavy chains of mab23 had high homology with J genes of heavy chains of the human antibody germlines hJh1, hJh2, hJh3.1, hJh3.2, hJh4.1, hJh4.2, hJh4.3, hJh5.2, hJh6.1, hJh6.2, hJh6.3, etc. Further comparison and analysis indicated that hJh4.1 was preferred selected as J region of human antibody germline for humanization of heavy chains of the murine antibody mab23 of the present invention. Based on above selection, humanized design, screening and sequence optimization were carried out.

The CDRs of the murine antibody mab23 (as defined by the above CDR definitions) were grafted to the selected light and heavy chain of human antibody germline, and then recombined with the constant regions of IgG light and heavy chain. Then, based on the three-dimensional structure of the murine antibody, the embedded residues, the residues that directly interacted with the CDRs and the residues that have important impact on the conformation of VL and VH were subjected to back mutation. Those mutations and combinations thereof were screened to see the influence of mutations on activity of those chimeric antibodies. The optimization of chemically unstable amino acid residues in the CDRs resulted in an antibody molecule sequences optimized for structure and activity, thus completing the humanization of the murine antibody of the present invention.

In combination with the specific sequences of mab23, the heavy chain and κ light chain (the sequences are as below) of hIgG4 were taken as examples for illustration.

κ chain of light chain constant region of human antibody: SEQ ID NO: 21; heavy chain constant region of human IgG4: SEQ ID NO: 22.

Preferred sequences of humanized light chain variable region of anti-human LAG-3 antibody mab23 of the present invention are as follows:

```
LG2312: SEQ ID NO: 23; LG2313: SEQ ID NO: 24;
LG2314: SEQ ID NO: 25; LG2315: SEQ ID NO: 26, i.e.
DIQMTQSPSSLSASVGDRVTITCRASQDIGSSLNWLQQKPGKAIKRLIYA

TSSLDSGVPSRFSGSGSGTDYTLTISSLQPEDFATYYCLQYVTSPLTFGG

GTKVEIK

LG2316: SEQ ID NO: 27; LG2317: SEQ ID NO: 28, i.e.
DIQMTQSPSSLSASVGDRVTITCRASQDIGSSLNWYQQKPGKAPKRLIYA

TSSLDSGVPSRFSGSRSGSDFTLTISSLQPEDFATYYCLQYVTSPLTFGG

GTKVEIK

LG2318: SEQ ID NO: 29.
```

Preferred sequences of humanized heavy chain variable region of anti-human LAG-3 antibody mab23 of the present invention are as follows:

```
LG2342: SEQ ID NO: 30, i.e.
QVQLVQSGAEVKKPGASVKVSCKASGYTFTDYEMHWVRQAPGQGLEWMGG

IDPETEGIAYNQKFRGRVTMTTDTSTSTAYMELRSLRSDDTAVYYCARSN

YYGGREAWFAYWGQGTLVTVSS

LG2343: SEQ ID NO: 31, i.e.
QVQLVQSGAEVKKPGASVKVSCKASGYTFTDYEMHWVKQAPGQGLEWIGG

IDPETEGIAYNQKFRGRATLTADKSTSTAYMELRSLRSDDTAVYYCTNSN

YYGGREAWFAYWGQGTLVTVSS

LG2344: SEQ ID NO: 32; LG2345: SEQ ID NO: 33;

LG2346: SEQ ID NO: 34; LG2347: SEQ ID NO: 35;

LG2348: SEQ ID NO: 36; LG2349: SEQ ID NO: 37.
```

The humanized sequences of the light chains of the murine antibody mab23 of the present invention contains different back mutations, and the number of back mutation sites can be 10 or more, preferably 0-10 back mutation sites, as the sequences listed above. Any of these sequences were combined with the sequences of the constant regions of κ chain or λ chain of the light chain constant regions of the human antibody to obtain the light chain sequences of the humanized antibody of the present invention, such as the κ light chain constant region used for the light chain of the present invention, as the sequences listed above. Similarly, the heavy chain variable regions used for the humanization also have different numbers of back mutations, and the number of back mutation sites can be 10 or more, preferably 0-10 back mutation sites, as the sequences of the heavy chain variable regions listed above. These sequences of heavy chain variable regions containing different numbers of back mutations were recombined with the sequences of optional human IgG1, 2, 3 and 4 constant regions to obtain the heavy chains sequences of the humanized antibody of the present invention. For example, the heavy chains of the present invention were illustrated by taking hIgG4 as the constant region sequences as an example.

The light and heavy chain sequences of the humanized antibody of the antibody mab23 of the present invention were partially optimized, and the results of expression level (methods of expression, purification and detection of antibody production are the same as those in Example 1 of the present invention) and activity evaluation (method of ELISA detection is the same as that in Example 3 and method of blocking activity detection is the same as that in Example 5 of the present invention) are shown in the following table.

TABLE 8 partial sequences of the humanized antibody mab23 of the present invention (taking the
human κ light chain constant region and hIgG4 heavy chain constant region as an example)

| Humanized antibody | Light chain | | Heavy chain | | Binding activity to hLAG-3 EC50 (nM) | Blocking activity IC50 (nM) | Expression level (mg/L) |
|---|---|---|---|---|---|---|---|
| | Variable region | Constant region (κ chain) | Variable region | Constant region (hIgG4) | | | |
| mab23c | SEQ ID NO: 3 | SEQ ID NO: 21 | SEQ ID NO: 4 | SEQ ID NO: 22 | 0.166 | 1.55 | 7.6 |
| Ab2311 | LG2312 | | LG2342 | | NB* | ND# | 47 |
| Ab2312 | LG2312 | | LG2343 | | NB | ND | 52 |
| Ab2313 | LG2313 | | LG2343 | | 0.221 | 3.22 | 67.7 |
| Ab2314 | LG2314 | | LG2343 | | 0.237 | 1.22 | 31.8 |
| Ab2315 | LG2315 | | LG2343 | | 0.181 | 2.18 | 57 |
| Ab2316 | LG2316 | | LG2343 | | 0.307 | 1.5 | 40 |
| Ab2317 | LG2317 | | LG2343 | | 0.119 | 1.64 | 100.3 |
| Ab2318 | LG2318 | | LG2343 | | 0.28 | 0.86 | 68 |
| Ab2319 | LG2314 | | LG2344 | | 0.764 | 1.85 | 26.9 |
| Ab2320 | LG2315 | | LG2344 | | 1.01 | 1.32 | 35 |
| Ab2321 | LG2317 | | LG2342 | | NB | ND | 96.8 |
| Ab2322 | LG2317 | | LG2345 | | 0.131 | 2.32 | 75.2 |
| Ab2323 | LG2317 | | LG2346 | | NB | ND | 63.7 |
| Ab2324 | LG2317 | | LG2347 | | NB | ND | 68.6 |
| Ab2325 | LG2317 | | LG2348 | | 0.142 | 1.76 | 64.3 |
| Ab2326 | LG2317 | | LG2349 | | NB | ND | 61.8 |

*NB, no binding. The binding curve showed that a weak binding can only be seen at 100 nM.
ND, no detection. Blocking activity was not detected due to weak binding activity.

The above results show that the above humanized antibody molecules obtained from the murine antibody mab23 sequences of the present invention retain binding activity to hLAG-3, and more preferably, many molecules recover the same binding activity as the murine antibody mab23c, wherein the binding activities of the antibodies Ab2315, Ab2317, Ab2322, Ab2325, etc. are not different from that of mab23c. It means that the preferred humanized antibodies of the present invention retain the binding activity of the original murine antibody. In addition, except the antibodies with very weak binding activity (NB), most humanized antibodies have good blocking activity, which is close to that of mab23c, such as Ab2314, Ab2316, Ab2317, Ab2318, Ab2320, Ab2325, etc.

The amino acid (including constant region) sequences of light and heavy chains of the partial preferred humanized antibody of table 8 are as follows.

Amino acid sequence of humanized Ab2315 antibody is as follows:

Light Chain:

```
                                        (SEQ ID NO: 38)
DIQMTQSPSSLSASVGDRVTITCRASQDIGSSLNWLQQKPGKAIKRLIYA

TSSLDSGVPSRFSGSGSGTDYTLTISSLQPEDFATYYCLQYVTSPLTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

Heavy chain: same as the heavy chain of Ab2317 antibody (SEQ ID NO: 40)

Amino acid sequence of humanized Ab2317 antibody is as follows:

Light Chain:

```
                                        (SEQ ID NO: 39)
DIQMTQSPSSLSASVGDRVTITCRASQDIGSSLNWYQQKPGKAPKRLIYA

TSSLDSGVPSRFSGSRSGSDFTLTISSLQPEDFATYYCLQYVTSPLTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

Heavy Chain:

```
                                        (SEQ ID NO: 40)
QVQLVQSGAEVKKPGASVKVSCKASGYTFTDYEMHWVKQAPGQGLEWIGG

IDPETEGIAYNQKFRGRATLTADKSTSTAYMELRSLRSDDTAVYYCTNSN

YYGGREAWFAYWGQGTLVTVSSASTKGPSVFPLAPCSRSTSESTAALGCL

VKDYFPEPVTVSWNSGALTSGVHTFPAVLQSSGLYSLSSVVTVPSSSLGT

KTYTCNVDHKPSNTKVDKRVESKYGPPCPPCPAPEFLGGPSVFLFPPKPK

DTLMISRTPEVTCVVVDVSQEDPEVQFNWYVDGVEVHNAKTKPREEQFNS

TYRVVSVLTVLHQDWLNGKEYKCKVSNKGLPSSIEKTISKAKGQPREPQV

YTLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSLGK
```

Amino acid sequence of humanized Ab2325 antibody is as follows:

Light chain: same as the light chain of Ab2317 antibody (SEQ ID NO: 39)

Heavy Chain:

(SEQ ID NO: 41)
QVQLVQSGAEVKKPGASVKVSCKASGYTFTDYEMHWVKQAPGQGLEWMGG

IDPETEGIAYNQKFRGRATMTTDTSTSTAYMELRSLRSDDTAVYYCANSN

YYGGREAWFAYWGQGTLVTVSSASTKGPSVFPLAPCSRSTSESTAALGCL

VKDYFPEPVTVSWNSGALTSGVHTFPAVLQSSGLYSLSSVVTVPSSSLGT

KTYTCNVDHKPSNTKVDKRVESKYGPPCPPCPAPEFLGGPSVFLFPPKPK

DTLMISRTPEVTCVVVDVSQEDPEVQFNWYVDGVEVHNAKTKPREEQFNS

TYRVVSVLTVLHQDWLNGKEYKCKVSNKGLPSSIEKTISKAKGQPREPQV

YTLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSLGK

Example 8: Comprehensive Evaluation of Binding Activity of the Preferred Humanized Anti-Human LAG-3 Antibody of the Present Invention To further evaluate binding activity of the humanized antibody to LAG-3 of t he present invention, the above preferred humanized antibody Ab2317 was taken as a n example to evaluate its binding activity to different forms and different species of LAG3. The affinity thereof was evaluated by the Baicore method, and the results are shown in table 9.

The Biacore method is as follows: the affinity of the antibodies of the present invention for human LAG-3 was determined using a Biacore T200, GE Healthcare instrument. First, Protein A (Thermo Pierce, Cat. No.: 21181) was coupled to the biosensor chip CM5 (GE, Cat. No.: BR-1005-30) using pH 7.4 running buffer HBS-EP+(10 mM HEPES, 150 mM NaCl, 3 mM EDTA, and 0.05% P20). The chip was activated with a freshly prepared 50 mM NHS (N-hydroxysuccinimide) and 200 mM EDC (1-ethyl-3-(3-dimethyl-aminopropyl) carbodiimide hydrochloride) followed by injection of 10 µg/ml Protein A prepared with 10 mM NaAC (pH4.0). The concentration of the antibody to be tested was 5 µg/ml, and the concentration gradients of antigen LAG-3-his were 0 nM, 1.875 nM, 3.75 nM, 7.5 nM, 15 nM, and 30 nM, respectively. The flow rate was 30 µl/min, binding time was 180 s, and dissociation time was 300s. After the experiment, the chip was washed for 30 s with 10 mM Glycine-HCl (pH 1.5) at a flow rate of 30 µl/min. The experimental data were fitted with the 1:1 Langmuir model using the software of Biacore T200 evaluation version 3.0 (GE), and the value of affinity KD was obtained.

TABLE 9 comprehensive evaluation of the binding activity ($EC_{50}$, nM) and affinity (Biacore) of the antibody of the present invention

| Antibody number | Binding activity to hLAG-3-his | Binding activity to hLAG-3-hFc | Binding activity to hLAG-3-D12-his | Binding activity to hLAG-3-D12-hFc | Binding activity to Cyno LAG3-hFc | Binding activity to MLAG-3-his | Cell-binding activity to hLAG3+ (nM) | Blocking activity $IC_{50}$ (nM) | Biacore activity (KD, nM) |
|---|---|---|---|---|---|---|---|---|---|
| Ab2317 | 0.16 | 0.25 | 1.71 | 2.59 | 40.2 | No binding | 0.2 | 2.7 | 0.168 |
| Ab2325 | 0.19 | 0.40 | 1.51 | 2.01 | 44.5 | No binding | 0.19 | 3.6 | 0.19 |
| Ref | 0.27 | 0.37 | 1.54 | 2.37 | 35.3 | No binding | 0.22 | 8.2 | 0.18 |

The above results indicate that the preferred humanized preferred murine antibodies of the present invention (Ab2317, Ab2325, etc.) bind well to human LAG-3-his (monomer), human LAG3-hFc (dimer), his forms (monomer) of human LAG-3 extracellular loop 1 and loop 2 (hLAG-3-D12), i.e., hLAG-3-D12-his (monomer) and hLAG-3-D12-hFc (dimer) forms, and hLAG3+ cells.

The results of Bicore assay show that the affinity of Ab2317 and Ab2325 is less than 0.2 nM, which is close to that of the reference.

The outstanding advantage of Ab2317 and Ab2325 compared with the reference positive antibody (Ref) was their good blocking activity (the blocking activity of Ab2317 was at least 2 times stronger than that of Ref in parallel assay comparison, i.e., 2.7 nM vs 8.2 nM), which was consistent with the result that mab23c was superior to Ref in blocking activity (FIG. 1b). Moreover, the above data show that the antibody of the present invention binds to the first and second regions (hLAG-3-D12) of hLAG3, indicating that the blocking activity of the antibody of the present invention is to prevent the binding of the D12 region of hLAG3 to MHCII (daudi cells). It is very difficult to screen out the antibody with such specific blocking activity, especially the blocking activity is very good; it is even more difficult and unpredictable that the blocking activity of the antibody of the present invention was more than 2 times stronger than that of the current clinical molecular (Ref) in the art. This specific blocking activity is related to the efficacy of the antibody in clinical treatment of tumor patients, as better blocking activity is expected to result in better efficacy.

In addition, another unexpected advantage of the antibody of the present invention, such as Ab2317, was the high expression yield, which was over 100 mg/l under the conditions of the present invention, while the expression yield of the control antibody Ref was only up to 60 mg/l under parallel and equivalent conditions. The mean expression yields of Ab2317 were more than 60% higher than that of the control antibody Ref in multiple comparisons. This indicates that the expression yield of the antibody of the present invention is superior to that of the control molecule (the difference in expression yield is sequence-related), which brings advantage for the antibody of the present invention to be used in later process development to increase the yield of antibody.

Figure 2:
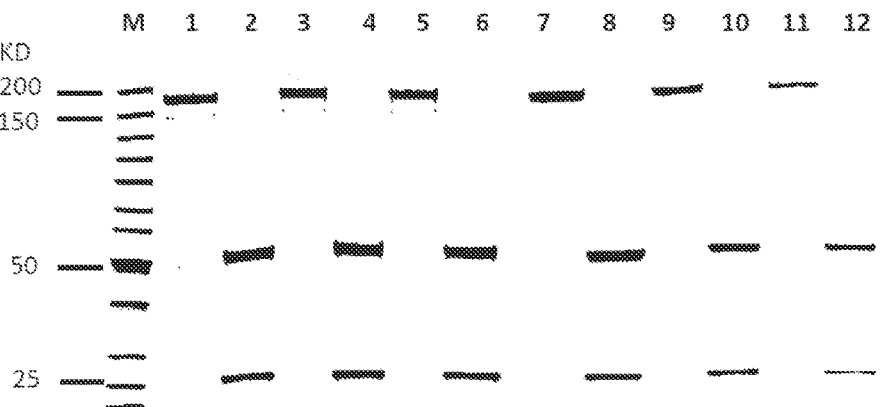
FIG. 2 is a Polyacrylamide Gel Electrophoresis (PAGE) diagram for evaluation of the thermal stability of the humanized anti-human LAG-3 antibody Ab2317 of the present invention.

The antibody Ab2317 of the present invention was prepared into a PBS solution at a concentration of 1 mg/l and stored at 45° C. for 0, 7, and 14 days, and then the stability of the sample was evaluated by gel electrophoresis. The results are shown in FIG. 2. Starting from the left, M is the molecular weight marker. Lane 1, 2; 3, 4; 5, and 6 are the non-denaturation and denaturation electrophoresis of Ab2317 sample stored at 45° C. for 0 day, 7 days and 14 days, respectively. Lane 7, 8; 9, 10; 11, and 12 are the non-denaturation and denaturation electrophoresis of Ref sample stored at 45° C. for 0 day, 7 days and 14 days under parallel condition, respectively. The electrophoresis results showed that the concentration of the antibody Ab2317 of the present invention remained unchanged at 45° C. for 7 days and 14 days whether it was a non-denatured or denatured sample, indicating that there is no degradation. The control sample Ref showed a decrease in amount (less on the gel). For example, the sample at day 14 (lane 11 and 12) was significantly less than that at day 0, indicating there is a significant degradation. This result well illustrates the excellent stability of the antibody Ab2317 of the present invention. This feature brings great convenience and advantages for its development as a drug, especially for formulation development.

The humanized antibodies of the present invention, such as Ab2317, Ab2325, can bind to cynomolgus monkey LAG-3 (cynomolgus, cyno-LAG3-hFc, purchased from Beijing ACROBIOsystems Co., Ltd., Cat. No.: LA3-C5252), which is the same as the control antibody (Ref), with binding activity of 40.2 nM, 44.5 nM, and 35.3 nM, respectively. This binding activity was more than 200 times weaker than that of human LAG-3. This was consistent with the result of using Biacore to detect the affinity of the antibody of the present invention for cyno-LAG3-hFc. The affinity of Ref was 836 nM (more than 4000 times weaker than the affinity of human LAG-3); the binding of Ab2317 and Ab2325 to cyno-LAG-3-hFc was not detectable by Biacore. In addition, the above antibodies also did not bind to mouse LAG-3.

The antibody LG2317 is used as an example of the present invention for the subsequent evaluation of cell function by the following experiments.

Example 9: Evaluation of Functional Activity of Anti-LAG-3 Antibody in Activating Human T Cells On the day of experiment, human PBMC (isolated from peripheral blood donated by healthy volunteers) were collected, and the cells were suspended in RPMI 1640 medium containing 10% FBS and counted; the cell density was adjusted to $1 \times 10^6$ cells/ml, which was then seeded into 96-well plate at 85 μl/well and placed in an incubator. Superantigen (SEB, purchased from Beijing Compro Benin Technology Company.) was prepared using the culture medium to make the initial concentration of 2 μg/ml, and 5 μl superantigen was added to each well (to make a final concentration of 100 ng/ml). Samples to be tested including a negative antibody sample and a control antibody sample were prepared with the culture medium in proportion, and then added to the above-mentioned 96-well plate at 10 μl/well. The concentration of the antibody to be tested in a 100 μl system was formulated to the desired concentration gradient. After the cell culture plate was incubated in an incubator at 37° C. in 5% $CO_2$ for 3 days, the cell culture plate was taken out and centrifuged at 3000 rpm for 10 min, 80 μl of the supernatant was pipetted from each well for detection of human IL-2.

IL-2 ELISA detection was performed according to the instructions of the kit (Shenzhen Neobioscience Biotechnology Co., Ltd., Cat. No.: EHC003.96), and the steps are as follows:

a. Obtained cell culture supernatant was diluted 25 times (Dilution varies with the experiment), and then added to the microplate (100 μl/well). Standards were diluted with universal sample diluent into different concentration gradients: 1000 pg/ml, 500 pg/ml, 250 pg/ml, 125 pg/ml, 62.5 pg/ml, 31.25 pg/ml, 15.625 pg/ml, and 100 μl/well of each gradient was added; universal sample diluent was added as blank.

b. The reaction wells were sealed with parafilm and incubated at 37° C. for 90 min.

c. The microplate was washed 5 times, for 3 min each time; 100 μl of working solution for biotinylated antibody was added into each well, and diluent of biotinylated antibody was added into blank wells; the reaction wells were sealed with new sealing tape and incubated at 37° C. for 60 min.

d. The microplate was washed 5 times, for 3 min each time; 100 μl of working solution for enzyme-binding was added into each well, and diluent of enzyme-binding was added into blank wells; the reaction wells were sealed with new sealing tape and incubated at 37° C. for 30 min without exposure to light.

e. The microplate was washed 5 times, for 3 min each time, and 100 µl of chromogenic substrate TMB was added into each well and incubated at 37° C. for 15 min C in the dark.

f Stop solution was added at 100 µl/well and mixed well, OD450 was read by microplate reader within 3 min.

g. Analysis of result: IL-2 values were calculated, then compared with the blank control and converted into an increase percentage (%) to evaluate the activity of human T cells activated by the samples.

Figure 3:
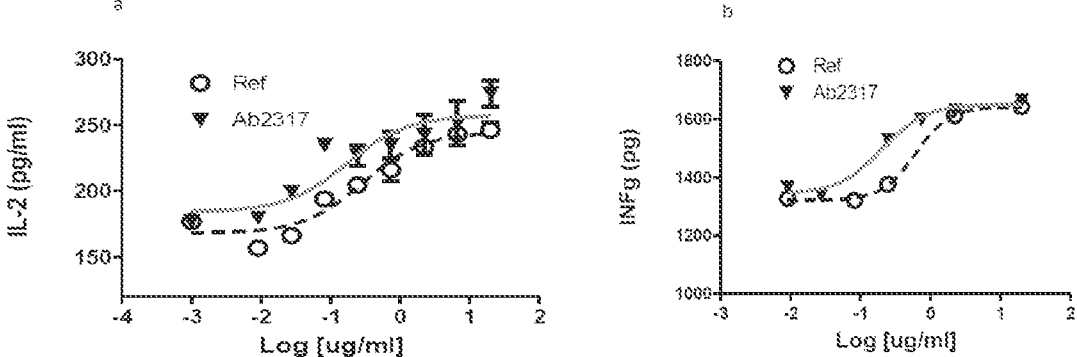
FIG. 3 shows the function and activity of the humanized anti-human LAG-3 antibody Ab2317 of the present invention: a. Ab2317 activates human T cell activity; b. Ab2317 activates human DC cells to stimulate human T cell activity (MLR assay).

The results of different donors T cell experiments all indicate that the preferred antibody Ab2317 of the present invention activates human T cells to release IL-2 with an $EC_{50}$ of 0.34 µg/ml. Under the same conditions, the $EC_{50}$ of the comparative experimental control antibody Ref is 1.4 µg/ml. It means that the activity of the antibody of the present invention on T cells is at least more than 3 times stronger than that of the control Ref FIG. 3a shows one of the representative data.

Example 10: Detection of Activity of the Anti-LAG-3 Antibody of the Present Invention Alone and in Combination with PD-1 Antibody in a Mixed Lymphocyte Reaction (MLR Assay)

The activity of the series of antibodies of the present invention in activating human T cells was evaluated by a method of detecting the secretion of INF-γ (INFg) using mixed lymphocyte reaction (MLR assay). Namely, dendritic cells (DCs) induced from the human blood cell PBMC (isolated from peripheral blood donated by healthy volunteers) isolated in the present invention were used to stimulate T cells from different volunteers. Specifically, dendritic cells were cultured as follows: on the first day of the experiment, RPMI 1640 medium was used to inoculate PBMC with 2 ml per well in a 6-well microplate at a concentration of $1 \times 10^6$ cells/ml, and the microplate was incubated in an incubator at 37° C. in 5% $CO_2$ for 2 hours. Then the suspended cells were gently pipetted out, and 2 ml of complete RPMI 1640 medium (containing 10% FBS, 100 ng/mL of GM-CSF, Peprotech, Cat. No.: 300-03, and 100 ng/mL of IL-4, Peprotech, Cat. No.: 200-04) were added to the adherent cells which were then cultured for 2 days, followed by adding 1 ml of fresh complete RPMI 1640 medium to each well. On the $5^{th}$ day, 3 µl of 100 µg/ml TNF-α (TNF-α was purchased from Peprotech, Cat. No.: AF-300-01A) was added to each well to make a final concentration of 100 ng/ml, and the cells were further cultured for 2 days; the obtained dendritic cells (DCs) were used for the following experiments.

DCs stimulating T cells (MLR) assay: 96-well cell culture plate was coated with 10 ng/ml of anti-CD3 antibody (Miltenyl Biotec, Cat. No.: 130-093-387) at 100 µl/well and incubated at 37° C. for 2 hours, and then washed once with PBS. The cultured DCs were harvested on the $7^{th}$ day and centrifuged, then resuspended in RPMI 1640 medium of 10% FBS and the cells were adjusted to $5 \times 10^4$ cells/ml after counting, followed by adding these cells into the above anti-CD3 coated 96-well plate at 90 µl/well. PBMC cells from different volunteers were counted and adjusted to $5 \times 10^5$ cells/ml, and then added to the above 96-well microplate coated with anti-CD3 and inoculated with DCs at 90 µl/well. Samples to be tested, including the reference antibody (Ref), Ab2317 and PD-1 antibody (obtained by expression and purification in the present invention), were prepared with PBS in proportion, and added to the above 96-well microplate. Ref or Ab2317+PD-1 antibody were added at 10 µl/well. The final concentration of PD-1 antibody in the 200 µl system was 0.5 µg/ml. The concentration of the antibody to be tested (Ref or Ab2317) in the 200 µl system was formulated to the desired concentration gradient. Control group comprised 90 µl PBMC cells, 90 µl DC and 20 µl PBS. After incubating in an incubator at 37° C. in 5% $CO_2$ for 4 days, the cell culture plate was taken out and centrifuged at 3000 rpm for 10 min, and then 150 µl of supernatant was pipetted from each well for the detection of human INF-γ.

IFN-γ was detected by ELISA according to the instructions of the kit (Shanghai Neobioscience Biotechnology Co., Ltd., Cat. No.: EHC102g.96); the steps are as follows:

h. The cell culture supernatant was added to a microplate (100 µl/well); standards were diluted with universal sample diluent into different concentration gradients: 1000 pg/ml, 500 pg/ml, 250 pg/ml, 125 pg/ml, 62.5 pg/ml, 31.25 pg/ml and 15.625 pg/ml, then 100 µl/well of each gradient was added; universal sample diluent was added as blank.

i. The reaction well were sealed with plate sealing tape and incubated at 37° C. for 90 min.

j. The microplate was washed 5 times, for 3 min each time; 100 µl of working solution for biotinylated antibody was added into each well, and diluent of biotinylated antibody was added into blank wells; the reaction wells were sealed with new sealing tape and incubated at 37° C. for 60 min.

k. The microplate was washed 5 times, for 3 min each time; 100 µl of working solution for enzyme-binding was added into each well, and enzyme-binding diluent was added into blank wells; the reaction wells were sealed with new sealing tape and incubated at 37° C. for 30 min in the dark.

l. The microplate was washed 5 times, for 3 min each time, and 100 µl of chromogenic substrate TMB was added into each well and incubated at 37° C. for 15 min C in the dark.

m. Stop solution was added at 100 µl/well and mixed well, OD450 was read by microplate reader within 3 min.

n. Analysis of result: IFN-γ values (pg) were calculated by the formula obtained from standard curve to evaluate the activity of the antibody of the present invention.

The results of FIG. 3b show that the antibody Ab2317 of the present invention activates DCs to stimulate the activity of T-cells (in combination with the PD-1 antibody Keytruda®) with an $EC_{50}$ of 0.21 nM, which is more than 2 times stronger than that of Ref ($EC_{50}$ of 0.61 nM) under the same conditions.

Example 11: Evaluation of In Vivo Efficacy of LAG-3 Antibody of the Present Invention An in vivo efficacy model was established with human PD-1 and LAG-3 double transgenic mice (C57BL/6-hPD1/ hLAG3) to evaluate the in vivo efficacy of LAG-3 antibody of the present invention in animals. The double transgenic mice were purchased from Jiangsu GemPharmatech Co., Ltd., with production license No.: SCXK(SU)2018-0008.

MC38 cells (purchased from Cell Institute of Chinese Academy of Sciences) were cultured in DMEM/high-glucose medium (Shanghai BasalMedia Technologies Co., Ltd., Cat. No.: L110KJ) containing 10% fetal bovine serum (Shanghai BioSun Sci&Tech Co., Ltd., Cat. No.: BS-0002-500) and 1% HEPES (ThermoFisher Scientific, Cat. No.: 15630080), and continuously cultured in an incubator at 37° C. in 5% $CO_2$. C57BL/6-hPD1/hLAG3 female mice, 6 weeks old, 5 mice/cage were fed in an SPF environment at 20-25° C. with humidity 40%-60%; mice were allowed to eat and drink freely, and padding was regularly changed.

When the MC38 cells grew to the logarithmic growth phase (with 80%-90% confluent rate), the cells were digested with 0.25% trypsin and harvested; and then the cells were washed twice with serum-free DMEM/high glucose medium; after that, the cells were resuspended with serum-free DMEM/high glucose medium and counted; Matrigel (BDbiosciences (Shanghai) Co., Ltd., Cat. No.: 354234) and DMEM/high glucose medium were mixed at a ratio of 1:1, and the cell concentration was adjusted to $1 \times 10^7$ cells/ml for inoculation. 100 l of MC38 cell suspension ($10^6$ cells) was inoculated subcutaneously in the right ribs of mice, and the mice with tumor cells growing to the size of about 100-150 $mm^3$ were selected, and then randomly grouped into five mice/group.

The samples to be tested were prepared with PBS and sterilized. PBS was used as blank. PD-1 antibody, which was cloned and expressed according to the published sequences of Keytruda®, was used as a control group for single medication. PD-1 antibody+Ref were used as a control group for the combination medication. PD-1 antibody+Ab2317 were used as a drug group to be tested. The mode of administration was intraperitoneal injection. PD-1 antibody was administered alone or in combination at a dose of 10 µg/100 µl/mouse. In the combination groups, the doses of Ref and Ab2317 were 120 µg/100 µl/mouse with administration frequency of twice per week. The day of injection administration of each sample was recorded as day 0. Body weight and tumor volume were measured and recorded before each administration. The drugs were administered four times in this experiment.

The formula for calculating tumor size is as follows: tumor volume TV ($mm^3$)=0.5×(tumor long diameter×tumor short diameter$^2$); relative tumor growth rate (T/C %)=100%×(T−T0)/(C−C0); tumor inhibition rate (TGI)=(1−T/C)×100%; where T0 and T are the tumor volumes of the sample group at the beginning and the end of the experiment, respectively; C0 and C were the tumor volumes of the control group at the beginning and the end of the experiment, respectively.

Figure 4:
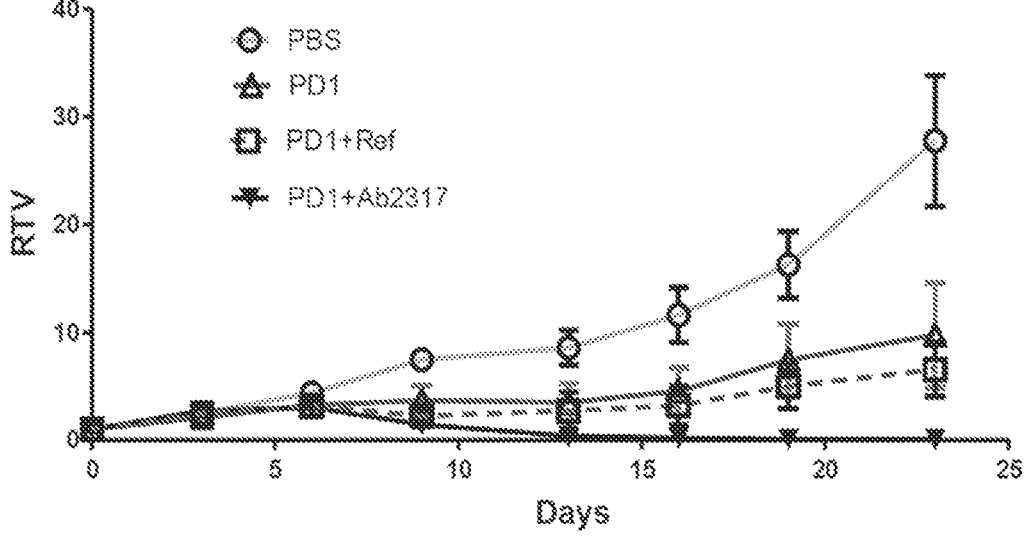
FIG. 4 is an in vivo evaluation of the efficacy of the humanized anti-human LAG-3 antibody Ab2317 of the present invention in animals. RTV in the y-axis is short for relative tumor volume.

The results are shown in FIG. 4 and Table 9b.

TABLE 9b

| | Mean tumor volume ($mm^3$) | | Mean tumor volume ($mm^3$) | | Tumor inhibition | P value | |
|---|---|---|---|---|---|---|---|
| | | | | | | | (vs PD-1 + |
| group | D0 | SD | D23 | SD | rate (%) | (vs PBS) | Ref) |
| PBS | 126.9 | 26.4 | 3551.5 | 1842.7 | — | — | |
| PD-1 | 129.0 | 22.3 | 1296.7 | 1414.7 | 63 | 0.06 | |
| PD-1 + Ref | 132.3 | 25.4 | 823.1 | 847.6 | 80 | 0.01** | |
| PD-1 + Ab2317 | 126.1 | 23.1 | 7.9 | 9.5 | 103 | 0.001** | 0.04* | evaluation of in vivo efficacy of LAG-3 antibody of the present invention

As shown in FIG. 4, when the antibody of the present invention was combined with the PD-1 antibody, the tumor inhibition rate reached 100% on day 13, and the tumor size was reduced comparing with that at the beginning, which maintained to the end of the experiment. These results indicate that the in vivo efficacy of Ab2317+PD-1 group is significantly better than those of the Ref+PD-1 group and PD-1 group.

The statistical results of tumor volumes on day 0 and day 23 were presented in table 9b. The results show that compared with the PBS group on day 23, the efficacy (inhibition rate) of the combination group of PD-1 antibody and Ab2317 antibody of the present invention was 103%, i.e., tumor growth was 100% inhibited and tumor size was reduced comparing with that at the beginning. These results indicate that the in vivo efficacy of Ab2317+PD-1 group is better than that of the antibody PD-1 alone (with an inhibition rate of 63%), and it is also better than that of the combination group of PD-1 antibody+Ref (with an inhibition rate of 80%).

The results of the statistical analysis (T-test) showed that there was no significant difference between the efficacy of PD-1 antibody alone and that of the PBS group (P=0.06). In comparison with the PBS group, the combination group of PD-1 antibody+Ref had a significant difference in efficacy (P=0.01, marked as *). Unexpectedly, there was a highly significant difference between the combined efficacy of PD-1 antibody+Ab2317 antibody of the present invention and the efficacy of the PBS group (P=0.001, marked as **). More unexpectedly, in comparison with the combination group of PD-1 antibody+Ref, the PD-1 antibody+Ab2317 antibody of the present invention had a significant difference in efficacy (P=0.04, significant difference was achieved (P<0.05, marked as *).

During the experiment, there was no significant change in animal body weight in each group, indicating that the antibody of the present invention has no significant toxic effect.

Example 12: Design for Bispecific Antibody Targeting LAG-3

Based on the anti-LAG-3 antibody found above, the present invention carried out a variety of bispecific antibody designs. The general formula of the designed bispecific antibody is as follows.

TABLE 10 design of bispecific antibody based on the anti-LAG-3 antibody of the present invention (formula 1)

| Scheme | Sequences comprising light chains | Sequences comprising heavy chains |
|---|---|---|
| 1 | T2(scFv)$_{n1}$-T1VL-Lc-T2(scFv)$_{n2}$ | T2(scFv)$_{n3}$-T1VH-Hc-T2(scFv)$_{n4}$ |
| 2 | T1(scFv)$_{n1}$-T2VL-Lc-T1(scFv)$_{n2}$ | T1(scFv)$_{n3}$-T2VH-Hc-T1(scFv)$_{n4}$ |
| 3 | T2(scFv)$_{n1}$-T1VL-Lc-T1(scFv)$_{n2}$ | T2(scFv)$_{n3}$-T1VH-Hc-T1(scFv)$_{n4}$ |
| 4 | T1(scFv)$_{n1}$-T2VL-Lc-T2(scFv)$_{n2}$ | T1(scFv)$_{n3}$-T2VH-Hc-T2(scFv)$_{n4}$ |

As shown in table 10 and described herein, a light chain-comprising sequence means that, in addition to the light chain sequence, the sequence can comprise a scFv linked to the light chain sequence; a heavy chain-comprising sequence means that, in addition to the heavy chain sequence, the sequence can comprise a scFv linked to the heavy chain sequence. Wherein T1 represents the first protein functional region for target 1 (such as LAG3), and T2 represents the second protein functional region for target 2 (non-LAG3). T1(scFv) represents scFv sequence of the antibody for target 1; T2(scFv) represents scFv sequence of the antibody for target 2.

In (scFv)$_{n1}$, (scFv)$_{n2}$, (scFv)$_{n3}$, and (scFv)$_{n4}$, n1, n2, n3 and n4 are respectively natural numbers, which can be 0, 1, 2, 3, etc. In the specific embodiment of the present invention, at least one of n1, n2, n3, and n4 is 1, and the rest are 0. VL represents the sequence of the light chain variable region of the antibody for target 1 or 2; VH represents the sequence of the heavy chain variable region of the antibody for target 1 or 2. Lc represents the sequence of the light chain constant region (κ or λ), preferably the sequence of constant region of human light chain; Hc represents heavy chains, including the sequence of constant region of IgG1, IgG2, IgG3 or IgG4, etc. (abbreviated as Hc-IgG1, Hc-IgG2, Hc-IgG3, Hc-IgG4), preferably the sequence of human heavy chain constant region (Hc-hIgG). When the C-terminus of the heavy chain constant region is linked to scFv or other protein sequences, the last amino acid K at C-terminus can be mutated, preferably mutated to A. Thus, in scheme 1, T1 is an immunoglobulin and T2 is a scFv; in scheme 2, T2 is an immunoglobulin and T1 are scFvs; the scFvs target the same target; in schemes 3 and 4, the scFvs at both ends target two different targets.

When the scFv described in table 10 is light chain variable region-linker-heavy chain variable region, the N-terminus of the light chain variable region or the C-terminus of the heavy chain variable region is correspondingly linked to the C-terminus or N-terminus of the light and/or heavy chain of immunoglobulin by a linker; or the scFv is heavy chain variable region-linker-light chain variable region, the N-terminus of the heavy chain variable region or the C-terminus of the light chain variable region is correspondingly linked to the C-terminus or N-terminus of the light and/or heavy chain of immunoglobulin by a linker.

It should be noted that when the scFv described above is a light chain variable region-linker-heavy chain variable region, the connection thereof is that the C-terminus of the light chain variable region is linked with a linker, and the linker is further linked with the N-terminus of the heavy chain variable region, thus, the N-terminus of the scFv light chain variable region and the C-terminus of the heavy chain variable region are exposed, so that the scFv can be linked to the light chain and/or the heavy chain of the immunoglobulin by a linker. In the present invention, when the scFv is linked to the light chain of immunoglobulin, in some specific embodiments, the C-terminus of the heavy chain variable region of the scFv is preferably connected to the N-terminus of the immunoglobulin heavy chain by a linker; when the scFv is linked to the heavy chain of immunoglobulin, in some specific embodiments there is provided, the N-terminus of the light chain variable region of the scFv is preferably linked to the C-terminus of the immunoglobulin heavy chain.

When the scFv is heavy chain variable region-linker-light chain variable region, the connection thereof is that the N-terminus of the light chain variable region is linked to a linker, and the linker is further linked to the C-terminus of the heavy chain variable region, thus, the C-terminus of the scFv light chain variable region and the N-terminus of the heavy chain variable region are exposed, so that the scFv light chain variable region can be connected to the light chain and/or the heavy chain of the immunoglobulin by a linker. In this case, when the scFv is linked to the light chain of immunoglobulin, in some specific embodiments, the C-terminus of the light chain variable region of the scFv is preferably linked to the N-terminus of the immunoglobulin heavy chain; when the scFv is linked to the heavy chain of immunoglobulin, in some specific embodiments, the N-terminus of the heavy chain variable region of the scFv is preferably linked to the C-terminus of the immunoglobulin heavy chain.

The linker is (Gly-Gly-Gly-Ser)$_w$ [abbreviated as (G$_4$S)$_w$], wherein the w is preferably an integer between 0 and 10. Preferably, the linker is (G$_4$S)$_3$, and/or the number of the scFv is one pair, the two svFv are symmetrically linked to light and/or heavy chains of the immunoglobulin.

In addition, the antibody of the present invention can also be in a different form from general formula 1, for example, the following general formula 2.

TABLE 11 design of bispecific antibodies in DVD form based on the anti-LAG3 antibody of the present invention (formula 2)

| Light chain-comprising sequence | Heavy chain-comprising sequence |
|---|---|
| T2VL-linker-T1VL-Lc | T2VH-linker-T1VH-Hc |
| T1VL-linker-T2VL-Lc | T1VH-linker-T2VH-Hc |

In table 11, T1 and T2 represent targets 1 (e.g., LAG3) and target 2 (non-LAG3), respectively. A light chain-comprising sequence means that, in addition to the normally complete light chain sequence, the sequence can comprise another light chain variable region sequence; a heavy chain-comprising sequence means that, in addition to the normally complete heavy chain sequence, the sequence can comprise another heavy chain variable region sequence. The light chain variable region is linked to the complete light chain, and the heavy chain variable region is linked to the complete heavy chain by a linker.

The antibody sequences of each target involved in the above bispecific design, in addition to the anti-LAG3 antibody sequence of the present invention, the PD1 antibody sequence comprises currently published antibody sequences, including anti-PD-1 antibody Nivolumab/Opdivo® (abbreviated as Nivo) and Pembrolizumab/Keytruda® (abbreviated as Pem). In addition to the sequences disclosed in the patents, sequences such as Nivolumab (Nivo) and Pembrolizumab (Pem) can also be found from the public resources such as drugbank.ca, etc. The expression number and sequences of these individual antibodies are shown in the table below.

TABLE 12 numbers, light and heavy chain sequences, and description of the monoclonal antibodies cloned in the present invention

| Number | Light chain sequence | Heavy chain sequence | Description |
|---|---|---|---|
| L101 | NivoVL-Lc (κ chain) | NivoVH-Hc (hIgG4) | Namely Nivolumab or Nivo |
| L105 | PemVL-Lc (κ chain) | PemVH-Hc (hIgG4) | Namely Pembrolizumab or Pem |
| Ab835 | Ab835VL-Lc (κ chain) | Ab835VH-Hc (hIgG4) | The Ab835 sequence of the application No. 201810917684.X, SEQ ID NO: 58 (light chain), SEQ ID NO: 59 (heavy chain) |

The sequences of Nivolumab and Pembrolizumab are available from public information, such as www.drugbank.ca, etc., their sequences are numbered as follows:

NivoVL-Lc (κ chain): SEQ ID NO: 42; NivoVH-Hc (hIgG4): SEQ ID NO: 43;

PemVL-Lc (κ chain): SEQ ID NO: 44; PemVH-Hc (hIgG4): SEQ ID NO: 45;

Ab835VL is SEQ ID NO: 58 of the Application No. 201810917684.X; Ab385VH is SEQ ID NO: 59 of the application No. 201810917684.X.

Example 13: Design and Activity Evaluation of Bispecific Antibody for Dual Targets LAG-3 and PD-1

In the present invention, bispecific antibodies with different sequence structures were designed for dual targets LAG-3 and PD1, the sequences are shown in the table below.

TABLE 13 bispecific antibodies designed for dual targets LAG-3 and PD1

| Antibody number | Light chain sequence | Heavy chain sequence |
|---|---|---|
| LB2373 | NivoVL-Lc (κ chain*) | Ab2317VL-(G$_4$S)$_3$-Ab2317VH-(G$_4$S)$_3$-NivoVH-Hc (hIgG4) |
| LB2374 | NivoVL-Lc (κ chain) | NivoVH-Hc (hIgG4)$^\#$-(G$_4$S)$_3$-Ab2317VH-(G$_4$S)$_3$-Ab2317VL |
| LB2379 | AB2317VL-(G$_4$S)$_3$-AB2317VH-(G$_4$S)$_3$-NivoVL-Lc (κ chain) | NivoVH-Hc (hIgG4) |
| LB2380 | NivoVL-Lc (κ chain)-(G$_4$S)$_3$-AB2317VH-(G$_4$S)$_3$-AB2317VL | NivoVH-Hc (hIgG4) |
| LB2371 | PemVL-Lc (κ chain) | Ab2317VL-(G$_4$S)$_3$-Ab2317VH-(G$_4$S)$_3$-PemVH-Hc (hIgG4) |
| LB2372 | PemVL-Lc (κ chain) | PemVH-Hc (hIgG4)-(G$_4$S)$_3$-Ab2317VH-(G$_4$S)$_3$-Ab2317VL |
| LB2381 | Ab2317VL-(G$_4$S)$_3$-AB2317VH-(G$_4$S)$_3$-pemVL-Lc (κ chain) | PemVH-Hc (hIgG4) |
| LB2382 | PemVL-Lc (κ chain)-(G$_4$S)$_3$-AB2317VH-(G$_4$S)$_3$-AB2317VL | PemVH-Hc (hIgG4) |
| LB2383 | PemVL-Lc (κ chain) | Ab2325VL-(G$_4$S)$_3$-Ab2325VH-(G$_4$S)$_3$-PemVH-Hc (hIgG4) |
| LB2384 | PemVL-Lc (κ chain) | PemVH-Hc (hIgG4)-(G$_4$S)$_3$-Ab2325VH-(G$_4$S)$_3$-Ab2325VL |
| LB211 | NivoVL-Lc (κ chain) | Ab835VL-(G$_4$S)$_3$-Ab835VH-(G$_4$S)$_3$-NivoVH-Hc (hIgG4) |
| LB152 | PemVL-Lc (κ chain) | Ab835VL-(G$_4$S)$_3$-Ab835VH-(G$_4$S)$_3$-PemVH-Hc (hIgG4) |
| LB234 | NivoVL-L (κ chain) | NivoVH-Hc (hIgG4)-(G$_4$S)$_3$-Ab835VH-(G$_4$S)$_3$-Ab835VL |
| LB203 | PemVL-Lc (κ chain) | PemVH-Hc (hIgG4)-(G$_4$S)$_3$-Ab835VH-(G$_4$S)$_3$-Ab835VL |
| LB202 | AB835VL-(G$_4$S)$_3$-AB835VH-(G$_4$S)$_3$-NivoVL-Lc (κ chain) | NivoVH-Hc (hIgG4) |
| LB201 | AB835VL-(G$_4$S)$_3$-AB835VH-(G$_4$S)$_3$-PemVL-Lc (κ chain) | PemVH-Hc (hIgG4) |

41

TABLE 13-continued bispecific antibodies designed for dual targets LAG-3 and PD1

| Antibody number | Light chain sequence | Heavy chain sequence |
|---|---|---|
| LB214 | NivoVL-Lc (κ chain)-(G₄S)₃-Ab835VH-(G₄S)₃-Ab835VL | NivoVH-Hc (hIgG4) |
| LB216 | PemVL-Lc (κ chain)-(G₄S)₃-Ab835VH-(G₄S)₃-Ab835VL | PemVH-Hc (hIgG4) |

*the κ chain means that the light chain is the κ light chain constant region of human IgG.
when the C-terminus of IgG4 was connected to a linker, the last amino acid K at C-terminus was mutated to A.
In the application of the present invention, when the SBody of the present invention was designed by introducing scFv into the C-terminus of the heavy chain, the last amino acid K at C-terminus was mutated to A.

According to the cloning, expression and purification method of the present invention, the bispecific antibody described above were cloned, expressed and purified accordingly, and the binding activities of these designed bispecific molecules to human LAG-3 and PD-1 were detected using the methods of the foregoing examples, respectively, and the results are shown in the following table.

TABLE 14 evaluation of binding activity of bispecific antibodies designed for dual targets LAG-3 and PD-1

| Antibody number | Binding activity to human LAG-3 | | Binding activity to human PD-1 | |
|---|---|---|---|---|
| | EC₅₀, nM | Multiple of EC₅₀ variation * | EC₅₀, nM | Multiple of EC₅₀ variation * |
| LB2373 | 0.546 (0.287 #) | 1.9 | 0.327 (0.112) | 2.92 |
| LB2374 | 1.09 (0.579) | 1.88 | 0.144 (0.108) | 1.33 |
| LB2379 | 0.336 (0.579) | 0.58 | 0.146 (0.108) | 1.35 |
| LB2380 | 1.01 (0.579) | 1.74 | 0.127 (0.108) | 1.18 |
| LB2371 | 0.179 (0.287) | 0.62 | 0.128 (0.13) | 0.98 |
| LB2372 | 0.641 (0.287) | 2.23 | 0.208 (0.13) | 1.6 |
| LB2381 | 0.79 (0.44) | 1.8 | 0.332 (0.23) | 1.44 |
| LB2382 | 0.951 (0.44) | 2.16 | 0.309 (0.23) | 1.34 |
| LB2383 | 0.237 (0.312) | 0.76 | 0.138 (0.13) | 1.06 |
| LB2384 | 0.724 (0.312) | 2.32 | 0.242 (0.13) | 1.86 |
| LB211 | 0.295 (0.254) | 1.16 | 0.292 (0.052) | 5.62 |
| LB152 | 0.443 (0.081) | 5.47 | 0.162 (0.05) | 3.24 |
| LB234 | 17.5 (0.1) | 175 | 0.082 (0.028) | 2.93 |
| LB203 | 0.954 (0.169) | 5.64 | 0.162 (0.085) | 1.91 |
| LB202 | 0.401 (0.254) | 1.58 | 0.361 (0.052) | 6.94 |
| LB201 | 0.529 (0.254) | 2.08 | 0.511 (0.135) | 3.79 |
| LB214 | 0.457 (0.254) | 1.8 | 0.188 (0.052) | 3.62 |
| LB216 | 2.09 (0.254) | 8.23 | 0.412 (0.135) | 3.05 |

The values in brackets refer to the binding activity EC50 of the monoclonal antibodies to the corresponding target under the same experimental conditions.
* The ratio of the binding activity EC50 of the bispecific antibody to the corresponding monoclonal antibody under the same experimental conditions. The larger the ratio, the weaker the affinity of the designed bispecific antibody for a single target. For example, a ratio of 2, which indicates that the designed bispecific antibody weakens the binding activity to the target by 1 time compared with the corresponding monoclonal antibody. The ratio within 2 (experimental error range) indicates that the binding activity is not affected.

Figures 5A, 5B:
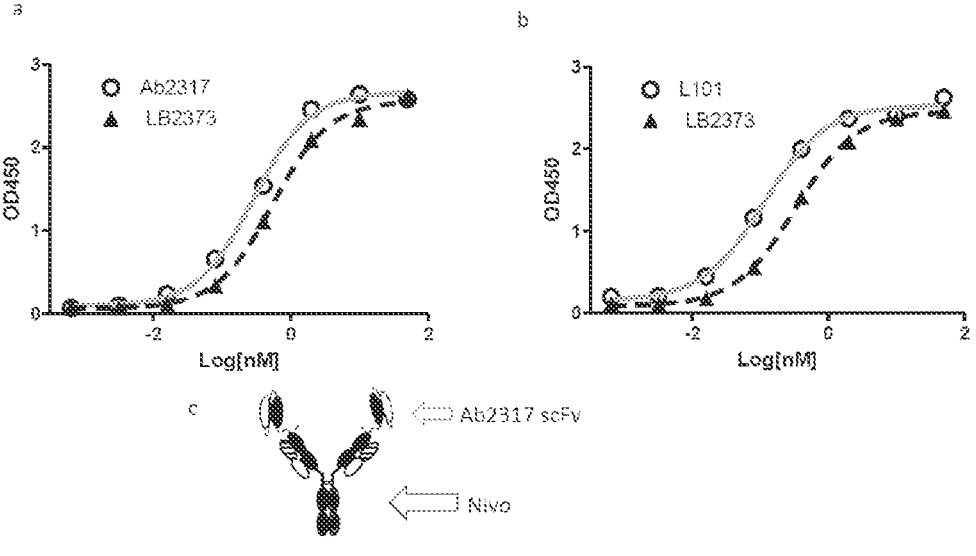
FIG. 5A is a diagram showing the structure and related test data of the bispecific antibody (SBody) LB2373 of the present invention, including a structural diagram (c), the detection result of the binding activity to the human LAG-3 (a) and the detection result of the binding activity to human PD-1 (b).
FIG. 5B is a diagram showing the structure and related test data of the bispecific antibody (SBody) LB2374 of the present invention, including a structural diagram (c), the detection result of the binding activity to human LAG-3 (a) and the detection result of the binding activity to human PD-1 (b).
Figure 5C:
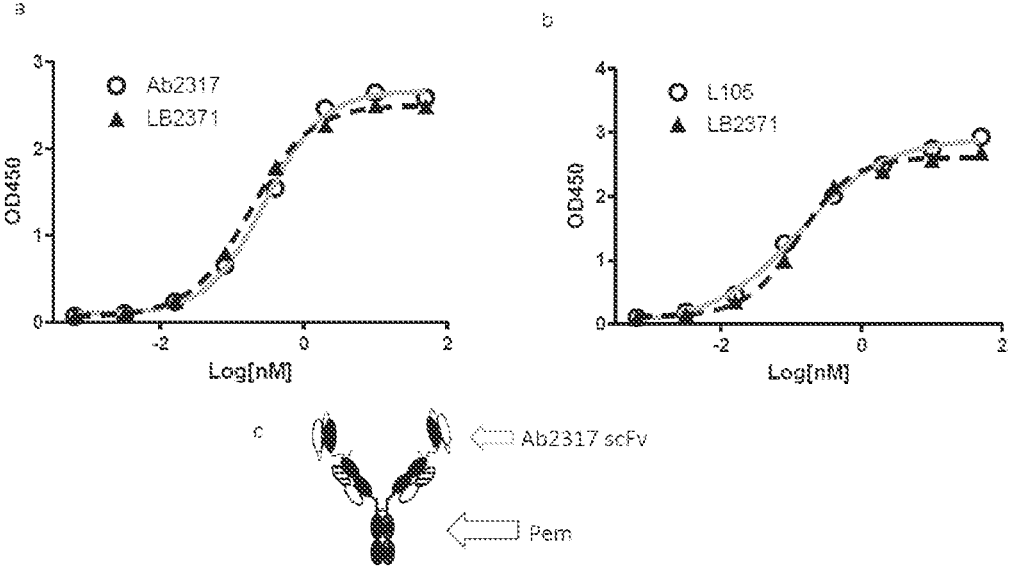
FIG. 5C is a diagram showing the structure and related test data of the bispecific antibody (SBody) LB2371 of the present invention, including a structural diagram (c), the detection result of the binding activity to human LAG-3 (a) and the detection result of the binding activity to human PD-1 (b).
Figure 5D:
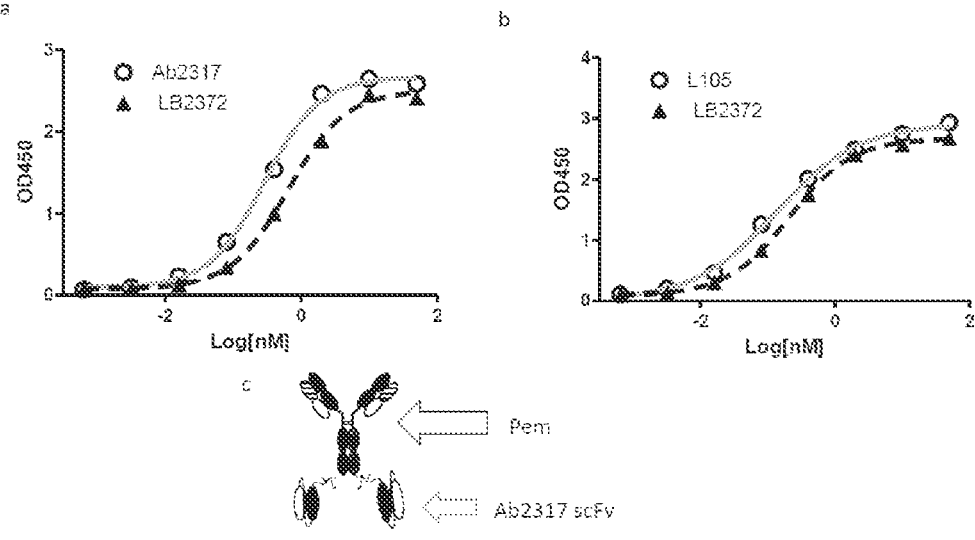
FIG. 5D is a diagram showing the structure and related test data of the bispecific antibody (SBody) LB2372 of the present invention, including a structural diagram (c), the detection result of the binding activity to human LAG-3 (a) and the detection result of the binding activity to human PD-1 (b).

The results in the above table show that by comparing the binding activity of LB2373 with LB2371, both bispecific antibodies have same Ab2317 scFv sequence of the present invention and different PD-1 antibody sequences, and were designed with same structure (scFvs are all at the N-terminus of the heavy chains of PD-1 antibody), it was found that LB2373 has a great influence on the binding activity of PD-1 (the multiple of EC₅₀ variation is 2.92, as shown in FIGS. 5A and 5C), but basically has no effect on the binding activity to LAG3, while there is no effect of LB2371 on the binding activity to either PD-1 or LAG3 (FIG. 5C). The comparison of binding activity between LB2373 and LB2374 as well as the comparison of binding activity between LB2371 and LB2372 revealed (see FIG. 5A, 5B, 5C, and 5D) that bispecific antibodies designed with the same Ab2317 scFv sequence and the same PD-1 antibody sequence have different binding activity to PD-1 and LAG3 due to different positions of Ab2317 scFv (at N-terminus or C-terminus). The binding activity of LB2371 to dual targets is the best. The comparison of binding activity between LB2383 and LB2384 demonstrated the binding activity of LB2383 with Ab2325 scFv at N-terminus of heavy chain of Nivo is better than that of LB2384 with Ab2325 scFv at C-terminus of heavy chain of Nivo.

By comparing the activities of LB2371-LB2374 with those of LB211, LB152, LB234 and LB203, it was found that under the premise of different scFvs of LAG-3 antibody (Ab2317 scFv vs. Ab835 scFv), and same structure (N-terminal or C-terminal of heavy chain) of the same PD-1 antibody (Nivo or Pem), the SBody designed with Ab2317 scFv has much better binding activity than that designed with Ab835 scFv. Especially unexpected, LB2374 and LB234 were designed with same SBody as well as the PD-1 antibody sequence (Nivo) is also the same, only Ab2317 scFv is different from Ab835 scFv. As a result, LB2317 almost well retains its binding activity to LAG-3 and PD-1, while LB234 almost loses its binding activity to LAG-3 (weakened by 175 times). According to these data, it was very unexpectedly found that the binding activity of the SBody designed with the antibody Ab2317 scFv of the present invention is sequence specific.

Comparing the binding activities of LB2379-LB2382 with those of LB202, LB201, LB214 and LB216 against dual targets (PD-1 and LAG-3) in the same structure with different LAG-3 antibody sequences (scFv), the binding activities of LB2379-LB2382 are superior to those of the corresponding LB202, LB201, LB214, and LB216.

These molecular designs exhibit unexpected differences in binding activity based on sequence specificity, and their molecular structure is similar to that of conventional IgG, therefore, the present invention refers to this as the Sequence-based IgG like bispecific antibody format (SBody), i.e., bispecific antibody with a similar structure to the sequence-specific IgG.

The affinity of the bispecific antibody of the present invention was analyzed using Biacore (the same method as described in example 8) represented by LB2374. The affinity of LB2374 for LAG-3 is as follows: ka(1/Ms)=2.21E+6; kd(1/s)=4.13E-4; KD(M)=1.87E-10 (very close to the affinity (1.68E-10) of Ab2317 in Table 9). Affinity of LB2374 for PD-1 is: ka(1/Ms)=2.098E+5; kd(1/s)=1.41E-3; KD(M)= 6.71E-9 (close to the affinity of 8.59E-9 measured with Nivo alone). These data indicate that the bispecific antibody LB2374 of the present invention retains the same affinity (KD) for the dual targets.

In order to evaluate the simultaneous binding activity of the bispecific antibody (SBody) designed by the present invention to dual targets, the activities of LB2374 and LB2371 were evaluated by using a double-sandwich ELISA.

Specifically, PD-1 (expressed by the present invention) was diluted to a concentration of 1 μg/ml with PBS buffer (pH7.4) and added to a 96-well microplate (Corning, Cat. No.: CLS3590-100EA) at a volume of 50 μl/well, thereby incubating in an incubator at 37° C. for 2 hours. After discarding the liquid, a blocking solution of 5% skimmed milk (Shanghai Sangon Biotech Co., Ltd., Cat. No.: A600669-0250) diluted with PBS was added at 200 μl/well, followed by incubating at 4° C. overnight (16-18 hours) for blocking. Subsequently, the blocking solution was discarded, and the microplate was washed 5 times with PBST buffer (pH 7.4 PBS containing 0.05% tweeen-20). Then 50 µl/well of the bispecific antibody to be tested (10 µg/ml) was added and the plate was serially diluted 5 times with 1% BSA, followed by incubating the mixture at 37° C. for 1 hour, the microplate was washed 5 times with PBST. And then 50 µl/well of Bio-LAG3-his (1 g/ml, ACROBio systems, Cat. No.: TM-H5229, biotin-labeled) was added, thereby incubating at 37° C. for 1 hour. Subsequently, the microplate was washed 5 times with PBST, and then 50 µl/well of 1:1000 diluted streptavidin-HRP secondary antibody (GenScript (Nanjing) Co., Ltd., Cat. No.: M00091) was added, followed by incubating at 37 C for 1 hour. After the microplate was washed 5 times with PBST, 50 µl/well TMB chromogenic substrate (KPL, Cat. No.: 52-00-03) was added, and then the microplate was incubated at room temperature for 5-10 min. Finally, 50 µl/well of 1M $H_2SO_4$ was added to stop the reaction. The absorbance value was read by MULTISKAN GO microplate reader (ThermoFisher, Cat. No.: 51119200) at 450 nm, and $EC_{50}$ was calculated based on the OD value.

LAG3-his was diluted to a concentration of 1 µg/ml with PBS buffer (pH7.4) and added to a 96-well microplate at a volume of 50 µl/well, thereby incubating in an incubator at 37° C. for 2 hours. After discarding the liquid, a blocking solution of 5% skimmed milk diluted with PBS was added at 200 µl/well and the mixture was incubated at 4° C. overnight (16-18 hours) for blocking. Subsequently, the blocking solution was discarded, and the microplate was washed 5 times with PBST buffer (pH 7.4 PBS containing 0.05% tweeen-20). Then 50 l/well of the bispecific antibody to be tested (10 µg/ml) was added and the plate was serially diluted 5 times with 1% BSA, followed by incubating the mixture at 37° C. for 1 hour, the microplate was washed 5 times with PBST. And then 50 µl/well of Bio-PD-1-his (10 µg/ml, expression by the present invention, biotin-labeled) was added, thereby incubating at 37° C. for 1 hour. Subsequently, the microplate was washed 5 times with PBST, and then 50 µl/well of 1:1000 diluted streptavidin-TRP secondary antibody was added, followed by incubating at 37 C for 1 hour. After the microplate was washed 5 times with PBST, 50 µl/well TMB chromogenic substrate was added, and then incubated at room temperature for 5-10 min. Finally, 50 µl/well of 1M $H_2SO_4$ was added to stop the reaction. The absorbance value was read by MULTISKAN GO microplate reader at 450 nm, and $EC_{50}$ was calculated based on the OD value.

Results are presented in the table below.

TABLE 14a double-sandwich ELISA of bispecific antibody designed for dual targets LAG-3 and PD-1

| Antibody number | Microplate was coated with PD-1 and LAG-3 was measured, nM | Microplate was coated with LAG-3 and PD-1 was measured, nM |
| --- | --- | --- |
| LB2373 | 1.77 | 16.8 |
| LB2374 | 0.775 | 11.9 |
| LB2372 | 1.75 | 12.0 |
| LB2371 | 1.09 | 14.5 |

The above results show that after binding one of the dual targets, the bispecific antibody (SBody) of the present invention can further bind another target, namely it can simultaneously bind dual targets.

The function (blocking assay for the binding of antigen to receptor) of the SBody described above, which retains activity to dual targets, was evaluated for each of the two targets, and the results are shown in the following table.

TABLE 15 evaluation of functional activity of bispecific antibodies designed for dual targets LAG3 and PD-1

| Antibody number | Blocking the binding activity of LAG3 to Daudi cells | | Blocking the binding activity of PD-1 to PD-Ll | |
| --- | --- | --- | --- | --- |
| | $IC_{50}$, nM | Multiple of $IC_{50}$ variation* | $IC_{50}$, nM | Multiple of $IC_{50}$ variation* |
| LB2373 | 8.05 (9.78[#]) | 0.82 | 1.04 (0.275) | 3.78 |
| LB2374 | 19.4 (9.78[#]) | 1.98 | 0.173 (0.275) | 0.63 |
| LB2379 | 228.4 (28.0) | 8.16 | 3.23 (1.81) | 1.78 |
| LB2380 | 105.7 (28.0) | 3.78 | 2.56 (1.81) | 1.41 |
| LB2371 | 77.5 (9.78) | 7.92 | 0.268 (0.148) | 1.81 |
| LB2372 | 55.1 (9.78) | 5.63 | 0.209 (0.148) | 1.41 |

[#]the values in brackets refer to the blocking activity on the binding of antigen to ligand (IC50) of the monoclonal antibody to the corresponding target under the same experimental conditions.
*multiple of IC50 variation, i.e., the ratio of the IC50 of the bispecific antibody to that of the corresponding monoclonal antibody (control antibody). A larger ratio indicates that the functional activity to a single target of the designed bispecific antibody is weaker. For example, a ratio of 2 indicates that compared with the corresponding monoclonal antibody, the functional activity to the target of the designed bispecific antibody is weaker by 1 time. The experimental error range is within the ratio of 2, namely the activity is not affected. ND: no activity of the molecule preventing the binding of LAG3 to Daudi cells was detected.

The results of the above functional activities show that the bispecific antibody (SBody) designed by the present invention retains the blocking activity against the binding of PD-1 to PD-L1, and only LB2373 shows slightly weaker blocking activity on PD-1/PD-L1 binding (multiple of $IC_{50}$ variation is 3.78). The blocking activities of LB2379, LB2380, LB2371 and LB2372 on the binding activity of LAG-3 to Daudi cells (8.16, 3.78, 7.92 and 5.63 times, respectively) are much weaker, while those of LB2373 and LB2374 are almost unchanged (0.82 and 1.98 times, respectively). This case also indicates that, under the same structure, different PD-1 antibody sequences (LB2373 and LB2374 comprises Pem; LB2371 and LB2372 comprises Nivo) have significantly different effects on functional activity of the SBody, i.e., the SBody design by the present invention is sequence-specific. Combining the results of the functional activities to the two targets, LB2374 is the best, which has the least effect on the functional activity to the two targets (blocking the binding of antigens to receptors).

To evaluate the stability of the bispecific antibodies of the present invention, the antibodies of the present invention were prepared into 1 mg/ml with PBS (pH 7.4). The activity of the samples incubated at 37° C. for 5 days (d5), 10 days (d10), and the activity of the samples stored at −80° C. for 60 days were compared, to evaluate their stability. The results are presented in the table below.

TABLE 16 stability evaluation of bispecific antibodies (SBody) designed for dual targets LAG3 and PD-1

| Antibody number | Binding activity to human LAG3 | | binding activity to human PD-1 | |
| --- | --- | --- | --- | --- |
| | $EC_{50}$, nM | Multiple of $EC_{50}$ variation * | $EC_{50}$, nM | Multiple of $EC_{50}$ variation * |
| LB2371 (d5) | 0.251 (0298[#]) | 0.84 | 0.293 (0.227) | 1.29 |
| LB2371 (d10) | 0.392 (0.298) | 1.32 | 0.324 (0.227) | 1.43 |

TABLE 16-continued stability evaluation of bispecific antibodies
(SBody) designed for dual targets LAG3 and PD-1

| Antibody number | Binding activity to human LAG3 | | binding activity to human PD-1 | |
|---|---|---|---|---|
| | $EC_{50}$, nM | Multiple of $EC_{50}$ variation * | $EC_{50}$, nM | Multiple of $EC_{50}$ variation * |
| LB2374 (d5) | 0.766 (0.699) | 1.1 | 0.12 (0.131) | 0.92 |
| LB2374 (d10) | 1.13 (0.699) | 1.62 | 0.217 (0.131) | 1.66 | the activity value is detected under the same experimental conditions, when the sample is taken out after being stored at −80° C. for 60 days;
* fold change of EC50 (values in brackets) relatives to the activity of the sample stored at −80° C.;
d5 and d10 represent the samples incubated at 37° C. for 5 days and 10 days, respectively.

: the activity value is detected under the same experimental conditions, when the sample is taken out after being stored at −80° C. for 60 days; *: fold change of EC50 (values in brackets) relatives to the activity of the sample stored at −80° C.; d5 and d10 represent the samples incubated at 37° C. for 5 days and 10 days, respectively.

The above results show that after storing at 37° C. for 5 days and 10 days, the binding activities to the dual targets of the bispecific molecules LB2371 and LB2374 designed by the present invention are the same as those of the samples stored at −80° C. for 60 days, that is, the binding activities remain unchanged (the differences of $EC_{50}$ are within 2 times). The results indicate that these molecules are stable. In addition, the samples were analyzed by Polyacryamide Gel Electrophoresis (PAGE) and no degradation was detected under both denaturing and non-denaturing conditions. These results also show that these bispecific molecules are structurally stable.

TABLE 17 evaluation of expression yields of bispecific antibodies
designed for dual targets LAG3 and PD-1

| Antibody number | Expression yield (mg/L) | Antibody number | Expression yield (mg/L) | Antibody number | Expression yield (mg/L) |
|---|---|---|---|---|---|
| LB2373 | 101.3 | LB2371 | 22.9 | LB2379 | 101.9 |
| LB2374 | 133.7 | LB2372 | 24.6 | LB2380 | 127.1 |
| LB203 | 0.08 | LB202 | 2.50 | LB214 | 0.23 |
| LB201 | 0.79 | LB152 | 0.93 | LB216 | 1.27 |
| LB234 | 1.95 | LB211 | 0.71 | | |

The above results indicate that the expression yields of the bispecific antibodies (SBody) designed by the present invention for LAG3 and PD1 vary a lot. Very unexpectedly, the expression yields of LB2373, LB2374, LB2379, and LB2380 are relatively high. The expression yields of SBodies designed with Ab835 as the scFv are much lower than those of SBodies designed with Ab2317 as the scFv in expression yield, which are more than 65 times lower, such as LB2374 vs. LB234, or more than 140 times lower, such as LB2373 vs. LB211.

These data indicate that the unexpected effects of the bispecific antibodies (SBody) designed for the anti-LAG3 antibodies Ab2317 and PD1 antibody of the present invention not only has unexpected effects in terms of activity, function and stability, but also the expression amount is correlated with the sequence-specific design.

LB2371 light chain amino acid sequence: SEQ ID NO: 44; the amino acid sequence comprising a heavy chain: SEQ ID NO: 46; LB2373 light chain amino acid sequence: SEQ ID NO: 42; the amino acid sequence comprising a heavy chain: SEQ ID NO: 47;

light chain amino acid sequence of LB2374: SEQ ID NO: 42; amino acid sequence of LB2374 comprising a heavy chain:

SEQ ID NO: 48

```
QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

DYWGQGTLVTVSSASTKGPSVFPLAPCSRSTSESTAALGCLVKDYFPEPV

TVSWNSGALTSGVHTFPAVLQSSGLYSLSSVVTVPSSSLGTKTYTCNVDH

KPSNTKVDKRVESKYGPPCPPCPAPEFLGGPSVFLFPPKPKDTLMISRTP

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLY

SRLTVDKSRWQEGNVFSCSVMHEALHNHYTQKSLSLSLGAGGGGSGGGGS

GGGGSQVQLVQSGAEVKKPGASVKVSCKASGYTFTDYEMHWVKQAPGQGL

EWIGGIDPETEGIAYNQKFRGRATLTADKSTSTAYMELRSLRSDDTAVYY

CTNSNYYGGREAWFAYWGQGTLVTVSSGGGGSGGGGSGGGGSDIQMTQSP

SSLSASVGDRVTITCRASQDIGSSLNWYQQKPGKAPKRLIYATSSLDSGV

PSRFSGSRSGSDFTLTISSLQPEDFATYYCLQYVTSPLTFGGGTKVEIK
```

The amino acid sequence of LB2379 comprising a light chain: SEQ ID NO: 49; the amino acid sequence of the heavy chain: SEQ ID NO: 43; the amino acid sequence of LB2380 comprising a light chain: SEQ ID NO: 50; the amino acid sequence of the heavy chain: SEQ ID NO: 43.

Example 14: PK Evaluation of LAG-3 Antibody of the Present Invention

Experimental C57BL/6 cnc strain mice (purchased from Zhejiang Weitonglihua Experimental Animal Technology Co., Ltd., License No.: SCXK(Zhe)2018-0001), female, 8 weeks old, 6 mice, about 20 μg/mouse. The mice were fed in an SPF environment at 20-25° C. with 40%-60% of humidity. After being raised in the laboratory environment for 3 days, the mice were randomly divided into 2 groups with 3 mice per group. The drugs to be tested (LAG-3 antibodies Ab2317 of the present invention and Ref) were subcutaneously injected into the back of mice. The injection volume was 200 μl and the dose administered was 20 mg/kg/mouse.

Blood was taken from orbit of mice after injection of the drugs to be tested at time points of 0.5, 1, 2, 4, 7, 24, 31, 48, 56, 72, 96, 120, 144, 168, 192, 216, 240, 264, 288, 312, 336, 360, 384, 408, 432, 456, 480 and 504 hours. The obtained blood samples were centrifuged to obtain the supernatants, which were stored at −20° C. for further test. After the collection of blood samples, ELISA was used to detect the contents of Ab2317 or Ref in blood samples at each time point. Excel software was used to analyze the PK data and to calculate the $T_{1/2}$ of the drugs to be tested. The results are shown in the table below

TABLE 18

| PK evaluation of antibody AB2317 of the present invention | | | | | | | |
|---|---|---|---|---|---|---|---|
| | Ab2317 | | | | Ref | | |
| PK | Mouse number | | | | Mouse number | | |
| indicator | 1 | 2 | 3 | Average | 4 | 5 | 6 | Average |
| $T_{max}$ (h) | 31 | 24 | 31 | 28.7 | 24 | 31 | 24 | 26.3 |
| $C_{max}$ (mg/ml) | 416.9 | 359.5 | 269.9 | 348.8 | 280.3 | 341.3 | 278.5 | 300.0 |
| $T_{1/2}$ (h) | 231.0 | 239.0 | 135.9 | 202.0 | 173.3 | 238.9 | 154.0 | 188.7 |

The above results indicate that the antibody Ab2317 of the present invention exhibits better PK properties including longer T1/2 (Ab2317 T1/2 is 202 hours, Ref is 188.7 hours), higher Cmax, etc.

Example 15: PK Evaluation of Bispecific Antibody (SBody) Designed by the Present Invention for Dual Targets LAG3 and PD-1

Experimental C57BL/6 cnc strain mice (purchased from Vital River Laboratory Animal Technology Co., Ltd., License No.: SCXK(Zhe)2018-0001) and double-transgenic CB7BL/6 mice (abbreviated as C57BL/6-DKI) of human PD-1 and human LAG-3 purchased from Jiangsu Gempharmatech Co., Ltd., production license No.: SCXK(Su)2018-0008), female, 8 weeks old, 6 mice of each strain, about 20 μg/mouse. The mice were fed in an SPF environment at 20-25° C. with humidity 40%-60%. After the mice of the two strains were raised in the laboratory environment for 3 days, the mice of each strain was randomly divided into 2 groups with 3 mice per group. The drug to be tested (Ab2374) were subcutaneously injected into the back of mice. The injection volume was 200 μl and the dose administered was 20 mg/kg/mouse.

Blood was taken from orbit of mice after injection of the drug to be tested at time points of 0, 0.5, 1, 2, 6, 24, 31, 48, 56, 72, 96, 120, 144, 168, 192, 216, 240, 264, 288, 312, 336, 360, 384, 408 and 432 hours. The blood samples were centrifuged to obtain the supernatants, which were stored at −20° C. for further test. After the collection of blood samples, ELISA was used to detect the contents of Ab2374 in blood samples at each time point. Specifically:

PD-1 detection method: a 96-well microplate was coated with PD-1 protein (coming, Cat. No.: 3590). 5% skimmed milk was added and the microplate was incubated for 2 hours for blocking; and then the microplate was washed for later use. The standard curve was prepared with Ab2374; the serum to be tested was diluted in proportion and then added to the treated 96-well microplate. After reacting at 37° C. for 1 hour, the microplate was washed and the diluted enzyme-labeled antibody Peroxidase AffiniPure Goat Anti-Human IgG (Jackson, Cat. No.: 109-035-003) was added. After half an hour, the microplate was washed. TMB (Surmodic, Cat. No.: TTMB-1000-01) was added for color development and $H_2SO_4$ was added to stop reaction, followed by reading absorption value at 450 nm with a microplate reader.

PD-1/LAG-3 (sandwich ELISA) detection method: a 96-well microplate was coated with PD-1 protein (corning, Cat. No.: 3590). 5% skimmed milk was added and the microplate was incubated for 2 hours for blocking; and then the microplate was washed for later use. The standard curve was prepared with Ab2374; the serum to be tested was diluted in proportion and then added to the treated 96-well microplate. After reacting at 37° C. for 1 hour, the microplate was washed. Subsequently, biotinylated LAG-3 protein with a fixed concentration was added. After reacting at 37° C. for 1 hour, the microplate was washed and the diluted enzyme-labeled antibody streptavidin-HRP (genscript, Cat. No.: M00091) was added. After half an hour, the microplate was washed, TMB (Surmodic, Cat. No.: TTMB-1000-01) was added for color development and $H_2SO_4$ was added to stop reaction, followed by reading absorption value at 450 nm with a microplate reader.

Excel was used to analyze the PK data and to calculate the $T_{1/2}$ of the drug to be tested. The results are shown in the table below.

TABLE 19

| PK evaluation of the bispecific antibody Ab2374 of the present invention (PD-1 test results) | | | | | | | |
|---|---|---|---|---|---|---|---|
| | C57BL/6 | | | | C57BL/6-DKI | | |
| PK | Mouse number | | | | Mouse number | | |
| indicator | 1 | 2 | 3 | Average | 4 | 5 | 6 | Average |
| $T_{max}$ (h) | 31 | 48 | 48 | 42.3 | 48 | 72 | 48 | 56 |
| $C_{max}$ (mg/ml) | 657.4 | 509.0 | 407.0 | 524.5 | 181.0 | 263.5 | 248.4 | 231.0 |
| $T_{1/2}$ (h) | 144.7 | 169.0 | 144.4 | 152.7 | 44.4 | 36.1 | 41.8 | 40.8 |

TABLE 20

| PK Evaluation of the bispecific antibody Ab2374 of the present invention (PD-1/LAG-3 test results) | | | | | | | |
|---|---|---|---|---|---|---|---|
| | C57BL/6 | | | | C57BL/6-DKI | | |
| PK | Mouse number | | | | Mouse number | | |
| indicator | 1 | 2 | 3 | Average | 4 | 5 | 6 | Average |
| $T_{max}$ (h) | 48 | 48 | 48 | 48 | 48 | 48 | 48 | 48 |
| $C_{max}$ (mg/ml) | 422.9 | 698.9 | 676.4 | 599.4 | 452.9 | 313.4 | 276.6 | 347.6 |
| $T_{1/2}$ (h) | 161.2 | 138.6 | 154.0 | 151.3 | 32.3 | 35.9 | 33.0 | 33.7 |

The sandwich ELISA was used to detect PK properties of the binding of the molecule to PD-1 first and then to LAG-3. The results in table 20 show that, unexpectly, the PK properties (e.g., Cmax, T1/2) detected by the sandwich ELISA of the bispecific antibody of the present invention in C57BL/6 mice is almost the same as those obtained by detecting the binding to PD-1 alone. It shows that the bispecific antibody of the present invention is stable in vivo in mice and no abscission of scFv (LAG-3) is observed. This PK properties is also similar to that of the Ab2317 antibody alone (Table 18). In addition, since the antibody of the present invention has specific target binding in hPD-1/hLAG-3 double transgenic mice (C57BL/6-DKI), Cmax and T1/2 are both reduced, and surprisingly, PK detected by sandwich ELISA is consistent with PK detected with PD-1 alone, which indicates that the bispecific antibody of the present invention is also stable in mice with specific target binding and no scFv shedding occurs.

According to the method of Example 1 of the present invention, the above DVD-designed bispecific antibodies were cloned, expressed and purified, respectively. The results of gel electrophoresis (PAGE) show that both light and heavy chains of these antibodies are prone to linker cleavage. By linking one antibody to N-terminus or C-terminus of the light chain or the heavy chain of an antibody for another target in the form of scFv, the bispecific antibody with optimized sequence and design can be obtained by screening, which can avoid/reduce linker cleavage (see the previous embodiments), and the binding activity to the dual targets, in vitro functional activity, and in vivo efficacy to the dual targets are retained. Because of a structure similar to normal IgG, the preferred bispecific antibody (SBody of the present invention) is not only stable, but also convenient in purification process, which provides great convenience for both process and purification in later development process.

What is claimed is:

1. A lymphocyte-activation gene 3 (LAG-3) binding protein comprising a light chain variable region and a heavy chain variable region; wherein the light chain variable region comprises a CDR1 having an amino acid sequence of SEQ ID NO: 5, a CDR2 having an amino acid sequence of SEQ ID NO: 6, and a CDR3 having an amino acid sequence of SEQ ID NO: 7; the heavy chain variable region comprises a CDR1 having an amino acid sequence of SEQ ID NO: 8, a CDR2 having an amino acid sequence of SEQ ID NO: 9, and a CDR3 having an amino acid sequence of SEQ ID NO: 10.

2. The LAG-3 binding protein of claim 1, wherein the light chain variable region comprises an amino acid sequence of SEQ ID NO: 25, and the heavy chain variable region comprises an amino acid sequence of SEQ ID NO: 31; or the light chain variable region comprises an amino acid sequence of SEQ ID NO: 27, and the heavy chain variable region comprises an amino acid sequence of SEQ ID NO: 31; or the light chain variable region comprises an amino acid sequence of SEQ ID NO: 28, and the heavy chain variable region comprises an amino acid sequence of SEQ ID NO: 31; or the light chain variable region comprises an amino acid sequence of SEQ ID NO: 29, and the heavy chain variable region comprises an amino acid sequence of SEQ ID NO: 31; or the light chain variable region comprises an amino acid sequence of SEQ ID NO: 26, and the heavy chain variable region comprises an amino acid sequence of SEQ ID NO: 32; or the light chain variable region comprises an amino acid sequence of SEQ ID NO: 28, and the heavy chain variable region comprises an amino acid sequence of SEQ ID NO: 36.

3. The LAG-3 binding protein of claim 1, which is an antibody, a Fab, a Fab', a F(ab')$_2$, a Fv, a scFv, a bispecific antibody, a multispecific antibody, or a monoclonal antibody or a polyclonal antibody derived from the antibody.

4. The LAG-3 binding protein of claim 3, comprising a human antibody light chain constant region and a human antibody heavy chain constant region; the light chain constant region of the human antibody is a κ chain or a λ chain, and the heavy chain constant region of the human antibody is a hIgG1, a hIgG2, a hIgG4.

5. The LAG-3 binding protein of claim 4, wherein the amino acid sequence of the light chain is SEQ ID NO: 38, and the amino acid sequence of the heavy chain is SEQ ID NO: 40; or the amino acid sequence of the light chain is SEQ ID NO: 38, and the amino acid sequence of the heavy chain is SEQ ID NO: 41; or the amino acid sequence of the light chain is SEQ ID NO: 39, and the amino acid sequence of the heavy chain is SEQ ID NO: 40; or the amino acid sequence of the light chain is SEQ ID NO: 39, and the amino acid sequence of the heavy chain is SEQ ID NO: 41.

6. A bispecific antibody targeting LAG-3 comprising a first protein functional region and a second protein functional region, wherein the first protein functional region is the LAG-3 binding protein of claim 1; the second protein functional region is an anti-PD-1 antibody; the first protein functional region and the second protein functional region are selected from immunoglobulin, scFv, Fab, Fab' or F(ab')$_2$, respectively, and only one of the first protein functional region and second protein functional region is an immunoglobulin.

7. The bispecific antibody targeting LAG-3 of claim 6, wherein the first protein functional region is an immunoglobulin, and the second protein functional region is one or more scFvs; or the first protein functional region is one or more scFvs, the second protein functional region is an immunoglobulin, and the immunoglobulin comprises a constant region comprising a light chain constant region of human antibody and a heavy chain constant region of human antibody; the light chain constant region of human antibody is a κ chain or a λ chain, and the heavy chain constant region of human antibody is a hIgG1, a hIgG2 or a hIgG4.

8. The bispecific antibody targeting LAG-3 of claim 6, wherein, the scFv comprises a heavy chain variable region and a light chain variable region, the heavy chain variable region and the light chain variable region are connected by a linker; and the scFv is connected to the immunoglobulin by a linker, having the amino acid sequence of SEQ ID NO: 51, 52, 53 or 54.

9. The bispecific antibody targeting LAG-3 of claim 8, wherein, the amino acid sequence of the linker is SEQ ID NO: 53, or the number of the scFv is two, and these two scFvs are symmetrically connected to the C-terminus or N-terminus of the light chains or the heavy chains of the immunoglobulin;

the scFv has a structure of light chain variable region-linker-heavy chain variable region, and the C-terminus of the heavy chain variable regions of the two scFvs are symmetrically connected to the N-terminus of two heavy chain variable regions of the immunoglobulin by the amino acid sequence of SEQ ID NO: 53, respectively, or the N-terminus of the light chain variable regions of these two scFvs are symmetrically connected to the C-terminus of two heavy chains of the immunoglobulin by the amino acid sequence of SEQ ID NO: 53, respectively; or the scFv has a structure of a heavy chain variable region-linker-light chain variable region, and the C-terminus of the light chain variable regions of these two scFvs are symmetrically connected to the N-terminus of two light chain variable regions of the immunoglobulin by the amino acid sequence of SEQ ID NO: 53, respectively, or the N-terminus of the heavy chain variable regions of these two scFvs are symmetrically connected to the C-terminus of two light chain variable regions of the immunoglobulin by the amino acid sequence of SEQ ID NO: 53, respectively.

10. The bispecific antibody targeting LAG-3 of claim 6, wherein the scFv has a structure of light chain variable region-linker-heavy chain variable region, in which N-terminus of the light chain variable region or C-terminus of the heavy chain variable region is correspondingly connected to C-terminus or N-terminus of the light chain or heavy chain of the immunoglobulin by a linker; or the scFv has a structure of heavy chain variable region-linker-light chain variable region, in which N-terminus of the heavy chain variable region or C-terminus of the light chain variable region is correspondingly connected to C-terminus or N-terminus of the light chain or the heavy chain of the immunoglobulin by a linker.

11. The bispecific antibody targeting LAG-3 of claim 6, which is selected from the group consisting of:

(1) the first protein functional region is an immunoglobulin comprising the following light chain and heavy chain: the amino acid sequence of the light chain is SEQ ID NO: 39, the amino acid sequence of the heavy chain is SEQ ID NO: 40; or the amino acid sequence of the light chain is SEQ ID NO: 39, the amino acid sequence of the heavy chain is SEQ ID NO: 41; when the scFvs are connected to the C-terminus of two heavy chains of the immunoglobulin, the C-terminus of the heavy chains is mutated from K to A;

the second protein functional region is a scFv, wherein the amino acid sequence of the light chain variable region of the scFv is located at positions 1-107 of SEQ ID NO: 42, and the amino acid sequence of the heavy chain variable region of the scFv is located at positions 1-113 of SEQ ID NO: 43; or the amino acid sequence of the light chain variable region of the scFv is located at positions 1-111 of SEQ ID NO: 44, and the amino acid sequence of the heavy chain variable region of the scFv is located at positions 1-120 of SEQ ID NO: 45;

(2) the first protein functional region is a scFv, wherein, the amino acid sequence of the light chain variable region of the scFv is SEQ ID NO: 28, the amino acid sequence of the heavy chain variable region of the scFv is SEQ ID NO: 31; or the amino acid sequence of the light chain variable region of the scFv is SEQ ID NO: 28, the amino acid sequence of the heavy chain variable region of the scFv is SEQ ID NO: 36; and the second protein functional region is an immunoglobulin comprising the following light chains and heavy chains: the amino acid sequence of the light chain of the immunoglobulin is SEQ ID NO: 42, the amino acid sequence of the heavy chain of the immunoglobulin is SEQ ID NO: 43; or the amino acid sequence of the light chain of the immunoglobulin is SEQ ID NO: 44, the amino acid sequence of the heavy chain of the immunoglobulin is SEQ ID NO: 45; when the scFv is connected to the C-terminus of the two heavy chains of the immunoglobulin, the C-terminus of the heavy chains is mutated from K to A.

12. The bispecific antibody targeting LAG-3 of claim 6, which is selected from the group consisting of:

(i) the first protein functional region is scFv, wherein the amino acid sequence of the light chain variable region of the scFv is SEQ ID NO: 28, the amino acid sequence of the heavy chain variable region of the scFv is SEQ ID NO: 31, and the amino acid sequence of the linker is SEQ ID NO: 53; the second protein functional region is an immunoglobulin, wherein the amino acid sequence of the light chain of the immunoglobulin is SEQ ID NO: 42, and the amino acid sequence of the heavy chain of the immunoglobulin is SEQ ID NO: 43; wherein, the number of the scFv is two; the scFv has a structure of light chain variable region-linker-heavy chain variable region, and the C-terminus of the heavy chain variable regions of these two scFvs are symmetrically connected to the N-terminus of two heavy chains of the immunoglobulin by the amino acid sequence of SEQ ID NO: 53, respectively; or the scFv has a structure of heavy chain variable region-linker-light chain variable region, and the N-terminus of the heavy chain variable regions of these two scFvs are symmetrically connected to the C-terminus of two heavy chains of the immunoglobulin by the amino acid sequence of SEQ ID NO: 53, respectively, and the C-terminus is mutated from K to A; or the scFv has a structure of light chain variable region-linker-heavy chain variable region, the C-terminus of the heavy chain variable regions of these two scFvs are symmetrically connected to the N-terminus of two light chains of the immunoglobulin by the amino acid sequence of SEQ ID NO: 53, respectively; or the scFv has a structure of heavy chain variable region-linker-light chain variable region, the N-terminus of the heavy chain variable regions of these two scFvs are symmetrically connected to the C-terminus of two light chains of the immunoglobulin by the amino acid sequence of SEQ ID NO: 53, respectively;

(ii) the first protein functional region is scFv, wherein the amino acid sequence of the light chain variable region of the scFv is SEQ ID NO: 28, the amino acid sequence of the heavy chain variable region of the scFv is SEQ ID NO: 31, and the amino acid sequence of the linker is SEQ ID NO: 53; the second protein functional region is an immunoglobulin, wherein the amino acid sequence of the light chain of the immunoglobulin is SEQ ID NO: 44, and the amino acid sequence of the heavy chain of the immunoglobulin is SEQ ID NO: 45; wherein, the number of the scFv is two; the scFv has a structure of light chain variable region-linker-heavy chain variable region, and the C-terminus of the heavy chain variable regions of these two scFvs are symmetrically connected to the N-terminus of two heavy chains of the immunoglobulin by the amino acid sequence of SEQ ID NO: 53, respectively; or the scFv has a structure of heavy chain variable region-linker-light chain variable region, and the N-terminus of the heavy chain variable regions of these two scFvs are symmetrically connected to the C-terminus of two heavy chains of the immunoglobulin through the amino acid sequence of SEQ ID NO: 53, respectively, and the C-terminus is mutated from K to A; or the scFv has a structure of light chain variable region-linker-heavy chain variable region, the C-terminus of the heavy chain variable regions of these two scFvs are symmetrically connected to the N-terminus of two light chains of the immunoglobulin by the amino acid sequence of SEQ ID NO: 53, respectively; or the scFv has a structure of heavy chain variable region-linker-light chain variable region, the N-terminus of the heavy chain variable regions of these two scFvs are symmetrically connected to the C-terminus of two light chains of the immunoglobulin by the amino acid sequence of SEQ ID NO: 53, respectively; and (iii) the first protein functional region is scFv, wherein the amino acid sequence of the light chain variable region of the scFv is SEQ ID NO: 28, the amino acid sequence of the heavy chain variable region of the scFv is SEQ ID NO: 36, and the amino acid sequence of the linker is SEQ ID NO: 53; the functional region of the second protein is an immunoglobulin, the amino acid sequence of the light chain of the immunoglobulin is SEQ ID NO: 44, and the amino acid sequence of the heavy chain of the immunoglobulin is SEQ ID NO: 45;

wherein, the number of the scFv is two; the scFv has a structure of light chain variable region-linker-heavy chain variable region, the C-terminus of the heavy chain variable regions of these two scFvs are symmetrically connected to the N-terminus of two heavy chains of the immunoglobulin by the amino acid sequence of SEQ ID NO: 53, respectively; or the scFv has a structure of a heavy chain variable region-linker-light chain variable region, the N-terminus of the heavy chain variable regions of these two scFvs are symmetrically connected to the C-terminus of two heavy chains of the immunoglobulin by the amino acid sequence of SEQ ID NO: 53, respectively, and the C-terminus is mutated from K to A.

13. The bispecific antibody targeting LAG-3 of claim 12, wherein the bispecific antibody targeting LAG-3 comprises the following amino acid sequences:

an amino acid sequence of SEQ ID NO: 44 as a light chain sequence, and an amino acid sequence of SEQ ID NO: 46 as a heavy chain containing sequence; or an amino acid sequence of SEQ ID NO: 42 as a light chain sequence, and an amino acid sequence of SEQ ID NO: 47 as a heavy chain containing sequence; or an amino acid sequence of SEQ ID NO: 42 as a light chain sequence, and an amino acid sequence of SEQ ID NO: 48 as a heavy chain containing sequence;

or an amino acid sequence of SEQ ID NO: 49 as a light chain containing sequence, and an amino acid sequence of SEQ ID NO: 43 as a heavy chain sequence; or an amino acid sequence of SEQ ID NO: 50 as a light chain containing sequence, and an amino acid sequence of SEQ ID NO: 43 as a heavy chain sequence.

14. An antibody-drug conjugate comprising a cytotoxic agent, and the LAG-3 binding protein of claim 1.

15. A pharmaceutical composition comprising the LAG-3 binding protein of claim 1.

16. An isolated nucleic acid encoding the LAG-3 binding protein of claim 1.

17. An expression vector comprising the isolated nucleic acid of claim 16.

18. A host cell comprising the expression vector of claim 17.

19. A method for preparing the LAG-3 binding protein, which comprises: culturing the host cell of claim 18 and obtaining LAG-3 binding protein from the culture.

20. A method for treating cancer, comprising administering to a subject in need of a medicament comprising a bispecific antibody targeting LAG-3 comprising a first protein functional region and a second protein functional region;

wherein the first protein functional region is the LAG-3 binding protein of claim 1; the second protein functional region is an anti-PD-1 antibody;

the first protein functional region and the second protein functional region are selected from immunoglobulin, scFv, Fab, Fab' or F(ab')$_2$, respectively, and only one of the first protein functional region and second protein functional region is an immunoglobulin.

*    *    *    *    *

```
                           SEQUENCE LISTING

<160> NUMBER OF SEQ ID NOS: 54

<210> SEQ ID NO 1
<211> LENGTH: 500
<212> TYPE: DNA
<213> ORGANISM: Artificial Sequence
<220> FEATURE:
<223> OTHER INFORMATION: Base sequence of the light chain variable
      region of the murine monoclonal antibody mab23

<400> SEQUENCE: 1
gatgaggacc cctgctcaga ttcttgggat cttgttgctc ttgtttccag gtaccagatg      60
tgacattcag atgatccagt ctccatcctc cttatctgcc tctctgggag aaagagtcag     120
tctcacttgt cgggcaagtc aggacattgg tagtagttta aactggcttc agcaggaacc     180
agatggaact atcaaacgcc tgatctacgc cacatccagt ttagattctg gtgtccccaa     240
aaggttcagt ggcagtaggt ctgggtcaga ttattctctc accatcagca gccttgagtc     300
tgaagatttt gtagactatt actgtctaca atatgttact tctccgctca cgttcggtgc     360
tgggaccaag ctggagctga aacgggctga tgctgcacca actgtatcca tcttcccacc     420
atccagtgag cagttaacat ctggaggtgc ctcagtcgtg tgcttctgaa caactctacc     480
ccagagacat caattccctg                                                 500

<210> SEQ ID NO 2
<211> LENGTH: 539
<212> TYPE: DNA
<213> ORGANISM: Artificial Sequence
<220> FEATURE:
<223> OTHER INFORMATION: Base sequence of the heavy chain variable
      region of the murine monoclonal antibody mab23

<400> SEQUENCE: 2
gatgaaatgg cagctgggtt tttctcttcc tcctgtcagt aattgcaggt gtccaatccc      60
aggttcaact gcagcagtct ggggctgagc tggtgaggcc tggggcttca gtgacgctgt     120
cctgcaaggc ttcgggctac acatttactg actatgaaat gcactgggtg aaacagacac     180
ctgtgcatgg cctggaatgg attggaggta ttgatcctga aactgaaggc attgcctata     240
atcagaagtt caggggcaag gccatactga ctgcagacaa atcctccatc acagcctaca     300
tggagctccg cagcctgaca tctgaggact ctgccgtcta ttactgtaca aactccaatt     360
actacggtgg aagggaggcc tggtttgctt actggggcca agggactctg gtcactgtct     420
ctggagccaa aacgacaccc ccatctgtct atccactggc ccctggatct gctgcccaaa     480
ctaactccat ggtgaccctg ggatgcctgg tcaagggcta tacatagcca ttactcaaa      539

<210> SEQ ID NO 3
<211> LENGTH: 107
<212> TYPE: PRT
<213> ORGANISM: Artificial Sequence
<220> FEATURE:
<223> OTHER INFORMATION: Amino acid sequence of the light chain variable
      region of the murine monoclonal antibody mab23

<400> SEQUENCE: 3

Asp Ile Gln Met Ile Gln Ser Pro Ser Ser Leu Ser Ala Ser Leu Gly
```

```
1               5              10             15

Glu Arg Val Ser Leu Thr Cys Arg Ala Ser Gln Asp Ile Gly Ser Ser
            20              25              30

Leu Asn Trp Leu Gln Gln Glu Pro Asp Gly Thr Ile Lys Arg Leu Ile
        35              40              45

Tyr Ala Thr Ser Ser Leu Asp Ser Gly Val Pro Lys Arg Phe Ser Gly
    50              55              60

Ser Arg Ser Gly Ser Asp Tyr Ser Leu Thr Ile Ser Ser Leu Glu Ser
65              70              75              80

Glu Asp Phe Val Asp Tyr Tyr Cys Leu Gln Tyr Val Thr Ser Pro Leu
                85              90              95

Thr Phe Gly Ala Gly Thr Lys Leu Glu Leu Lys
            100             105
```

<210> SEQ ID NO 4
<211> LENGTH: 122
<212> TYPE: PRT
<213> ORGANISM: Artificial Sequence
<220> FEATURE:
<223> OTHER INFORMATION: Amino acid sequence of the heavy chain variable
      region of the murine monoclonal antibody mab23

<400> SEQUENCE: 4

```
Gln Val Gln Leu Gln Gln Ser Gly Ala Glu Leu Val Arg Pro Gly Ala
1               5              10             15

Ser Val Thr Leu Ser Cys Lys Ala Ser Gly Tyr Thr Phe Thr Asp Tyr
            20              25              30

Glu Met His Trp Val Lys Gln Thr Pro Val His Gly Leu Glu Trp Ile
        35              40              45

Gly Gly Ile Asp Pro Glu Thr Glu Gly Ile Ala Tyr Asn Gln Lys Phe
    50              55              60

Arg Gly Lys Ala Ile Leu Thr Ala Asp Lys Ser Ser Ile Thr Ala Tyr
65              70              75              80

Met Glu Leu Arg Ser Leu Thr Ser Glu Asp Ser Ala Val Tyr Tyr Cys
                85              90              95

Thr Asn Ser Asn Tyr Tyr Gly Gly Arg Glu Ala Trp Phe Ala Tyr Trp
            100             105             110

Gly Gln Gly Thr Leu Val Thr Val Ser Gly
        115             120
```

<210> SEQ ID NO 5
<211> LENGTH: 11
<212> TYPE: PRT
<213> ORGANISM: Artificial Sequence
<220> FEATURE:
<223> OTHER INFORMATION: Light chain CDR1

<400> SEQUENCE: 5

```
Arg Ala Ser Gln Asp Ile Gly Ser Ser Leu Asn
1               5              10
```

<210> SEQ ID NO 6
<211> LENGTH: 7
<212> TYPE: PRT
<213> ORGANISM: Artificial Sequence
<220> FEATURE:
<223> OTHER INFORMATION: Light chain CDR2

<400> SEQUENCE: 6

```
Ala Thr Ser Ser Leu Asp Ser
```

```
1               5

<210> SEQ ID NO 7
<211> LENGTH: 9
<212> TYPE: PRT
<213> ORGANISM: Artificial Sequence
<220> FEATURE:
<223> OTHER INFORMATION: Light chain CDR3

<400> SEQUENCE: 7

Leu Gln Tyr Val Thr Ser Pro Leu Thr
1               5

<210> SEQ ID NO 8
<211> LENGTH: 10
<212> TYPE: PRT
<213> ORGANISM: Artificial Sequence
<220> FEATURE:
<223> OTHER INFORMATION: Heavy chain CDR1

<400> SEQUENCE: 8

Gly Tyr Thr Phe Thr Asp Tyr Glu Met His
1               5                   10

<210> SEQ ID NO 9
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 9

Gly Ile Asp Pro Glu Thr Glu Gly Ile Ala Tyr Asn Gln Lys Phe Arg
1               5                   10                  15

Gly

<210> SEQ ID NO 10
<211> LENGTH: 13
<212> TYPE: PRT
<213> ORGANISM: Artificial Sequence
<220> FEATURE:
<223> OTHER INFORMATION: Heavy chain CDR3

<400> SEQUENCE: 10

Ser Asn Tyr Tyr Gly Gly Arg Glu Ala Trp Phe Ala Tyr
1               5                   10

<210> SEQ ID NO 11
<211> LENGTH: 5
<212> TYPE: PRT
<213> ORGANISM: Artificial Sequence
<220> FEATURE:
<223> OTHER INFORMATION: Heavy chain CDR1, defined by Kabat definition

<400> SEQUENCE: 11

Asp Tyr Glu Met His
1               5

<210> SEQ ID NO 12
<211> LENGTH: 10
<212> TYPE: PRT
<213> ORGANISM: Artificial Sequence
<220> FEATURE:
<223> OTHER INFORMATION: Heavy chain CDR2, defined by AbM definition

<400> SEQUENCE: 12
```

```
Gly Ile Asp Pro Glu Thr Glu Gly Ile Ala
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Heavy chain CDR1, defined by Chothia definition

<400> SEQUENCE: 13

Gly Tyr Thr Phe Thr Asp Tyr
1               5

<210> SEQ ID NO 14
<211> LENGTH: 6
<212> TYPE: PRT
<213> ORGANISM: Artificial Sequence
<220> FEATURE:
<223> OTHER INFORMATION: Heavy chain CDR2, defined by Chothia definition

<400> SEQUENCE: 14

Asp Pro Glu Thr Glu Gly
1               5

<210> SEQ ID NO 15
<211> LENGTH: 7
<212> TYPE: PRT
<213> ORGANISM: Artificial Sequence
<220> FEATURE:
<223> OTHER INFORMATION: Light chain CDR1, defined according to Contact
      definition

<400> SEQUENCE: 15

Gly Ser Ser Leu Asn Trp Leu
1               5

<210> SEQ ID NO 16
<211> LENGTH: 11
<212> TYPE: PRT
<213> ORGANISM: Artificial Sequence
<220> FEATURE:
<223> OTHER INFORMATION: Light chain CDR2, defined according to Contact
      definition

<400> SEQUENCE: 16

Lys Arg Leu Ile Tyr Ala Thr Ser Ser Leu Asp
1               5                   10

<210> SEQ ID NO 17
<211> LENGTH: 8
<212> TYPE: PRT
<213> ORGANISM: Artificial Sequence
<220> FEATURE:
<223> OTHER INFORMATION: Light chain CDR3, defined according to Contact
      definition

<400> SEQUENCE: 17

Leu Gln Tyr Val Thr Ser Pro Leu
1               5

<210> SEQ ID NO 18
<211> LENGTH: 6
<212> TYPE: PRT
<213> ORGANISM: Artificial Sequence
<220> FEATURE:
<223> OTHER INFORMATION: Heavy chain CDR1, defined according to Contact
      definition
```

<400> SEQUENCE: 18

Thr Asp Tyr Glu Met His
1               5

<210> SEQ ID NO 19
<211> LENGTH: 13
<212> TYPE: PRT
<213> ORGANISM: Artificial Sequence
<220> FEATURE:
<223> OTHER INFORMATION: Heavy chain CDR2, defined according to Contact
      definition

<400> SEQUENCE: 19

Trp Ile Gly Gly Ile Asp Pro Glu Thr Glu Gly Ile Ala
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Heavy chain CDR3, defined according to Contact
      definition

<400> SEQUENCE: 20

Thr Asn Ser Asn Tyr Tyr Gly Gly Arg Glu Ala Trp Phe Ala
1               5                   10

<210> SEQ ID NO 21
<211> LENGTH: 107
<212> TYPE: PRT
<213> ORGANISM: Artificial Sequence
<220> FEATURE:
<223> OTHER INFORMATION: kappa chain of light chain constant region of
      human antibody

<400> SEQUENCE: 21

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 22
<211> LENGTH: 327
<212> TYPE: PRT
<213> ORGANISM: Artificial Sequence
<220> FEATURE:
<223> OTHER INFORMATION: Heavy chain constant region of human IgG4

<400> SEQUENCE: 22

Ala Ser Thr Lys Gly Pro Ser Val Phe Pro Leu Ala Pro Cys Ser Arg
1               5                   10                  15

-continued

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325
```

```
<210> SEQ ID NO 23
<211> LENGTH: 107
<212> TYPE: PRT
<213> ORGANISM: Artificial Sequence
<220> FEATURE:
<223> OTHER INFORMATION: light chain variable region, LG2312

<400> SEQUENCE: 23
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ser Ser
            20                  25                  30

Leu Asn Trp Tyr Gln Gln Lys Pro Gly Lys Ala Pro Lys Leu Leu Ile
            35                  40                  45
```

-continued

```
Tyr Ala Thr Ser Ser Leu Asp Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Val Thr Ser Pro Leu
                85                  90                  95

Thr Phe Gly Gly Gly Thr Lys Val Glu Ile Lys
                100                 105
```

<210> SEQ ID NO 24
<211> LENGTH: 107
<212> TYPE: PRT
<213> ORGANISM: Artificial Sequence
<220> FEATURE:
<223> OTHER INFORMATION: light chain variable region, LG2313

<400> SEQUENCE: 24

```
Asp Ile Gln Met Ile Gln Ser Pro Ser Ser Leu Ser Ala Ser Val Gly
1                   5                   10                  15

Asp Arg Val Thr Ile Thr Cys Arg Ala Ser Gln Asp Ile Gly Ser Ser
                20                  25                  30

Leu Asn Trp Leu Gln Gln Lys Pro Gly Gly Ala Ile Lys Arg Leu Ile
            35                  40                  45

Tyr Ala Thr Ser Ser Leu Asp Ser Gly Val Pro Ser Arg Phe Ser Gly
    50                  55                  60

Ser Arg Ser Gly Ser Asp Tyr Ser Leu Thr Ile Ser Ser Leu Gln Pro
65                  70                  75                  80

Glu Asp Phe Ala Thr Tyr Tyr Cys Leu Gln Tyr Val Thr Ser Pro Leu
                85                  90                  95

Thr Phe Gly Gly Gly Thr Lys Val Glu Ile Lys
                100                 105
```

<210> SEQ ID NO 25
<211> LENGTH: 107
<212> TYPE: PRT
<213> ORGANISM: Artificial Sequence
<220> FEATURE:
<223> OTHER INFORMATION: light chain variable region, LG2314

<400> SEQUENCE: 25

```
Asp Ile Gln Met Thr Gln Ser Pro Ser Ser Leu Ser Ala Ser Val Gly
1                   5                   10                  15

Asp Arg Val Thr Ile Thr Cys Arg Ala Ser Gln Asp Ile Gly Ser Ser
                20                  25                  30

Leu Asn Trp Leu Gln Gln Lys Pro Gly Lys Ala Ile Lys Arg Leu Ile
            35                  40                  45

Tyr Ala Thr Ser Ser Leu Asp Ser Gly Val Pro Ser Arg Phe Ser Gly
    50                  55                  60

Ser Arg Ser Gly Ser Asp Tyr Thr Leu Thr Ile Ser Ser Leu Gln Pro
65                  70                  75                  80

Glu Asp Phe Ala Thr Tyr Tyr Cys Leu Gln Tyr Val Thr Ser Pro Leu
                85                  90                  95

Thr Phe Gly Gly Gly Thr Lys Val Glu Ile Lys
                100                 105
```

<210> SEQ ID NO 26
<211> LENGTH: 107
<212> TYPE: PRT
<213> ORGANISM: Artificial Sequence -continued

```
<220> FEATURE:
<223> OTHER INFORMATION: light chain variable region, LG2315

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ser Ser
            20                  25                  30

Leu Asn Trp Leu Gln Gln Lys Pro Gly Lys Ala Ile Lys Arg Leu Ile
        35                  40                  45

Tyr Ala Thr Ser Ser Leu Asp Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Val Thr Ser Pro Leu
                85                  90                  95

Thr Phe Gly Gly Gly Thr Lys Val Glu Ile Lys
            100                 105

<210> SEQ ID NO 27
<211> LENGTH: 107
<212> TYPE: PRT
<213> ORGANISM: Artificial Sequence
<220> FEATURE:
<223> OTHER INFORMATION: light chain variable region, LG2316

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ser Ser
            20                  25                  30

Leu Asn Trp Leu Gln Gln Lys Pro Gly Lys Ala Ile Lys Arg Leu Ile
        35                  40                  45

Tyr Ala Thr Ser Ser Leu Asp Ser Gly Val Pro Ser Arg Phe Ser Gly
    50                  55                  60

Ser Arg Ser Gly Ser Asp Phe Thr Leu Thr Ile Ser Ser Leu Gln Pro
65                  70                  75                  80

Glu Asp Phe Ala Thr Tyr Tyr Cys Leu Gln Tyr Val Thr Ser Pro Leu
                85                  90                  95

Thr Phe Gly Gly Gly Thr Lys Val Glu Ile Lys
            100                 105

<210> SEQ ID NO 28
<211> LENGTH: 107
<212> TYPE: PRT
<213> ORGANISM: Artificial Sequence
<220> FEATURE:
<223> OTHER INFORMATION: light chain variable region, LG2317

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ser Ser
            20                  25                  30

Leu Asn Trp Tyr Gln Gln Lys Pro Gly Lys Ala Pro Lys Arg Leu Ile
        35                  40                  45

Tyr Ala Thr Ser Ser Leu Asp Ser Gly Val Pro Ser Arg Phe Ser Gly
    50                  55                  60
```

-continued

---

```
Ser Arg Ser Gly Ser Asp Phe Thr Leu Thr Ile Ser Ser Leu Gln Pro
65              70                  75                  80

Glu Asp Phe Ala Thr Tyr Tyr Cys Leu Gln Tyr Val Thr Ser Pro Leu
                85                  90                  95

Thr Phe Gly Gly Gly Thr Lys Val Glu Ile Lys
            100                 105

<210> SEQ ID NO 29
<211> LENGTH: 107
<212> TYPE: PRT
<213> ORGANISM: Artificial Sequence
<220> FEATURE:
<223> OTHER INFORMATION: light chain variable region, LG2318

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ser Ser
                20                  25                  30

Leu Asn Trp Leu Gln Gln Lys Pro Gly Lys Ala Ile Lys Arg Leu Ile
            35                  40                  45

Tyr Ala Thr Ser Ser Leu Asp Ser Gly Val Pro Ser Arg Phe Ser Gly
    50                  55                  60

Ser Arg Ser Gly Thr Asp Phe Thr Leu Thr Ile Ser Ser Leu Gln Pro
65              70                  75                  80

Glu Asp Phe Ala Thr Tyr Tyr Cys Leu Gln Tyr Val Thr Ser Pro Leu
                85                  90                  95

Thr Phe Gly Gly Gly Thr Lys Val Glu Ile Lys
            100                 105

<210> SEQ ID NO 30
<211> LENGTH: 122
<212> TYPE: PRT
<213> ORGANISM: Artificial Sequence
<220> FEATURE:
<223> OTHER INFORMATION: heavy chain variable region, LG2342

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Gln Gly Leu Glu Trp Met
            35                  40                  45

Gly Gly Ile Asp Pro Glu Thr Glu Gly Ile Ala Tyr Asn Gln Lys Phe
    50                  55                  60

Arg Gly Arg Val Thr Met Thr Thr Asp Thr Ser Thr Ser Thr Ala Tyr
65              70                  75                  80

Met Glu Leu Arg Ser Leu Arg Ser Asp Asp Thr Ala Val Tyr Tyr Cys
                85                  90                  95

Ala Arg Ser Asn Tyr Tyr Gly Gly Arg Glu Ala Trp Phe Ala Tyr Trp
            100                 105                 110

Gly Gln Gly Thr Leu Val Thr Val Ser Ser
        115                 120

<210> SEQ ID NO 31
<211> LENGTH: 122
<212> TYPE: PRT
<213> ORGANISM: Artificial Sequence
```

<220> FEATURE:
<223> OTHER INFORMATION: heavy chain variable region, LG2343

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Lys Gln Ala Pro Gly Gln Gly Leu Glu Trp Ile
        35                  40                  45

Gly Gly Ile Asp Pro Glu Thr Glu Gly Ile Ala Tyr Asn Gln Lys Phe
    50                  55                  60

Arg Gly Arg Ala Thr Leu Thr Ala Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Thr Asn Ser Asn Tyr Tyr Gly Gly Arg Glu Ala Trp Phe Ala Tyr Trp
            100                 105                 110

Gly Gln Gly Thr Leu Val Thr Val Ser Ser
        115                 120

<210> SEQ ID NO 32
<211> LENGTH: 122
<212> TYPE: PRT
<213> ORGANISM: Artificial Sequence
<220> FEATURE:
<223> OTHER INFORMATION: heavy chain variable region, LG2344

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Lys Gln Ala Pro Gly Gln Gly Leu Glu Trp Ile
        35                  40                  45

Gly Gly Ile Asp Pro Glu Thr Glu Gly Ile Ala Tyr Asn Gln Lys Phe
    50                  55                  60

Arg Gly Arg Ala Thr Met Thr Thr Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Thr Asn Ser Asn Tyr Tyr Gly Gly Arg Glu Ala Trp Phe Ala Tyr Trp
            100                 105                 110

Gly Gln Gly Thr Leu Val Thr Val Ser Ser
        115                 120

<210> SEQ ID NO 33
<211> LENGTH: 122
<212> TYPE: PRT
<213> ORGANISM: Artificial Sequence
<220> FEATURE:
<223> OTHER INFORMATION: heavy chain variable region, LG2345

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

-continued

```
Glu Met His Trp Val Lys Gln Ala Pro Gly Gln Gly Leu Glu Trp Ile
        35                  40                  45

Gly Gly Ile Asp Pro Glu Thr Glu Gly Ile Ala Tyr Asn Gln Lys Phe
    50                  55                  60

Arg Gly Arg Ala Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Thr Asn Ser Asn Tyr Tyr Gly Gly Arg Glu Ala Trp Phe Ala Tyr Trp
                100                 105                 110

Gly Gln Gly Thr Leu Val Thr Val Ser Ser
        115                 120
```

<210> SEQ ID NO 34
<211> LENGTH: 122
<212> TYPE: PRT
<213> ORGANISM: Artificial Sequence
<220> FEATURE:
<223> OTHER INFORMATION: heavy chain variable region, LG2346

<400> SEQUENCE: 34

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Lys Gln Ala Pro Gly Gln Gly Leu Glu Trp Ile
        35                  40                  45

Gly Gly Ile Asp Pro Glu Thr Glu Gly Ile Ala Tyr Asn Gln Lys Phe
    50                  55                  60

Arg Gly Arg Ala Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Asn Tyr Tyr Gly Gly Arg Glu Ala Trp Phe Ala Tyr Trp
                100                 105                 110

Gly Gln Gly Thr Leu Val Thr Val Ser Ser
        115                 120
```

<210> SEQ ID NO 35
<211> LENGTH: 122
<212> TYPE: PRT
<213> ORGANISM: Artificial Sequence
<220> FEATURE:
<223> OTHER INFORMATION: heavy chain variable region, LG2347

<400> SEQUENCE: 35

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Lys Gln Ala Pro Gly Gln Gly Leu Glu Trp Met
        35                  40                  45

Gly Gly Ile Asp Pro Glu Thr Glu Gly Ile Ala Tyr Asn Gln Lys Phe
    50                  55                  60

Arg Gly Arg Ala Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95
```

```
Ala Arg Ser Asn Tyr Tyr Gly Gly Arg Glu Ala Trp Phe Ala Tyr Trp
        100                 105                 110

Gly Gln Gly Thr Leu Val Thr Val Ser Ser
        115                 120

<210> SEQ ID NO 36
<211> LENGTH: 122
<212> TYPE: PRT
<213> ORGANISM: Artificial Sequence
<220> FEATURE:
<223> OTHER INFORMATION: heavy chain variable region, LG2348

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Lys Gln Ala Pro Gly Gln Gly Leu Glu Trp Met
        35                  40                  45

Gly Gly Ile Asp Pro Glu Thr Glu Gly Ile Ala Tyr Asn Gln Lys Phe
    50                  55                  60

Arg Gly Arg Ala Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Asn Ser Asn Tyr Tyr Gly Gly Arg Glu Ala Trp Phe Ala Tyr Trp
            100                 105                 110

Gly Gln Gly Thr Leu Val Thr Val Ser Ser
        115                 120

<210> SEQ ID NO 37
<211> LENGTH: 122
<212> TYPE: PRT
<213> ORGANISM: Artificial Sequence
<220> FEATURE:
<223> OTHER INFORMATION: heavy chain variable region, LG2349

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Lys Gln Ala Pro Gly Gln Gly Leu Glu Trp Met
        35                  40                  45

Gly Gly Ile Asp Pro Glu Thr Glu Gly Ile Ala Tyr Asn Gln Lys Phe
    50                  55                  60

Arg Gly Arg Ala Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Thr Arg Ser Asn Tyr Tyr Gly Gly Arg Glu Ala Trp Phe Ala Tyr Trp
            100                 105                 110

Gly Gln Gly Thr Leu Val Thr Val Ser Ser
        115                 120

<210> SEQ ID NO 38
<211> LENGTH: 214
<212> TYPE: PRT
```

```
<213> ORGANISM: Artificial Sequence
<220> FEATURE:
<223> OTHER INFORMATION: Light chain, Ab2315

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ser Ser
            20                  25                  30

Leu Asn Trp Leu Gln Gln Lys Pro Gly Lys Ala Ile Lys Arg Leu Ile
        35                  40                  45

Tyr Ala Thr Ser Ser Leu Asp Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Val Thr Ser Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 39
<211> LENGTH: 214
<212> TYPE: PRT
<213> ORGANISM: Artificial Sequence
<220> FEATURE:
<223> OTHER INFORMATION: Light chain, Ab2317/Ab2325

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ser Ser
            20                  25                  30

Leu Asn Trp Tyr Gln Gln Lys Pro Gly Lys Ala Pro Lys Arg Leu Ile
        35                  40                  45

Tyr Ala Thr Ser Ser Leu Asp Ser Gly Val Pro Ser Arg Phe Ser Gly
    50                  55                  60

Ser Arg Ser Gly Ser Asp Phe Thr Leu Thr Ile Ser Ser Leu Gln Pro
65                  70                  75                  80

Glu Asp Phe Ala Thr Tyr Tyr Cys Leu Gln Tyr Val Thr Ser Pro Leu
                85                  90                  95

Thr Phe Gly Gly Gly Thr Lys Val Glu Ile Lys Arg Thr Val Ala Ala
            100                 105                 110
```

-continued

```
Pro Ser Val Phe Ile Phe Pro Pro Ser Asp Glu Gln Leu Lys Ser Gly
        115             120             125

Thr Ala Ser Val Val Cys Leu Leu Asn Asn Phe Tyr Pro Arg Glu Ala
    130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
        195             200             205

Phe Asn Arg Gly Glu Cys
    210

<210> SEQ ID NO 40
<211> LENGTH: 449
<212> TYPE: PRT
<213> ORGANISM: Artificial Sequence
<220> FEATURE:
<223> OTHER INFORMATION: Heavy chain, Ab2315/Ab2317

<400> SEQUENCE: 40

Gln Val Gln Leu Val Gln Ser Gly Ala Glu Val Lys Lys Pro Gly Ala
1               5               10              15

Ser Val Lys Val Ser Cys Lys Ala Ser Gly Tyr Thr Phe Thr Asp Tyr
            20              25              30

Glu Met His Trp Val Lys Gln Ala Pro Gly Gln Gly Leu Glu Trp Ile
        35              40              45

Gly Gly Ile Asp Pro Glu Thr Glu Gly Ile Ala Tyr Asn Gln Lys Phe
    50              55              60

Arg Gly Arg Ala Thr Leu Thr Ala Asp Lys Ser Thr Ser Thr Ala Tyr
65              70              75              80

Met Glu Leu Arg Ser Leu Arg Ser Asp Asp Thr Ala Val Tyr Tyr Cys
            85              90              95

Thr Asn Ser Asn Tyr Tyr Gly Gly Arg Glu Ala Trp Phe Ala Tyr Trp
            100             105             110

Gly Gln Gly Thr Leu Val Thr Val Ser Ser Ala Ser Thr Lys Gly Pro
        115             120             125

Ser Val Phe Pro Leu Ala Pro Cys Ser Arg Ser Thr Ser Glu Ser Thr
    130             135             140

Ala Ala Leu Gly Cys Leu Val Lys Asp Tyr Phe Pro Glu Pro Val Thr
145             150             155             160

Val Ser Trp Asn Ser Gly Ala Leu Thr Ser Gly Val His Thr Phe Pro
            165             170             175

Ala Val Leu Gln Ser Ser Gly Leu Tyr Ser Leu Ser Ser Val Val Thr
            180             185             190

Val Pro Ser Ser Ser Leu Gly Thr Lys Thr Tyr Thr Cys Asn Val Asp
        195             200             205

His Lys Pro Ser Asn Thr Lys Val Asp Lys Arg Val Glu Ser Lys Tyr
    210             215             220

Gly Pro Pro Cys Pro Pro Cys Pro Ala Pro Glu Phe Leu Gly Gly Pro
225             230             235             240

Ser Val Phe Leu Phe Pro Pro Lys Pro Lys Asp Thr Leu Met Ile Ser
            245             250             255
```

-continued

```
Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Lys
```

```
<210> SEQ ID NO 41
<211> LENGTH: 449
<212> TYPE: PRT
<213> ORGANISM: Artificial Sequence
<220> FEATURE:
<223> OTHER INFORMATION: Heavy chain, Ab2325

<400> SEQUENCE: 41
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Lys Gln Ala Pro Gly Gln Gly Leu Glu Trp Met
        35                  40                  45

Gly Gly Ile Asp Pro Glu Thr Glu Gly Ile Ala Tyr Asn Gln Lys Phe
    50                  55                  60

Arg Gly Arg Ala Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Asn Ser Asn Tyr Tyr Gly Gly Arg Glu Ala Trp Phe Ala Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
```

-continued

```
                 165             170             175
Ala Val Leu Gln Ser Ser Gly Leu Tyr Ser Leu Ser Ser Val Val Thr
            180             185             190

Val Pro Ser Ser Ser Leu Gly Thr Lys Thr Tyr Thr Cys Asn Val Asp
            195             200             205

His Lys Pro Ser Asn Thr Lys Val Asp Lys Arg Val Glu Ser Lys Tyr
            210             215             220

Gly Pro Pro Cys Pro Pro Cys Pro Ala Pro Glu Phe Leu Gly Gly Pro
225             230             235             240

Ser Val Phe Leu Phe Pro Pro Lys Pro Lys Asp Thr Leu Met Ile Ser
            245             250             255

Arg Thr Pro Glu Val Thr Cys Val Val Val Asp Val Ser Gln Glu Asp
            260             265             270

Pro Glu Val Gln Phe Asn Trp Tyr Val Asp Gly Val Glu Val His Asn
            275             280             285

Ala Lys Thr Lys Pro Arg Glu Glu Gln Phe Asn Ser Thr Tyr Arg Val
            290             295             300

Val Ser Val Leu Thr Val Leu His Gln Asp Trp Leu Asn Gly Lys Glu
305             310             315             320

Tyr Lys Cys Lys Val Ser Asn Lys Gly Leu Pro Ser Ser Ile Glu Lys
            325             330             335

Thr Ile Ser Lys Ala Lys Gly Gln Pro Arg Glu Pro Gln Val Tyr Thr
            340             345             350

Leu Pro Pro Ser Gln Glu Glu Met Thr Lys Asn Gln Val Ser Leu Thr
            355             360             365

Cys Leu Val Lys Gly Phe Tyr Pro Ser Asp Ile Ala Val Glu Trp Glu
            370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Arg Leu Thr Val Asp Lys
            405             410             415

Ser Arg Trp Gln Glu Gly Asn Val Phe Ser Cys Ser Val Met His Glu
            420             425             430

Ala Leu His Asn His Tyr Thr Gln Lys Ser Leu Ser Leu Ser Leu Gly
            435             440             445

Lys
```

```
<210> SEQ ID NO 42
<211> LENGTH: 214
<212> TYPE: PRT
<213> ORGANISM: Artificial Sequence
<220> FEATURE:
<223> OTHER INFORMATION: Nivolumab light chain

<400> SEQUENCE: 42

Glu Ile Val Leu Thr Gln Ser Pro Ala Thr Leu Ser Leu Ser Pro Gly
1               5               10              15

Glu Arg Ala Thr Leu Ser Cys Arg Ala Ser Gln Ser Val Ser Ser Tyr
            20              25              30

Leu Ala Trp Tyr Gln Gln Lys Pro Gly Gln Ala Pro Arg Leu Leu Ile
            35              40              45

Tyr Asp Ala Ser Asn Arg Ala Thr Gly Ile Pro Ala Arg Phe Ser Gly
            50              55              60

Ser Gly Ser Gly Thr Asp Phe Thr Leu Thr Ile Ser Ser Leu Glu Pro
65              70              75              80
```

-continued

```
Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 43
<211> LENGTH: 440
<212> TYPE: PRT
<213> ORGANISM: Artificial Sequence
<220> FEATURE:
<223> OTHER INFORMATION: Nivolumab heavy chain

<400> SEQUENCE: 43
```

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
            195                 200                 205

Lys Arg Val Glu Ser Lys Tyr Gly Pro Pro Cys Pro Pro Cys Pro Ala
    210                 215                 220
```

-continued

```
Pro Glu Phe Leu Gly Gly Pro Ser Val Phe Leu Phe Pro Pro Lys Pro
225             230             235             240

Lys Asp Thr Leu Met Ile Ser Arg Thr Pro Glu Val Thr Cys Val Val
            245             250             255

Val Asp Val Ser Gln Glu Asp Pro Glu Val Gln Phe Asn Trp Tyr Val
            260             265             270

Asp Gly Val Glu Val His Asn Ala Lys Thr Lys Pro Arg Glu Glu Gln
            275             280             285

Phe Asn Ser Thr Tyr Arg Val Val Ser Val Leu Thr Val Leu His Gln
    290             295             300

Asp Trp Leu Asn Gly Lys Glu Tyr Lys Cys Lys Val Ser Asn Lys Gly
305             310             315             320

Leu Pro Ser Ser Ile Glu Lys Thr Ile Ser Lys Ala Lys Gly Gln Pro
            325             330             335

Arg Glu Pro Gln Val Tyr Thr Leu Pro Pro Ser Gln Glu Glu Met Thr
            340             345             350

Lys Asn Gln Val Ser Leu Thr Cys Leu Val Lys Gly Phe Tyr Pro Ser
    355             360             365

Asp Ile Ala Val Glu Trp Glu Ser Asn Gly Gln Pro Glu Asn Asn Tyr
    370             375             380

Lys Thr Thr Pro Pro Val Leu Asp Ser Asp Gly Ser Phe Phe Leu Tyr
385             390             395             400

Ser Arg Leu Thr Val Asp Lys Ser Arg Trp Gln Glu Gly Asn Val Phe
            405             410             415

Ser Cys Ser Val Met His Glu Ala Leu His Asn His Tyr Thr Gln Lys
            420             425             430

Ser Leu Ser Leu Ser Leu Gly Lys
    435             440
```

```
<210> SEQ ID NO 44
<211> LENGTH: 218
<212> TYPE: PRT
<213> ORGANISM: Artificial Sequence
<220> FEATURE:
<223> OTHER INFORMATION: Pembrolizumab light chain

<400> SEQUENCE: 44
```

```
Glu Ile Val Leu Thr Gln Ser Pro Ala Thr Leu Ser Leu Ser Pro Gly
1               5               10              15

Glu Arg Ala Thr Leu Ser Cys Arg Ala Ser Lys Gly Val Ser Thr Ser
            20              25              30

Gly Tyr Ser Tyr Leu His Trp Tyr Gln Gln Lys Pro Gly Gln Ala Pro
    35              40              45

Arg Leu Leu Ile Tyr Leu Ala Ser Tyr Leu Glu Ser Gly Val Pro Ala
    50              55              60

Arg Phe Ser Gly Ser Gly Ser Gly Thr Asp Phe Thr Leu Thr Ile Ser
65              70              75              80

Ser Leu Glu Pro Glu Asp Phe Ala Val Tyr Tyr Cys Gln His Ser Arg
            85              90              95

Asp Leu Pro Leu Thr Phe Gly Gly Gly Thr Lys Val Glu Ile Lys Arg
            100             105             110

Thr Val Ala Ala Pro Ser Val Phe Ile Phe Pro Pro Ser Asp Glu Gln
        115             120             125

Leu Lys Ser Gly Thr Ala Ser Val Val Cys Leu Leu Asn Asn Phe Tyr
    130             135             140
```

```
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 45
<211> LENGTH: 447
<212> TYPE: PRT
<213> ORGANISM: Artificial Sequence
<220> FEATURE:
<223> OTHER INFORMATION: Pembrolizumab heavy chain

<400> SEQUENCE: 45

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
        50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285
```

-continued

```
Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
                435                 440                 445

<210> SEQ ID NO 46
<211> LENGTH: 706
<212> TYPE: PRT
<213> ORGANISM: Artificial Sequence
<220> FEATURE:
<223> OTHER INFORMATION: Amino acid sequence of LB2371 comprising a
      heavy chain

<400> SEQUENCE: 46

Asp Ile Gln Met Thr Gln Ser Pro Ser Ser Leu Ser Ala Ser Val Gly
1                 5                 10                  15

Asp Arg Val Thr Ile Thr Cys Arg Ala Ser Gln Asp Ile Gly Ser Ser
                20                  25                  30

Leu Asn Trp Tyr Gln Gln Lys Pro Gly Lys Ala Pro Lys Arg Leu Ile
            35                  40                  45

Tyr Ala Thr Ser Ser Leu Asp Ser Gly Val Pro Ser Arg Phe Ser Gly
    50                  55                  60

Ser Arg Ser Gly Ser Asp Phe Thr Leu Thr Ile Ser Ser Leu Gln Pro
65                  70                  75                  80

Glu Asp Phe Ala Thr Tyr Tyr Cys Leu Gln Tyr Val Thr Ser Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gln Val Gln Leu Val Gln
        115                 120                 125

Ser Gly Ala Glu Val Lys Lys Pro Gly Ala Ser Val Lys Val Ser Cys
    130                 135                 140

Lys Ala Ser Gly Tyr Thr Phe Thr Asp Tyr Glu Met His Trp Val Lys
145                 150                 155                 160

Gln Ala Pro Gly Gln Gly Leu Glu Trp Ile Gly Gly Ile Asp Pro Glu
                165                 170                 175

Thr Glu Gly Ile Ala Tyr Asn Gln Lys Phe Arg Gly Arg Ala Thr Leu
            180                 185                 190

Thr Ala Asp Lys Ser Thr Ser Thr Ala Tyr Met Glu Leu Arg Ser Leu
```

-continued

```
               195                200                205

Arg Ser Asp Asp Thr Ala Val Tyr Tyr Cys Thr Asn Ser Asn Tyr Tyr
    210                215                220

Gly Gly Arg Glu Ala Trp Phe Ala Tyr Trp Gly Gln Gly Thr Leu Val
225                230                235                240

Thr Val Ser Ser Gly Gly Gly Ser Gly Gly Gly Ser Gly Gly
                245                250                255

Gly Gly Ser Gln Val Gln Leu Val Gln Ser Gly Val Glu Val Lys Lys
                260                265                270

Pro Gly Ala Ser Val Lys Val Ser Cys Lys Ala Ser Gly Tyr Thr Phe
                275                280                285

Thr Asn Tyr Tyr Met Tyr Trp Val Arg Gln Ala Pro Gly Gln Gly Leu
    290                295                300

Glu Trp Met Gly Gly Ile Asn Pro Ser Asn Gly Gly Thr Asn Phe Asn
305                310                315                320

Glu Lys Phe Lys Asn Arg Val Thr Leu Thr Thr Asp Ser Ser Thr Thr
                325                330                335

Thr Ala Tyr Met Glu Leu Lys Ser Leu Gln Phe Asp Asp Thr Ala Val
                340                345                350

Tyr Tyr Cys Ala Arg Arg Asp Tyr Arg Phe Asp Met Gly Phe Asp Tyr
                355                360                365

Trp Gly Gln Gly Thr Thr Val Thr Val Ser Ser Ala Ser Thr Lys Gly
    370                375                380

Pro Ser Val Phe Pro Leu Ala Pro Cys Ser Arg Ser Thr Ser Glu Ser
385                390                395                400

Thr Ala Ala Leu Gly Cys Leu Val Lys Asp Tyr Phe Pro Glu Pro Val
                405                410                415

Thr Val Ser Trp Asn Ser Gly Ala Leu Thr Ser Gly Val His Thr Phe
                420                425                430

Pro Ala Val Leu Gln Ser Ser Gly Leu Tyr Ser Leu Ser Ser Val Val
                435                440                445

Thr Val Pro Ser Ser Ser Leu Gly Thr Lys Thr Tyr Thr Cys Asn Val
    450                455                460

Asp His Lys Pro Ser Asn Thr Lys Val Asp Lys Arg Val Glu Ser Lys
465                470                475                480

Tyr Gly Pro Pro Cys Pro Pro Cys Pro Ala Pro Glu Phe Leu Gly Gly
                485                490                495

Pro Ser Val Phe Leu Phe Pro Pro Lys Pro Lys Asp Thr Leu Met Ile
                500                505                510

Ser Arg Thr Pro Glu Val Thr Cys Val Val Val Asp Val Ser Gln Glu
    515                520                525

Asp Pro Glu Val Gln Phe Asn Trp Tyr Val Asp Gly Val Glu Val His
    530                535                540

Asn Ala Lys Thr Lys Pro Arg Glu Glu Gln Phe Asn Ser Thr Tyr Arg
545                550                555                560

Val Val Ser Val Leu Thr Val Leu His Gln Asp Trp Leu Asn Gly Lys
                565                570                575

Glu Tyr Lys Cys Lys Val Ser Asn Lys Gly Leu Pro Ser Ser Ile Glu
                580                585                590

Lys Thr Ile Ser Lys Ala Lys Gly Gln Pro Arg Glu Pro Gln Val Tyr
                595                600                605

Thr Leu Pro Pro Ser Gln Glu Glu Met Thr Lys Asn Gln Val Ser Leu
    610                615                620
```

-continued

```
Thr Cys Leu Val Lys Gly Phe Tyr Pro Ser Asp Ile Ala Val Glu Trp
625             630             635             640

Glu Ser Asn Gly Gln Pro Glu Asn Asn Tyr Lys Thr Thr Pro Pro Val
                645             650             655

Leu Asp Ser Asp Gly Ser Phe Phe Leu Tyr Ser Arg Leu Thr Val Asp
            660             665             670

Lys Ser Arg Trp Gln Glu Gly Asn Val Phe Ser Cys Ser Val Met His
        675             680             685

Glu Ala Leu His Asn His Tyr Thr Gln Lys Ser Leu Ser Leu Ser Leu
    690             695             700

Gly Lys
705
```

```
<210> SEQ ID NO 47
<211> LENGTH: 699
<212> TYPE: PRT
<213> ORGANISM: Artificial Sequence
<220> FEATURE:
<223> OTHER INFORMATION: Amino acid sequence of LB2373 comprising a
      heavy chain

<400> SEQUENCE: 47
```

```
Asp Ile Gln Met Thr Gln Ser Pro Ser Ser Leu Ser Ala Ser Val Gly
1               5               10              15

Asp Arg Val Thr Ile Thr Cys Arg Ala Ser Gln Asp Ile Gly Ser Ser
            20              25              30

Leu Asn Trp Tyr Gln Gln Lys Pro Gly Lys Ala Pro Lys Arg Leu Ile
        35              40              45

Tyr Ala Thr Ser Ser Leu Asp Ser Gly Val Pro Ser Arg Phe Ser Gly
    50              55              60

Ser Arg Ser Gly Ser Asp Phe Thr Leu Thr Ile Ser Ser Leu Gln Pro
65              70              75              80

Glu Asp Phe Ala Thr Tyr Tyr Cys Leu Gln Tyr Val Thr Ser Pro Leu
                85              90              95

Thr Phe Gly Gly Gly Thr Lys Val Glu Ile Lys Gly Gly Gly Gly Ser
            100             105             110

Gly Gly Gly Gly Ser Gly Gly Gly Ser Gln Val Gln Leu Val Gln
        115             120             125

Ser Gly Ala Glu Val Lys Lys Pro Gly Ala Ser Val Lys Val Ser Cys
    130             135             140

Lys Ala Ser Gly Tyr Thr Phe Thr Asp Tyr Glu Met His Trp Val Lys
145             150             155             160

Gln Ala Pro Gly Gln Gly Leu Glu Trp Ile Gly Gly Ile Asp Pro Glu
            165             170             175

Thr Glu Gly Ile Ala Tyr Asn Gln Lys Phe Arg Gly Arg Ala Thr Leu
            180             185             190

Thr Ala Asp Lys Ser Thr Ser Thr Ala Tyr Met Glu Leu Arg Ser Leu
        195             200             205

Arg Ser Asp Asp Thr Ala Val Tyr Tyr Cys Thr Asn Ser Asn Tyr Tyr
    210             215             220

Gly Gly Arg Glu Ala Trp Phe Ala Tyr Trp Gly Gln Gly Thr Leu Val
225             230             235             240

Thr Val Ser Ser Gly Gly Gly Ser Gly Gly Gly Ser Gly Gly
            245             250             255

Gly Gly Ser Gln Val Gln Leu Val Glu Ser Gly Gly Gly Val Val Gln
```

-continued

```
                  260                 265                 270

Pro Gly Arg Ser Leu Arg Leu Asp Cys Lys Ala Ser Gly Ile Thr Phe
          275                 280                 285

Ser Asn Ser Gly Met His Trp Val Arg Gln Ala Pro Gly Lys Gly Leu
          290                 295                 300

Glu Trp Val Ala Val Ile Trp Tyr Asp Gly Ser Lys Arg Tyr Tyr Ala
305                 310                 315                 320

Asp Ser Val Lys Gly Arg Phe Thr Ile Ser Arg Asp Asn Ser Lys Asn
                  325                 330                 335

Thr Leu Phe Leu Gln Met Asn Ser Leu Arg Ala Glu Asp Thr Ala Val
          340                 345                 350

Tyr Tyr Cys Ala Thr Asn Asp Asp Tyr Trp Gly Gln Gly Thr Leu Val
          355                 360                 365

Thr Val Ser Ser Ala Ser Thr Lys Gly Pro Ser Val Phe Pro Leu Ala
          370                 375                 380

Pro Cys Ser Arg Ser Thr Ser Glu Ser Thr Ala Ala Leu Gly Cys Leu
385                 390                 395                 400

Val Lys Asp Tyr Phe Pro Glu Pro Val Thr Val Ser Trp Asn Ser Gly
                  405                 410                 415

Ala Leu Thr Ser Gly Val His Thr Phe Pro Ala Val Leu Gln Ser Ser
          420                 425                 430

Gly Leu Tyr Ser Leu Ser Ser Val Val Thr Val Pro Ser Ser Ser Leu
          435                 440                 445

Gly Thr Lys Thr Tyr Thr Cys Asn Val Asp His Lys Pro Ser Asn Thr
          450                 455                 460

Lys Val Asp Lys Arg Val Glu Ser Lys Tyr Gly Pro Pro Cys Pro Pro
465                 470                 475                 480

Cys Pro Ala Pro Glu Phe Leu Gly Gly Pro Ser Val Phe Leu Phe Pro
                  485                 490                 495

Pro Lys Pro Lys Asp Thr Leu Met Ile Ser Arg Thr Pro Glu Val Thr
          500                 505                 510

Cys Val Val Val Asp Val Ser Gln Glu Asp Pro Glu Val Gln Phe Asn
          515                 520                 525

Trp Tyr Val Asp Gly Val Glu Val His Asn Ala Lys Thr Lys Pro Arg
          530                 535                 540

Glu Glu Gln Phe Asn Ser Thr Tyr Arg Val Val Ser Val Leu Thr Val
545                 550                 555                 560

Leu His Gln Asp Trp Leu Asn Gly Lys Glu Tyr Lys Cys Lys Val Ser
                  565                 570                 575

Asn Lys Gly Leu Pro Ser Ser Ile Glu Lys Thr Ile Ser Lys Ala Lys
          580                 585                 590

Gly Gln Pro Arg Glu Pro Gln Val Tyr Thr Leu Pro Pro Ser Gln Glu
          595                 600                 605

Glu Met Thr Lys Asn Gln Val Ser Leu Thr Cys Leu Val Lys Gly Phe
          610                 615                 620

Tyr Pro Ser Asp Ile Ala Val Glu Trp Glu Ser Asn Gly Gln Pro Glu
625                 630                 635                 640

Asn Asn Tyr Lys Thr Thr Pro Pro Val Leu Asp Ser Asp Gly Ser Phe
                  645                 650                 655

Phe Leu Tyr Ser Arg Leu Thr Val Asp Lys Ser Arg Trp Gln Glu Gly
          660                 665                 670

Asn Val Phe Ser Cys Ser Val Met His Glu Ala Leu His Asn His Tyr
          675                 680                 685
```

-continued

```
Thr Gln Lys Ser Leu Ser Leu Ser Leu Gly Lys
    690             695

<210> SEQ ID NO 48
<211> LENGTH: 699
<212> TYPE: PRT
<213> ORGANISM: Artificial Sequence
<220> FEATURE:
<223> OTHER INFORMATION: Amino acid sequence of LB2374 comprising a
      heavy chain

<400> SEQUENCE: 48

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
```

-continued

```
              340             345             350

Lys Asn Gln Val Ser Leu Thr Cys Leu Val Lys Gly Phe Tyr Pro Ser
        355             360             365

Asp Ile Ala Val Glu Trp Glu Ser Asn Gly Gln Pro Glu Asn Asn Tyr
    370             375             380

Lys Thr Thr Pro Pro Val Leu Asp Ser Asp Gly Ser Phe Phe Leu Tyr
385             390             395             400

Ser Arg Leu Thr Val Asp Lys Ser Arg Trp Gln Glu Gly Asn Val Phe
            405             410             415

Ser Cys Ser Val Met His Glu Ala Leu His Asn His Tyr Thr Gln Lys
        420             425             430

Ser Leu Ser Leu Ser Leu Gly Ala Gly Gly Gly Ser Gly Gly Gly
        435             440             445

Gly Ser Gly Gly Gly Gly Ser Gln Val Gln Leu Val Gln Ser Gly Ala
    450             455             460

Glu Val Lys Lys Pro Gly Ala Ser Val Lys Val Ser Cys Lys Ala Ser
465             470             475             480

Gly Tyr Thr Phe Thr Asp Tyr Glu Met His Trp Val Lys Gln Ala Pro
            485             490             495

Gly Gln Gly Leu Glu Trp Ile Gly Gly Ile Asp Pro Glu Thr Glu Gly
        500             505             510

Ile Ala Tyr Asn Gln Lys Phe Arg Gly Arg Ala Thr Leu Thr Ala Asp
        515             520             525

Lys Ser Thr Ser Thr Ala Tyr Met Glu Leu Arg Ser Leu Arg Ser Asp
    530             535             540

Asp Thr Ala Val Tyr Tyr Cys Thr Asn Ser Asn Tyr Tyr Gly Gly Arg
545             550             555             560

Glu Ala Trp Phe Ala Tyr Trp Gly Gln Gly Thr Leu Val Thr Val Ser
            565             570             575

Ser Gly Gly Gly Gly Ser Gly Gly Gly Gly Ser Gly Gly Gly Gly Ser
            580             585             590

Asp Ile Gln Met Thr Gln Ser Pro Ser Ser Leu Ser Ala Ser Val Gly
        595             600             605

Asp Arg Val Thr Ile Thr Cys Arg Ala Ser Gln Asp Ile Gly Ser Ser
    610             615             620

Leu Asn Trp Tyr Gln Gln Lys Pro Gly Lys Ala Pro Lys Arg Leu Ile
625             630             635             640

Tyr Ala Thr Ser Ser Leu Asp Ser Gly Val Pro Ser Arg Phe Ser Gly
            645             650             655

Ser Arg Ser Gly Ser Asp Phe Thr Leu Thr Ile Ser Ser Leu Gln Pro
            660             665             670

Glu Asp Phe Ala Thr Tyr Tyr Cys Leu Gln Tyr Val Thr Ser Pro Leu
            675             680             685

Thr Phe Gly Gly Gly Thr Lys Val Glu Ile Lys
    690             695
```

<210> SEQ ID NO 49
<211> LENGTH: 473
<212> TYPE: PRT
<213> ORGANISM: Artificial Sequence
<220> FEATURE:
<223> OTHER INFORMATION: Amino acid sequence of LB2379 comprising a
      light chain

<400> SEQUENCE: 49

-continued

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ser Ser
            20                  25                  30

Leu Asn Trp Tyr Gln Gln Lys Pro Gly Lys Ala Pro Lys Arg Leu Ile
        35                  40                  45

Tyr Ala Thr Ser Ser Leu Asp Ser Gly Val Pro Ser Arg Phe Ser Gly
    50                  55                  60

Ser Arg Ser Gly Ser Asp Phe Thr Leu Thr Ile Ser Ser Leu Gln Pro
65                  70                  75                  80

Glu Asp Phe Ala Thr Tyr Tyr Cys Leu Gln Tyr Val Thr Ser Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gln Val Gln Leu Val Gln
            115                 120                 125

Ser Gly Ala Glu Val Lys Lys Pro Gly Ala Ser Val Lys Val Ser Cys
    130                 135                 140

Lys Ala Ser Gly Tyr Thr Phe Thr Asp Tyr Glu Met His Trp Val Lys
145                 150                 155                 160

Gln Ala Pro Gly Gln Gly Leu Glu Trp Ile Gly Gly Ile Asp Pro Glu
            165                 170                 175

Thr Glu Gly Ile Ala Tyr Asn Gln Lys Phe Arg Gly Arg Ala Thr Leu
            180                 185                 190

Thr Ala Asp Lys Ser Thr Ser Thr Ala Tyr Met Glu Leu Arg Ser Leu
            195                 200                 205

Arg Ser Asp Asp Thr Ala Val Tyr Tyr Cys Thr Asn Ser Asn Tyr Tyr
    210                 215                 220

Gly Gly Arg Glu Ala Trp Phe Ala Tyr Trp Gly Gln Gly Thr Leu Val
225                 230                 235                 240

Thr Val Ser Ser Gly Gly Gly Gly Ser Gly Gly Gly Gly Ser Gly Gly
            245                 250                 255

Gly Gly Ser Glu Ile Val Leu Thr Gln Ser Pro Ala Thr Leu Ser Leu
            260                 265                 270

Ser Pro Gly Glu Arg Ala Thr Leu Ser Cys Arg Ala Ser Gln Ser Val
            275                 280                 285

Ser Ser Tyr Leu Ala Trp Tyr Gln Gln Lys Pro Gly Gln Ala Pro Arg
    290                 295                 300

Leu Leu Ile Tyr Asp Ala Ser Asn Arg Ala Thr Gly Ile Pro Ala Arg
305                 310                 315                 320

Phe Ser Gly Ser Gly Ser Gly Thr Asp Phe Thr Leu Thr Ile Ser Ser
            325                 330                 335

Leu Glu Pro Glu Asp Phe Ala Val Tyr Tyr Cys Gln Gln Ser Ser Asn
            340                 345                 350

Trp Pro Arg Thr Phe Gly Gln Gly Thr Lys Val Glu Ile Lys Arg Thr
            355                 360                 365

Val Ala Ala Pro Ser Val Phe Ile Phe Pro Pro Ser Asp Glu Gln Leu
    370                 375                 380

Lys Ser Gly Thr Ala Ser Val Val Cys Leu Leu Asn Asn Phe Tyr Pro
385                 390                 395                 400

Arg Glu Ala Lys Val Gln Trp Lys Val Asp Asn Ala Leu Gln Ser Gly
                405                 410                 415

Asn Ser Gln Glu Ser Val Thr Glu Gln Asp Ser Lys Asp Ser Thr Tyr
```

-continued

```
                  420             425             430
Ser Leu Ser Ser Thr Leu Thr Leu Ser Lys Ala Asp Tyr Glu Lys His
        435             440             445

Lys Val Tyr Ala Cys Glu Val Thr His Gln Gly Leu Ser Ser Pro Val
    450             455             460

Thr Lys Ser Phe Asn Arg Gly Glu Cys
465             470

<210> SEQ ID NO 50
<211> LENGTH: 473
<212> TYPE: PRT
<213> ORGANISM: Artificial Sequence
<220> FEATURE:
<223> OTHER INFORMATION: Amino acid sequence of LB2380 comprising a
      light chain

<400> SEQUENCE: 50

Glu Ile Val Leu Thr Gln Ser Pro Ala Thr Leu Ser Leu Ser Pro Gly
1               5               10              15

Glu Arg Ala Thr Leu Ser Cys Arg Ala Ser Gln Ser Val Ser Ser Tyr
            20              25              30

Leu Ala Trp Tyr Gln Gln Lys Pro Gly Gln Ala Pro Arg Leu Leu Ile
        35              40              45

Tyr Asp Ala Ser Asn Arg Ala Thr Gly Ile Pro Ala Arg Phe Ser Gly
    50              55              60

Ser Gly Ser Gly Thr Asp Phe Thr Leu Thr Ile Ser Ser Leu Glu Pro
65              70              75              80

Glu Asp Phe Ala Val Tyr Tyr Cys Gln Gln Ser Ser Asn Trp Pro Arg
                85              90              95

Thr Phe Gly Gln Gly Thr Lys Val Glu Ile Lys Arg Thr Val Ala Ala
            100             105             110

Pro Ser Val Phe Ile Phe Pro Pro Ser Asp Glu Gln Leu Lys Ser Gly
            115             120             125

Thr Ala Ser Val Val Cys Leu Leu Asn Asn Phe Tyr Pro Arg Glu Ala
    130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
    195             200             205

Phe Asn Arg Gly Glu Cys Gly Gly Gly Gly Ser Gly Gly Gly Gly Ser
    210             215             220

Gly Gly Gly Gly Ser Gln Val Gln Leu Val Gln Ser Gly Ala Glu Val
225             230             235             240

Lys Lys Pro Gly Ala Ser Val Lys Val Ser Cys Lys Ala Ser Gly Tyr
            245             250             255

Thr Phe Thr Asp Tyr Glu Met His Trp Val Lys Gln Ala Pro Gly Gln
            260             265             270

Gly Leu Glu Trp Ile Gly Gly Ile Asp Pro Glu Thr Glu Gly Ile Ala
        275             280             285

Tyr Asn Gln Lys Phe Arg Gly Arg Ala Thr Leu Thr Ala Asp Lys Ser
    290             295             300
```

```
Thr Ser Thr Ala Tyr Met Glu Leu Arg Ser Leu Arg Ser Asp Asp Thr
305             310             315             320

Ala Val Tyr Tyr Cys Thr Asn Ser Asn Tyr Tyr Gly Gly Arg Glu Ala
                325             330             335

Trp Phe Ala Tyr Trp Gly Gln Gly Thr Leu Val Thr Val Ser Ser Gly
            340             345             350

Gly Gly Gly Ser Gly Gly Gly Gly Ser Gly Gly Gly Ser Asp Ile
            355             360             365

Gln Met Thr Gln Ser Pro Ser Ser Leu Ser Ala Ser Val Gly Asp Arg
    370             375             380

Val Thr Ile Thr Cys Arg Ala Ser Gln Asp Ile Gly Ser Ser Leu Asn
385             390             395             400

Trp Tyr Gln Gln Lys Pro Gly Lys Ala Pro Lys Arg Leu Ile Tyr Ala
                405             410             415

Thr Ser Ser Leu Asp Ser Gly Val Pro Ser Arg Phe Ser Gly Ser Arg
            420             425             430

Ser Gly Ser Asp Phe Thr Leu Thr Ile Ser Ser Leu Gln Pro Glu Asp
        435             440             445

Phe Ala Thr Tyr Tyr Cys Leu Gln Tyr Val Thr Ser Pro Leu Thr Phe
    450             455             460

Gly Gly Gly Thr Lys Val Glu Ile Lys
465             470

<210> SEQ ID NO 51
<211> LENGTH: 5
<212> TYPE: PRT
<213> ORGANISM: Artificial Sequence
<220> FEATURE:
<223> OTHER INFORMATION: Synthesized

<400> SEQUENCE: 51

Gly Gly Gly Gly Ser
1               5

<210> SEQ ID NO 52
<211> LENGTH: 10
<212> TYPE: PRT
<213> ORGANISM: Artificial Sequence
<220> FEATURE:
<223> OTHER INFORMATION: Synthesized

<400> SEQUENCE: 52

Gly Gly Gly Gly Ser Gly Gly Gly Gly Ser
1               5                   10

<210> SEQ ID NO 53
<211> LENGTH: 15
<212> TYPE: PRT
<213> ORGANISM: Artificial Sequence
<220> FEATURE:
<223> OTHER INFORMATION: Synthesized

<400> SEQUENCE: 53

Gly Gly Gly Gly Ser Gly Gly Gly Gly Ser Gly Gly Gly Gly Ser
1               5                   10                  15

<210> SEQ ID NO 54
<211> LENGTH: 20
<212> TYPE: PRT
<213> ORGANISM: Artificial Sequence
<220> FEATURE:
<223> OTHER INFORMATION: Synthesized
```

-continued

```
<400> SEQUENCE: 54

Gly Gly Gly Gly Ser Gly Gly Gly Gly Ser Gly Gly Gly Gly Ser Gly
1               5                   10                  15

Gly Gly Gly Ser
            20
```